US010683368B2

(12) United States Patent
Moessner et al.

(10) Patent No.: US 10,683,368 B2
(45) Date of Patent: Jun. 16, 2020

(54) FC-REGION VARIANTS WITH MODIFIED FCRN-BINDING AND METHODS OF USE

(71) Applicant: Hoffmann-La Roche Inc., Little Falls, NJ (US)

(72) Inventors: Ekkehard Moessner, Kreuzlingen (CH); Tilman Schlothauer, Penzberg (DE)

(73) Assignee: Hoffmann-La Roche Inc., Little Falls, NJ (US)

( * ) Notice: Subject to any disclaimer, the term of this patent is extended or adjusted under 35 U.S.C. 154(b) by 68 days.

(21) Appl. No.: 15/586,679

(22) Filed: May 4, 2017

(65) Prior Publication Data

US 2017/0342167 A1 Nov. 30, 2017

Related U.S. Application Data

(63) Continuation of application No. PCT/EP2015/075656, filed on Nov. 4, 2015.

(30) Foreign Application Priority Data

Nov. 6, 2014 (EP) .................................... 14192052

(51) Int. Cl.
C07K 16/46 (2006.01)
C07K 16/00 (2006.01)

(52) U.S. Cl.
CPC ............ C07K 16/468 (2013.01); C07K 16/00 (2013.01); C07K 2317/31 (2013.01);
(Continued)

(58) Field of Classification Search
None
See application file for complete search history.

(56) References Cited

U.S. PATENT DOCUMENTS 4,900,660 A  2/1990  Boyle et al.
5,623,053 A  4/1997  Gastinel et al.
(Continued)

FOREIGN PATENT DOCUMENTS

EP  1790716     5/2007
JP  2008-504002 2/2008
(Continued)

OTHER PUBLICATIONS

Yeung et al. (Cancer Res., 70: 3269-3277, 2010).*
(Continued)

Primary Examiner — Nelson B Moseley, II
(74) Attorney, Agent, or Firm — Grant Kalinowski

(57) ABSTRACT

Herein is reported an IgG class Fc-region comprising a first variant Fc-region polypeptide and a second variant Fc-region polypeptide, wherein a) the first variant Fc-region polypeptide is derived from a first parent IgG class Fc-region polypeptide and the second variant Fc-region polypeptide is derived from a second parent IgG class Fc-region polypeptide, whereby the first parent IgG class Fc-region polypeptide is identical to or different from the second parent IgG class Fc-region polypeptide, and b) the first variant Fc-region polypeptide differs from the second variant Fc-region polypeptide in one or more amino acid residues other than those amino acid residues in which the first parent IgG class Fc-region polypeptide differs from the second parent IgG class Fc-region polypeptide, and c) the IgG class Fc-region comprising the first variant Fc-region polypeptide and the second variant Fc-region polypeptide has an affinity to a human Fc-receptor that is different than that of an IgG class Fc-region comprising the first parent IgG class Fc-region polypeptide of a) and the second parent IgG class Fc-region polypeptide of a), wherein either the first Fc-region polypeptide or the second Fc-region polypeptide or both Fc-region polypeptides comprise independently of each other one of the following mutations or combination of mutations: T307H, or Q311H, or E430 H, or N434H, or T307H and Q311H, or T307H and E430H, or T307H and N434A, or T307H and N434H, or T307Q and Q311H, or T307Q and E430H, or T307Q and N434H, or T307H and Q311H and E430H and N434A, or T307H and Q311H and E430H and N434H, or T307H and Q311H and E430H and N434Y, or T307Q and Q311H and E430H and N434A, or T307Q and Q311H and E430H and N434H, or T307Q and Q311H and E430H and N434Y, or T307Q and V308P and N434Y and Y436H, or T307H and M252Y and S254T and T256E, or T307Q and M252Y and S254T and T256E, or Q311H and M252Y and S254T and T256E, or E430H and M252Y and S254T and T256E, or N434H and M252Y and S254T and T256E, or T307H and Q311H and M252Y and S254T and T256E, or T307H and E430H and M252Y and S254T and T256E, or T307H and N434A and M252Y and S254T and T256E, or T307H and N434H and M252Y and S254T and T256E, or T307Q and Q311H and M252Y and S254T and T256E, or T307Q and E430H and M252Y and S254T and T256E, or T307Q and N434H and M252Y and S254T and T256E, or T307H and Q311H and E430H and N434A and M252Y and S254T and T256E, or T307H and Q311H and E430H and N434H and M252Y and S254T and T256E, or T307H and Q311H and E430H and N434Y and M252Y and S254T and T256E, or T307Q and Q311H and E430H and N434A and M252Y and S254T and T256E, or T307Q and Q311H and E430H and N434H and M252Y and S254T and T256E, or T307Q and Q311H and E430H and N434Y and M252Y and S254T and T256E, or T307Q and V308P and N434Y and Y436H and M252Y and S254T and T256E.

12 Claims, 3 Drawing Sheets
Specification includes a Sequence Listing.

(52) U.S. Cl.
CPC ...... *C07K 2317/35* (2013.01); *C07K 2317/52* (2013.01); *C07K 2317/526* (2013.01); *C07K 2317/528* (2013.01); *C07K 2317/71* (2013.01); *C07K 2317/72* (2013.01); *C07K 2317/94* (2013.01)

(56) References Cited

U.S. PATENT DOCUMENTS

| | | | |
|---|---|---|---|
| 5,928,643 | A | 7/1999 | Wallner et al. |
| 8,969,526 | B2 | 3/2015 | Baehner et al. |
| 2004/0058394 | A1 | 3/2004 | Garber et al. |
| 2010/0111967 | A1* | 5/2010 | Baehner ................ C07K 16/22 424/158.1 |
| 2011/0111406 | A1 | 12/2011 | Igawa et al. |
| 2013/0084648 | A1 | 4/2013 | Bolton et al. |

FOREIGN PATENT DOCUMENTS

| | | | |
|---|---|---|---|
| JP | 2009-148265 | | 7/2009 |
| JP | 2017-104130 | | 6/2017 |
| WO | 9012803 | | 11/1990 |
| WO | 96/32478 | A1 | 10/1996 |
| WO | 99/62942 | | 12/1999 |
| WO | 02/83738 | | 10/2002 |
| WO | 2005/047327 | | 5/2005 |
| WO | 2005047327 | | 5/2005 |
| WO | 2006/031370 | A2 | 3/2006 |
| WO | 2006/121168 | A1 | 11/2006 |
| WO | 2008006899 | | 1/2008 |
| WO | 2008/103475 | A1 | 8/2008 |
| WO | 2008/143199 | | 11/2008 |
| WO | 2009/041643 | A1 | 4/2009 |
| WO | 2009/086320 | A1 | 7/2009 |
| WO | 2010048313 | | 4/2010 |
| WO | 2010/151792 | A1 | 12/2010 |
| WO | 2011/028952 | A1 | 3/2011 |
| WO | 2011/106272 | | 9/2011 |
| WO | 2011/122011 | | 10/2011 |
| WO | 2011/159877 | A2 | 12/2011 |
| WO | 2012/125850 | A1 | 9/2012 |
| WO | WO 2012/125850 | * | 9/2012 ............. C07K 16/00 |
| WO | 2013/087911 | A1 | 6/2013 |
| WO | 2013/120929 | A1 | 8/2013 |
| WO | 2014/006217 | A1 | 1/2014 |
| WO | 2014/006217 | A9 | 1/2014 |
| WO | 2014/131712 | A1 | 9/2014 |
| WO | 2014/177459 | A2 | 11/2014 |
| WO | 2014/177460 | A1 | 11/2014 |

OTHER PUBLICATIONS

Dall'Acqua et al., "Increasing the affinity of a human IgG1 for the neonatal Fc receptor: biological consequences" J Immunol 169(9):5171-5180 (Nov. 1, 2002).

Dall'Acqua et al., "Properties of human IgG1s engineered for enhanced binding to the neonatal Fc receptor (FcRn)" J Biol Chem 281(33):23514-23524 (Aug. 2006).

Firan et al., "The MHC class I-related receptor, FcRn, plays an essential role in the maternofetal transfer of γ-globulin in humans" InternationalImmunology 13(8):993-1002 (2001).

Huber et al., "Crystallization and stoichiometry of binding of a complex between a rat intestinal Fc receptor and Fc" J Mol Biol 230:1077-1083 (1993).

ISR for PCT/EP2015/075656 (dated May 11, 2016).

Kim et al., "Identifying Amino Acid Residues that Influence Plasma Clearance of Murine IgG1 Fragments by Site-Directed Mutagenesis." Eur J Immunol 24:542-548 (1994).

Kim et al., "Mapping the site on human IgG for binding of the MHC class I-related receptor, FcRn" Eur J Immunol 29(9):2819-2825 (Sep. 1999).

Kim, H. et al., "FcRn receptor-mediated pharmacokinetics of therapeutic IgG in the eye" Molecular Vision 15:2803-2812 (2009).

Kuo et al., "Neonatal Fc receptor: from immunity to therapeutics" J Clin Immunol 30:777-789 (2010).

Kuo, T.T. et al., "Neonatal Fc receptor and IgG-based therapeutic" mAbs 3(5):422-430 (2011).

Medesan et al., "Localization of the site of the IgG molecule that regulates maternofetal transmission in mice" Eur J Immunol 26(10):2533-2536 (Oct. 1996).

Medesan, C. et al., "Delineation of the Amino Acid Residues Involved in Transcytosis and Catabolism of Mouse 1gG1" The Journal of Immunology 158(5):2211-2217 (1997).

Monnet, C. et al., "Combined glyco-and protein-Fc engineering simultaneously enhance cytotoxicity and half-life of a therapeutic antibody" mAbs 6(2):422-436 (2014).

Roopenian et al., "FcRn: the neonatal Fc receptor comes of age" Nat Rev/Immunol 7:715-725 (Sep. 2007).

Shields et al., "High resolution mapping of the binding site on human IgG1 for Fc gamma RI, Fc gamma RII, Fc gamma RIII, and FcRn and design of IgG1 variants with improved binding to the Fc gamma R" J Biol Chem. 276(9):6591-6604 (2001).

Spassov, V.Z. et al., "pH-Selective mutagenesis of protein-protein interfaces: In silico design of therapeutic antibodies with prolonged half-life" Proteins Structure Function and Bioinformatics 81(4):704-714 (2013).

Yeung et al. et al., "A Therapeutic Anti-VEGF Antibody with Increased Potency Independent of Pharmacokinetic Half-life" Cancer Res 70(8):3269-3277 (2010).

Yeung Yik Andy et al., "Engineering Human IgG1 Affinity to Human Neonatal Fc Receptor: Impact of Affinity Improvement on Pharmacokinetics in Primates" The Journal of Immunology 182(12):7663-7671 (2009).

Written Opinion of the International Searching Authority issued in International Application No. PCT/EP2015/075656, dated as of the actual completion of the international search dated Dec. 21, 2015 in 10 pages.

Adamski et al., "Expression of the Fc receptor in the mammary gland during lactation in the marsupial Trichosurus vulpecula (brushtail possum)" Molecular Immunology 37:435-444 (2000).

Ahouse et al., "Mouse MHC class I-like Fc receptor encoded outside the MHC" Journal of Immunology 151:6076-6088 (1993).

Datta-Mannan et al., "FcRn Affinity-Pharmacokinetic Relationship of Five Human IgG4 Antibodies Engineered for Improved In Vitro FcRn Binding Properties in Cynomolgus Monkeys" Drug Metab Disp 40(8):1545-1555 (2012).

Josic & Lim, "Analytical and Preparative Methods for Purification of Antibodies," Food Technol. Biotechnol. 39 (2001) 215-226.

Kacskovics et al., "Cloning and Characterization of the Bovine MHC Class I-Like Fc Receptor" Journal of Immunology 164(4):1889-1897

Kacskovics et al., "Cloning and characterization of the dromedary (Camelus dromedarius) neonatal Fc receptor (drFcRn)" Developmental & Comparative Immunology 30(12):12034-1215.

Kandil et al., "Structural and phylogenetic analysis of the MHC class I-like Fc receptor gene" Journal of Immunology 154(11):5907-5918.

Martin et al., "Characterization of the 2:1 complex between the class I MHC-related Fc receptor and its Fc ligand in solutoin" Biochem 38:12639-12647 (1999).

Mayer et al., "Redistribution of the sheep neonatal Fc receptor in the mammary gland around the time of parturition in ewes and its localization in the small intestine of neonatal lambs" Journal of Immunology 107(3):288-296.

Raghavan et al., "Effects of receptor dimerization on the interaction between the class I major histocompatibility complex-related Fc receptor and IgG" PNAS 92(24):11200-11204 (1995).

Schlothauer, T., et al., "Analytical FcRn affinity chromatography for functional characterization of monoclonal antibodies" mAbs 5(4):576-586 (2013).

Schnulle et al., "Sequence and expression of the FcRn in the porcine mammary gland" Veterinary Immunology and Immunopathology 91(3-4):227-231.

Simister and Mostov, "An Fc receptor structurally related to MHC class I antigens" Nature 337:184-187 (1989).

(56) References Cited

OTHER PUBLICATIONS

Story et al., "A major histocompatibility complex class I-like Fc receptor cloned from human placenta: possible role in transfer of immunoglobulin G from mother to fetus," Journal of Experimental Medicine, 180(6): 2377-2381 (1984).
Vaccaro et al., "Engineering the Fc region of immunoglobulin G to modulate in vivo antibody levels" Nature Biotechnology 23(10):1283-1288 ( 2005).
Vaughn et al., "High-Affinity Binding of the Neonatal Fc Receptor to Its IgG Ligand Requires Receptor Immobilization" Biochemistry 36(31):9374-9380 ( 1997).
Wang, W. et al., "Monoclonal Antibodies with Identical Fc Sequences Can Bind to FcRn Differentially with Pharmacokinetic Consequences" Drug Metabolism and Disposition 39(9):1469-1477 ( 2011).
Akilesh et al., "Neonatal FcR Expression in Bone Marrow-Derived Cells Functions to Protect Serum IgG from Catabolisml" J Immunol 179:4580-4588 (2007).
Armour et al., "Recombinant human IgG molecules lacking Fcÿ receptor I binding and monocyte triggering activities" Eur. J. Immunol. 29:2613-2634 (May 10, 1999).
Benson, J.M. et al., "Discovery and mechanism of ustekinumab: A human monoclonal antibody targeting interleukin-12 and interleukin-23 for treatment of immune-mediated disorders" mAbs 3:535-545(2011).
Boswell et al., "Effects of Charge on Antibody Tissue Distribution and Pharmacokineties" Bioconjugate Chem. 21:2153-2163 (2010).
Brambell et al. et al., "A Theoretical Model of γ-Globulin Catabolism" NATURE 203:1352-1354 (1964).
Brambell et al., "Nutrition of the foetus and the newly born" Proc. Nutr. Soc 28:35-41 (1969).
Chaudhury et al., "The Major Histocompatibility Complex—related Fc Receptor for IgG (FcRn) Binds Albumin and Prolongs Its Lifespan" J. EXP. MED. 197:315-322 (2003).
International Search Report and Written Opinion of the International Searching Authority on patentatibility for International Patent Application No. PCT/EP2015/055482. (dated Jun. 5, 2015).
Cui et al., "Chemically Programmed Bispecific Antibodies That Recruit and Activate T Cells" Journal of Biological Chemistry 287 (34):28206-28214 (2012).
Ding et al., "ABT-874, a fully human monoclonal anti-IL-12/IL-23 antibody for the potential treatment of autoimmune diseases" Curr. Opin. Investig. Drugs 9:515-522 (2008).
Edelman et al., "Antibody structure and molecular immunology" J Immunol 34: 1-22 (1991).
Faber et al., "Three-dimensional structure of a human Fab with high affinity for tetanus toxoidl" Immunotechnology 3:253-270 (1998).
Gandhi et al., "Anti-p40 antibodies ustekinumab and briakinumab: blockade of interleukin-12 and interleukin-23 in the treatment of psoriasis" Semin. Cutan. Med. Surg. 29:48-52 (2010).
Garcia-Bennett et al., "In search of the Holy Grail: Folate-targeted nanoparticles for cancer therapy" Biochem Pharma 81:976-984 (2011).
Ghetie and Ward, "Multiple Roles for the Major Histoeompatibility Complex Class I-Related Receptor FcRn" ANN REV IMMUNOL 18:739-766 (2000).
Goebl et al., "Neonatal Fc Receptor Mediates Internalization of Fc in Transfected Human Endothelial Cells" Mol. Biol. Cell 19:5490-5505 (2008).
Hess et al., "GROMACS 4: Algorithms for Highly Efficient, Loas-Balanced, and Scalable Molecular Simulation" J. Chem. Theory Comput. 4:435-447 (2008).
Igawa et al., "Reduced elimination of IgG antibodies by engineering the variable region" Protein Engineering, Design & Selection 23(5):385-392 (2010).
Jorgensen et al., "Development and Testing of the OPLS All-Atom Force Field on Conformational Energicts and Properties of Organic Liquids" J. Am. Chem. Soc. 118:11225-11236(1996).
Josie et al., "Analytical and Preparative Methods for Putifieation of Antibodies," Food technol. biotechnol., 39 (3), pp. 215-226, 2001.

Kacskovics et al., "Cloning and Characterization of the Bovine MHC Class I-Like Fc Receptor" Journal of Immunology 164(4):1889-1897 (2000).
Khawli et al., "Pharmacokinetic characteristics and biodistribution of radioiodinated chimeric TNT-1, -2, and -3 monoclonal antibodies after chemical modification with biotin" Cancer Biother Radiopharm 17(4):359-370 (2002).
Kim et al., "Identifying amino acid residues that influence plasma clearance of murine IgG1 fragments by site-directed mutagenesis," Eur. J. Immunol. 24 (1994) 542-548.
Kopantzev et al., "Differences in gene expression levels between early and later stages of human lung development are opposite to those between normal lung tissue and non-small lung cell carcinoma" Lung Cancer 62(1):22-34 (2008).
Kortkhonjia et al., "Probing antibody internal dynamics with fluorescence anisotropy and molecular dynamics simulations" mAbs 5:306-322 (2013).
Kortt et al., "Single-chain Fv fragments of anti-neuraminidase antibody NC10 containing five-and ten-residue linkers form dimers and with zero-residue linker a trimer" PROTEIN ENG 10(4):423-433 (Apr. 1997).
Li et al., "DelPhi: a comprehensive suite for DelPhi software and associated resources" BMC. Biophys. 5(9) (2012).
Li et al., "Framework Selection Can Influence Pharmacokinetics of a Humanized Therapeutic Antibody Through Differences in Molecule Charge" mAbs 6(5):1255-1264 (2014).
Lima et al., "Expert Opinion on Biological Therapy, Briakinumab" Expert. Opin. Biol. Ther. 9:1107-1113 (2009).
Luo et al., "Structural Basis for the Dual Recognition of IL-12 and IL-23 by Ustekinumab" J. Mol. Biol. 402:797-812. (2010).
Magistrelli et al., "Robust recombinant FcRn production in mammalian cells enabling oriented immobilization for IgG binding studies," Journal of Immunological Methods, Vol. 375, Issues 1-2, Jan. 31, 2012, pp. 20-29.
Martin et al., "Crystal structure at 2.8 A of an FcRn/heterodimeric Fc complex: mechanism of pH-dependent binding" MOL CELL 7(4):867-877 (Apr. 2001).
Montoyo et al., "Conditional deletion of the MHC class I-related receptor FeRn reveals the sites of IgG homeostasis in mice" PNAS 106:2788-2793 (2009).
Ober et al., "Exocytosis of IgG as mediated by the receptor, FcRn: an Analysis at the Single-Molecule Level" Proc Natl Acad Sci U.S.A. 101(30):11076-11081. (Jul. 2004).
Ober et al., "Visualizing the Site and Dynamics of IgG Salvage by the MHC Class I-Related Receptor, FeRnl" J Immunol 172:2021-2029 (2004).
Olafsen, T. Antibody Engineering—Methods in Molecular Biology "Fc Engineering: Serum Half-Life Modulation Through FcRn Binding"Humana Press,:537-556 (2012).
Pan et al., "Methionine oxidation in human IgG2 Fc decreases binding affinities to protein A and FcRn," Protein Sci. Feb. 2009;18(2):424-433.
Petkova et al., "Enhanced half-life of genetically engineered human IgG1 antibodies in a humanized FcRn mouse model: potential application in humorally mediated autoimmune disease" International Immunology, 18:1759-1769 (2006).
"pH Gradient Elution for Improved Separation of Monoclonal Antibody Charge Variants" Agilent Technologies, Inc. (JP version only), (Dec. 16, 2011).
Popov et al., "The stoichiometry and affinity of the interaction of murine Fc fragments with the MHC class I-related receptor, FcRn," Mol. Immunol. 33 (1996), pp. 521-530.
Prabhat et al., "Elucidation of intracelluar recycling pathways leading to exocytosis of the Fc receptor, FcRn, by using multifocal plane microscopy" Proc Natl Aca Sci U.S.A.104(14):5889-5894 (Apr. 2007).
Putnam et al., "Pharmacokinetie, pharmacodynamie and immunogenicity comparability assessment strategies for monoclonal antibodies" TRENDS BIOTECHNOL 28:509-516 (2010).
Reff et al., "A review of modifications to recombinant antibodies: attempt to increase efficacy in oncology applications" Crit. Rev. Oncol. Hematol 40:25-35 (2001).

(56) References Cited

OTHER PUBLICATIONS

Rodewald et al., "ph-dependent binding of immunoglobulins to intestinal cells of the neonatal rat" J Cell Biol 71:666-669 (Nov. 1976).
Roopenian and Akilesh, "FcRn: the neonatal Fc receptor comes of age" NAT REV IMMUNOL 7:715-725 (2007).
Roopenian et al., "The MHC Class I-like IgG receptor controls perinatal IgG transport, IgG homestasis, and fate of IgG fc-copled drugs" J Immuno. 170(7):3528-3533 (Apr. 2003).
Ropeenian, "Human FcRn Transgenic Mice for Pharmacokinetic Evaluation of Therapeutic Antibodies" Methods Mol. Biol. 602:93-104 (2010).
Sampei et al., "Identification and multidimensional optimization of an asymmetric bispecific IgG antibody mimicking the function of factor VIII cofactor activity" PLOS ONE 8(2):e57479 (2013).
Sanchez et al., "Stoichiometry of the Interaction between the Major Histocompatibility Complex-Related Fc Receptor and Its Fc Ligand" Biochemistry 38:9471-9476 (1999).
Shields, R., et al., "High resolution mapping of the binding site on human IgG1 for Fc gamma RI, Fc gamma RII, Fc gamma RIII, and FcRn and design of IgG1 variants with improved binding to the Fc gamma R" J BIOL CHEM 276(9):6591-6604 (Mar. 2, 2001).
Suzuki, et al., "Importance of Neonatal FcR in Regulating the Serum Half-Life of Therapeutic Proteins Containing the Fc Domain of Human IgG1: A Comparative Study of the Affinity of Monoclonal Antibodies and Fc-Fusion Proteins to Human Neonatal FcR" J Immunol 184:1968-1976 (2010).
The Chinese Office Action, dated Jun. 23, 2015, in the related Chinese patent application No. 201380009724.6.
The European extended search report, dated Nov. 7, 2012, in the related European patent application No. 12155630.2.
The International Search Report and Written Opinion, dated Jul. 10, 2013, in the related PCT Application No. PCT/EP13/52932.
Topalian et al., "Safety, Activity, and Immune Correlates of Anti-PD-1 Antibody in Cancer" N Engl J Med 366(26):2443-2454 (2012).
Traezewski and Rudnicka, "Briakinumab for the Treatment of Plaque Psoriasis" BioDrugs 26:9-20 (2012).
Turkova, "Affinity Chromatography" Journal of Chromatography Library (including English translation), 12:89 (1978).
Vaccaro et al., "Engineering the Fc region of immunoglobulin G to modulate in vivo antibody levels" Nature Biotechnology 23:1283-1288 (2005).
Waldmann and Strober, "Metabolism of Immunoglobulins" Prog. Allergy 13:1-110 (1969).
Weber and Keam, "Ustekinumab: Adis Drug Profile" BioDrugs 23:53-61 (2009).
Weger et al, "Current status and new developments in the treatment of psoriasis and psoriatic arthritis with biological agents" BJP 160:810-820 (2010).
Zalevsky et al., "Enhanced antibody half-life improves in vivo activity" Nat. Biotechnol 28:157-159 (2010).
Zhu et al., "Population Pharmacokinetic Modeling of Ustekinumab, a Human Monoclonal Antibody Targeting IL-12/23p40, in Patients With Moderate to Severe Plaque Psoriasis" J. Clin. Pharmacol. 49:162-175 (2009).

\* cited by examiner

FC-REGION VARIANTS WITH MODIFIED FCRN-BINDING AND METHODS OF USE

CROSS REFERENCE TO RELATED APPLICATIONS

This application is a continuation of International Application Number PCT/EP2015/075656, filed Nov. 4, 2015, the entire contents of which are incorporated herein by reference, and which claims benefit under 35 U.S.C. § 119 to European Application Number 14192052.0, filed Nov. 6, 2014.

SEQUENCE LISTING

This application hereby incorporates by reference the material of the electronic Sequence Listing filed concurrently herewith. The material in the electronic Sequence Listing is submitted as a text (.txt) file entitled P32408_US_ST25.txt created on May 3, 2017 which has a file size of 58.0 KB, and is herein incorporated by reference in its entirely.

FIELD OF THE INVENTION

The present invention relates to antibodies and Fc-region fusion polypeptides which are asymmetrically modified with respect to their Fc-receptor, especially their FcRn, interaction and methods of using the same.

BACKGROUND

The neonatal Fc-receptor (FcRn) is important for the metabolic fate of antibodies of the IgG class in vivo. The FcRn functions to salvage IgG from the lysosomal degradation pathway, resulting in reduced clearance and increased half-life. It is a heterodimeric protein consisting of two polypeptides: a 50 kDa class I major histocompatibility complex-like protein (α-FcRn) and a 15 kDa β2-microglobulin (β2m). FcRn binds with high affinity to the CH2-CH3 portion of the Fc-region of an antibody of the class IgG. The interaction between an antibody of the class IgG and the FcRn is pH dependent and occurs in a 1:2 stoichiometry, i.e. one IgG antibody molecule can interact with two FcRn molecules via its two heavy chain Fc-region polypeptides (see e.g. Huber, A. H., et al., J. Mol. Biol. 230 (1993) 1077-1083).

Thus, an IgGs in vitro FcRn binding properties/characteristics are indicative of its in vivo pharmacokinetic properties in the blood circulation.

In the interaction between the FcRn and the Fc-region of an antibody of the IgG class different amino acid residues of the heavy chain CH2- and CH3-domain are participating.

Different mutations that influence the FcRn binding and therewith the half-live in the blood circulation are known. Fc-region residues critical to the mouse Fc-region-mouse FcRn interaction have been identified by site-directed mutagenesis (see e.g. Dall'Acqua, W. F., et al. J. Immunol 169 (2002) 5171-5180). Residues I253, H310, H433, N434, and H435 (numbering according to Kabat EU index numbering system) are involved in the interaction (Medesan, C., et al., Eur. J. Immunol. 26 (1996) 2533-2536; Firan, M., et al., Int. Immunol. 13 (2001) 993-1002; Kim, J. K., et al., Eur. J. Immunol. 24 (1994) 542-548). Residues I253, H310, and H435 were found to be critical for the interaction of human Fc-region with murine FcRn (Kim, J. K., et al., Eur. J. Immunol. 29 (1999) 2819-2885).

Methods to increase Fc-region (and likewise IgG) binding to FcRn have been performed by mutating various amino acid residues in the Fc-region: Thr 250, Met 252, Ser 254, Thr 256, Thr 307, Glu 380, Met 428, His 433, and Asn 434 (see Kuo, T. T., et al., J. Clin. Immunol. 30 (2010) 777-789; Ropeenian, D. C., et al., Nat. Rev. Immunol. 7 (2007) 715-725).

The combination of the mutations M252Y, S254T, T256E have been described by Dall'Acqua et al. to improve FcRn binding by protein-protein interaction studies (Dall'Acqua, W. F., et al. J. Biol. Chem. 281 (2006) 23514-23524). Studies of the human Fc-region-human FcRn complex have shown that residues I253, S254, H435, and Y436 are crucial for the interaction (Firan, M., et al., Int. Immunol. 13 (2001) 993-1002; Shields, R. L., et al., J. Biol. Chem. 276 (2001) 6591-6604). In Yeung, Y. A., et al. (J. Immunol. 182 (2009) 7667-7671) various mutants of residues 248 to 259 and 301 to 317 and 376 to 382 and 424 to 437 have been reported and examined.

SUMMARY

It has been found that the FcRn-binding of an antibody or Fc-region fusion polypeptide can be modified by altering amino acid residues at non-corresponding positions in the individual Fc-region polypeptides as these alterations act together in the modification of the FcRn-binding. Antibodies and Fc-region fusion polypeptides as reported herein are useful, e.g., for the treatment of diseases in which tailor-made systemic retention times are required.

Herein are reported variant Fc-regions that have modified FcRn binding properties compared to a corresponding wild-type Fc-region. These variant Fc-regions contain specific amino acid mutations in the CH2- and/or CH3-domain. It has been found that these mutations when used either alone or in combination in the same or distributed in both heavy chains of an Fc-region allow to tailor-design the in vivo half-live of the variant Fc-region.

One aspect as reported herein is a variant (human) IgG class Fc-region comprising a first Fc-region polypeptide and a second Fc-region polypeptide,
  wherein
  a) the first Fc-region polypeptide and the second Fc-region polypeptide are derived from the same parent (human) IgG class Fc-region polypeptide, and
  b) the first Fc-region polypeptide has an amino acid sequence that differs from the second Fc-region polypeptide amino acid sequence at least at one corresponding position according to the Kabat EU index numbering system,
  whereby the variant (human) IgG class Fc-region has a different affinity to a human Fc-receptor compared to a (human) IgG class Fc-region that has the same amino acid residues (as the (parent) human Fc-region polypeptide of a)) at corresponding positions according to the Kabat EU index numbering system in the first Fc-region polypeptide and the second Fc-region polypeptide.

One aspect as reported herein is a variant (human) IgG class Fc-region comprising a first Fc-region polypeptide and a second Fc-region polypeptide,
  wherein
  a) the first Fc-region polypeptide has an amino acid sequence that differs from the second Fc-region polypeptide amino acid sequence at least at one corresponding position according to the Kabat EU index numbering system, whereby the variant (human) IgG class Fc-region has a different affinity to a human Fc-receptor compared to an IgG class Fc-region that has the same amino acid residue (as in a corresponding human Fc-region) in the first and the second Fc-region polypeptide at the corresponding position.

One aspect as reported herein is a variant (human) IgG class Fc-region comprising a first Fc-region polypeptide and a second Fc-region polypeptide,
wherein
a) the amino acid sequence of the first Fc-region polypeptide differs from the amino acid sequence of a first parent IgG class Fc-region polypeptide in one or more amino acid residues,
and
the amino acid sequence of the second Fc-region polypeptide differs from the amino acid sequence of a second parent IgG class Fc-region polypeptide in one or more amino acid residues, and
b) the first Fc-region polypeptide has an amino acid sequence that differs from the second Fc-region polypeptide amino acid sequence at least at one corresponding position according to the Kabat EU index numbering system,
whereby the variant (human) IgG class Fc-region has a different affinity to a human Fc-receptor compared to a parent IgG class Fc-region comprising the first and the second parent IgG class Fc-region polypeptide of a).

One aspect as reported herein is a variant (human) IgG class Fc-region comprising a first Fc-region polypeptide and a second Fc-region polypeptide,
wherein
a) the amino acid sequence of the first Fc-region polypeptide is derived from a first parent IgG class Fc-region polypeptide and the amino acid sequence of the second Fc-region polypeptide is derived from a second parent IgG class Fc-region polypeptide, and
b) in the first Fc-region polypeptide and/or in the second Fc-region polypeptide one or more mutations are introduced so that the first Fc-region polypeptide has an amino acid sequence that differs from the second Fc-region polypeptide amino acid sequence at least at one corresponding position according to the Kabat EU index numbering system,
whereby the variant (human) IgG class Fc-region has a different affinity to a human Fc-receptor compared to an IgG class Fc-region comprising the first and the second parent IgG class Fc-region polypeptide of a).

In one embodiment of all aspects the variant (human) IgG class Fc-region is a variant (human) IgG class heterodimeric Fc-region.

In one embodiment of all aspects the first parent IgG class Fc-region polypeptide and the second parent IgG class Fc-region polypeptide are non-human IgG class Fc-region polypeptides.

In one embodiment of all aspects the first parent IgG class Fc-region polypeptide and the second parent IgG class Fc-region polypeptide are the same IgG class Fc-region polypeptide.

In one embodiment of all aspects the pairing of the first Fc-region polypeptide and the second Fc-region polypeptide to form a dimeric (functional) Fc-region results in the formation of a heterodimer.

In one embodiment of all aspects the first and the second Fc-region polypeptide differ independently of each other in at least one amino acid residue from the respective parent IgG class Fc-region polypeptide.

In one embodiment of all aspects the IgG class is selected from the subclasses IgG1, IgG2, IgG3 and IgG4.

In one embodiment of all aspects the human Fc-receptor is selected from the human neonatal Fc-receptor and the human Fcγ receptor.

In one embodiment of all aspects the first Fc-region polypeptide differs in 1 or 2 or 3 or 4 or 5 or 6 or 7 or 8 or 9 or 10 or 11 or 12 amino acid residues at corresponding position according to the Kabat EU index numbering system from the second Fc-region polypeptide.

In one embodiment of all aspects as reported herein either the first Fc-region polypeptide or the second Fc-region polypeptide or both Fc-region polypeptides comprise one of the following mutations or combination of mutations:
T307H, or
Q311H, or
E430 H, or
N434H, or
T307H and Q311H, or
T307H and E430H, or
T307H and N434A, or
T307H and N434H, or
T307Q and Q311H, or
T307Q and E430H, or
T307Q and N434H, or
T307H and Q311H and E430H and N434A, or
T307H and Q311H and E430H and N434H, or
T307H and Q311H and E430H and N434Y, or
T307Q and Q311H and E430H and N434A, or
T307Q and Q311H and E430H and N434H, or
T307Q and Q311H and E430H and N434Y, or
T307Q and V308P and N434Y and Y436H, or
T307H and M252Y and S254T and T256E, or
T307Q and M252Y and S254T and T256E, or
Q311H and M252Y and S254T and T256E, or
E430 H and M252Y and S254T and T256E, or
N434H and M252Y and S254T and T256E, or
T307H and Q311H and M252Y and S254T and T256E, or
T307H and E430H and M252Y and S254T and T256E, or
T307H and N434A and M252Y and S254T and T256E, or
T307H and N434H and M252Y and S254T and T256E, or
T307Q and Q311H and M252Y and S254T and T256E, or
T307Q and E430H and M252Y and S254T and T256E, or
T307Q and N434H and M252Y and S254T and T256E, or
T307H and Q311H and E430H and N434A and M252Y and S254T and T256E, or
T307H and Q311H and E430H and N434H and M252Y and S254T and T256E, or
T307H and Q311H and E430H and N434Y and M252Y and S254T and T256E, or
T307Q and Q311H and E430H and N434A and M252Y and S254T and T256E, or
T307Q and Q311H and E430H and N434H and M252Y and S254T and T256E, or
T307Q and Q311H and E430H and N434Y and M252Y and S254T and T256E, or
T307Q and V308P and N434Y and Y436H and M252Y and S254T and T256E.

In one embodiment of all aspects as reported herein either the first Fc-region polypeptide or the second Fc-region polypeptide or both Fc-region polypeptides comprise one of the following mutations or combination of mutations:
T307H, or
E430 H, or
T307H and Q311H, or
T307H and E430H, or
T307H and N434A, or T307H and N434H, or
T307Q and Q311H, or
T307Q and E430H, or
T307Q and N434H, or
T307H and Q311H and E430H and N434A, or
T307H and Q311H and E430H and N434H, or
T307H and Q311H and E430H and N434Y, or
T307Q and Q311H and E430H and N434A, or
T307Q and Q311H and E430H and N434H, or
T307Q and Q311H and E430H and N434Y, or
T307Q and V308P and N434Y and Y436H, or
T307H and M252Y and S254T and T256E, or
T307Q and M252Y and S254T and T256E, or
Q311H and M252Y and S254T and T256E, or
E430 H and M252Y and S254T and T256E, or
N434H and M252Y and S254T and T256E, or
T307H and Q311H and M252Y and S254T and T256E, or
T307H and E430H and M252Y and S254T and T256E, or
T307H and N434A and M252Y and S254T and T256E, or
T307H and N434H and M252Y and S254T and T256E, or
T307Q and Q311H and M252Y and S254T and T256E, or
T307Q and E430H and M252Y and S254T and T256E, or
T307Q and N434H and M252Y and S254T and T256E, or
T307H and Q311H and E430H and N434A and M252Y and S254T and T256E, or
T307H and Q311H and E430H and N434H and M252Y and S254T and T256E, or
T307H and Q311H and E430H and N434Y and M252Y and S254T and T256E, or
T307Q and Q311H and E430H and N434A and M252Y and S254T and T256E, or
T307Q and Q311H and E430H and N434H and M252Y and S254T and T256E, or
T307Q and Q311H and E430H and N434Y and M252Y and S254T and T256E, or
T307Q and V308P and N434Y and Y436H and M252Y and S254T and T256E.

In one embodiment of all aspects as reported herein
the first Fc-region polypeptide comprise independently of the second Fc-region polypeptide one of the following mutations or combination of mutations:
T307H, or
Q311H, or
E430 H, or
N434H, or
T307H and Q311H, or
T307H and E430H, or
T307H and N434A, or
T307H and N434H, or
T307Q and Q311H, or
T307Q and E430H, or
T307Q and N434H, or
M252Y and S254T and T256E, or
I253A and H310A and H435A, or
H310A and H433A and Y436A, or
T307H and Q311H and E430H and N434A, or
T307H and Q311H and E430H and N434H, or
T307H and Q311H and E430H and N434Y, or
T307Q and Q311H and E430H and N434A, or
T307Q and Q311H and E430H and N434H, or
T307Q and Q311H and E430H and N434Y, or
T307Q and V308P and N434Y and Y436H, or
T307H and M252Y and S254T and T256E, or
Q311H and M252Y and S254T and T256E, or
E430 H and M252Y and S254T and T256E, or
N434H and M252Y and S254T and T256E, or
T307H and Q311H and M252Y and S254T and T256E, or
T307H and E430H and M252Y and S254T and T256E, or
T307H and N434A and M252Y and S254T and T256E, or
T307H and N434H and M252Y and S254T and T256E, or
T307Q and Q311H and M252Y and S254T and T256E, or
T307Q and E430H and M252Y and S254T and T256E, or
T307Q and N434H and M252Y and S254T and T256E, or
T307H and Q311H and E430H and N434A and M252Y and S254T and T256E, or
T307H and Q311H and E430H and N434H and M252Y and S254T and T256E, or
T307H and Q311H and E430H and N434Y and M252Y and S254T and T256E, or
T307Q and V308P and N434Y and Y436H and M252Y and S254T and T256E, or
T307Q and V308P and N434Y and Y436H and M252Y and S254T and T256E,
and
the second Fc-region polypeptide comprise independently of the first Fc-region polypeptide one of the following mutations or combination of mutations
T307H, or
T307Q, or
Q311H, or
E430 H, or
N434H, or
T307H and Q311H, or
T307H and E430H, or
T307H and N434A, or
T307H and N434H, or
T307Q and Q311H, or
T307Q and E430H, or
T307Q and N434H, or
T307H and Q311H and E430H and N434A, or
T307H and Q311H and E430H and N434H, or
T307H and Q311H and E430H and N434Y, or
T307Q and Q311H and E430H and N434A, or
T307Q and Q311H and E430H and N434H, or
T307Q and Q311H and E430H and N434Y, or
T307Q and V308P and N434Y and Y436H, or
T307H and M252Y and S254T and T256E, or
Q311H and M252Y and S254T and T256E, or
E430 H and M252Y and S254T and T256E, or
N434H and M252Y and S254T and T256E.

In one embodiment of all aspects as reported herein
the first Fc-region polypeptide comprise independently of the second Fc-region polypeptide one of the following mutations or combination of mutations:
T307H, or
E430 H, or
T307H and Q311H, or
T307H and E430H, or
T307H and N434A, or
T307H and N434H, or
T307Q and Q311H, or
T307Q and E430H, or
T307Q and N434H, or
M252Y and S254T and T256E, or
I253A and H310A and H435A, or
H310A and H433A and Y436A, or T307H and Q311H and E430H and N434A, or
T307H and Q311H and E430H and N434H, or
T307H and Q311H and E430H and N434Y, or
T307Q and Q311H and E430H and N434A, or
T307Q and Q311H and E430H and N434H, or
T307Q and Q311H and E430H and N434Y, or
T307Q and V308P and N434Y and Y436H, or
T307H and M252Y and S254T and T256E, or
Q311H and M252Y and S254T and T256E, or
E430 H and M252Y and S254T and T256E, or
N434H and M252Y and S254T and T256E, or
T307H and Q311H and M252Y and S254T and T256E, or
T307H and E430H and M252Y and S254T and T256E, or
T307H and N434A and M252Y and S254T and T256E, or
T307H and N434H and M252Y and S254T and T256E, or
T307Q and Q311H and M252Y and S254T and T256E, or
T307Q and E430H and M252Y and S254T and T256E, or
T307Q and N434H and M252Y and S254T and T256E, or
T307H and Q311H and E430H and N434A and M252Y and S254T and T256E, or
T307H and Q311H and E430H and N434H and M252Y and S254T and T256E, or
T307H and Q311H and E430H and N434Y and M252Y and S254T and T256E, or
T307Q and V308P and N434Y and Y436H and M252Y and S254T and T256E, or
T307Q and V308P and N434Y and Y436H and M252Y and S254T and T256E,
and
the second Fc-region polypeptide comprise independently of the first Fc-region polypeptide one of the following mutations or combination of mutations
T307H, or
T307Q, or
E430 H, or
T307H and Q311H, or
T307H and E430H, or
T307H and N434A, or
T307H and N434H, or
T307Q and Q311H, or
T307Q and E430H, or
T307Q and N434H, or
T307H and Q311H and E430H and N434A, or
T307H and Q311H and E430H and N434H, or
T307H and Q311H and E430H and N434Y, or
T307Q and Q311H and E430H and N434A, or
T307Q and Q311H and E430H and N434H, or
T307Q and Q311H and E430H and N434Y, or
T307Q and V308P and N434Y and Y436H, or
T307H and M252Y and S254T and T256E, or
Q311H and M252Y and S254T and T256E, or
E430 H and M252Y and S254T and T256E, or
N434H and M252Y and S254T and T256E.

In one embodiment of all aspects as reported herein the first Fc-region polypeptide comprises
one of the following combinations of mutations:
none, or
M252Y and S254T and T256E, or
I253A and H310A and H435A, or
H310A and H433A and Y436A,
and
one of the following mutations or combination of mutations:
none
T307H, or
T307Q, or
Q311H, or
E430 H, or
N434H, or
T307H and Q311H, or
T307H and E430H, or
T307H and N434A, or
T307H and N434H, or
T307Q and Q311H, or
T307Q and E430H, or
T307Q and N434H, or
T307Q and N434A, or
T307H and Q311H and E430H and N434A, or
T307H and Q311H and E430H and N434H, or
T307H and Q311H and E430H and N434Y, or
T307Q and Q311H and E430H and N434A, or
T307Q and Q311H and E430H and N434H, or
T307Q and Q311H and E430H and N434Y, or
T307Q and V308P and N434Y and Y436H,
and the second Fc-region polypeptide comprises
one of the following mutations or combination of mutations:
none, if the first Fc-region polypeptide comprises at least one mutation, or
T307H, or
T307Q, if the first Fc-region polypeptide does not comprises solely the T307Q mutation, or
Q311H, or
E430 H, or
N434H, or
T307H and Q311H, or
T307H and E430H, or
T307H and N434A, or
T307H and N434H, or
T307Q and Q311H, or
T307Q and E430H, or
T307Q and N434H, or
T307Q and N434A, or
M252Y and S254T and T256E, if the first Fc-region polypeptide does not comprises solely the combination M252Y and S254T and T256E of mutations, or
I253A and H310A and H435A, if the first Fc-region polypeptide does not comprises solely the combination I253A and H310A and H435A of mutations, or
H310A and H433A and Y436A, if the first Fc-region polypeptide does not comprises solely the combination H310A and H433A and Y436A of mutations, or
T307H and Q311H and E430H and N434A, or
T307H and Q311H and E430H and N434H, or
T307H and Q311H and E430H and N434Y, or
T307Q and Q311H and E430H and N434A, or
T307Q and Q311H and E430H and N434H, or
T307Q and Q311H and E430H and N434Y, or
T307Q and V308P and N434Y and Y436H.

In one embodiment of all aspects as reported herein the first Fc-region polypeptide comprises
one of the following combinations of mutations:
none, or
M252Y and S254T and T256E, or
I253A and H310A and H435A, or
H310A and H433A and Y436A, and
one of the following mutations or combination of mutations:
  none
  T307H, or
  T307Q, or
  E430 H, or
  T307H and Q311H, or
  T307H and E430H, or
  T307H and N434A, or
  T307H and N434H, or
  T307Q and Q311H, or
  T307Q and E430H, or
  T307Q and N434H, or
  T307Q and N434A, or
  T307H and Q311H and E430H and N434A, or
  T307H and Q311H and E430H and N434H, or
  T307H and Q311H and E430H and N434Y, or
  T307Q and Q311H and E430H and N434A, or
  T307Q and Q311H and E430H and N434H, or
  T307Q and Q311H and E430H and N434Y, or
  T307Q and V308P and N434Y and Y436H,
and the second Fc-region polypeptide comprises
one of the following mutations or combination of mutations:
  none, if the first Fc-region polypeptide comprises at least one mutation, or
  T307H, or
  T307Q, if the first Fc-region polypeptide does not comprises solely the T307Q mutation, or
  E430 H, or
  T307H and Q311H, or
  T307H and E430H, or
  T307H and N434A, or
  T307H and N434H, or
  T307Q and Q311H, or
  T307Q and E430H, or
  T307Q and N434H, or
  T307Q and N434A, or
  M252Y and S254T and T256E, if the first Fc-region polypeptide does not comprises solely the combination M252Y and S254T and T256E of mutations, or
  I253A and H310A and H435A, if the first Fc-region polypeptide does not comprises solely the combination I253A and H310A and H435A of mutations, or
  H310A and H433A and Y436A, if the first Fc-region polypeptide does not comprises solely the combination H310A and H433A and Y436A of mutations, or
  T307H and Q311H and E430H and N434A, or
  T307H and Q311H and E430H and N434H, or
  T307H and Q311H and E430H and N434Y, or
  T307Q and Q311H and E430H and N434A, or
  T307Q and Q311H and E430H and N434H, or
  T307Q and Q311H and E430H and N434Y, or
  T307Q and V308P and N434Y and Y436H.

In one preferred embodiment the first Fc-region polypeptide comprises the mutations I253A and H310A and H435A and the second Fc-region polypeptide comprises the mutations M252Y and S254T and T256E.

In one preferred embodiment the first Fc-region polypeptide comprises the mutations I253A and H310A and H435A and the second Fc-region polypeptide comprises the mutations M252Y and S254T and T256E and T307Q and N434Y.

In one preferred embodiment the first Fc-region polypeptide comprises the mutations I253A and H310A and H435A and the second Fc-region polypeptide comprises the mutations M252Y and S254T and T256E and T307Q and V308P and N434Y and Y436H.

In one preferred embodiment the first Fc-region polypeptide comprises the mutations T307H and Q311H and E430H and N434H and the second Fc-region polypeptide comprises the mutations M252Y and S254T and T256E.

In one preferred embodiment the first Fc-region polypeptide comprises the mutations T307H and N434H and the second Fc-region polypeptide comprises the mutations M252Y and S254T and T256E.

In one preferred embodiment the first Fc-region polypeptide comprises the mutations T307Q and N434A and the second Fc-region polypeptide comprises the mutations M252Y and S254T and T256E.

In one preferred embodiment the first Fc-region polypeptide comprises the mutations T250Q and M428L and the second Fc-region polypeptide comprises the mutations M252Y and S254T and T256E.

In one preferred embodiment the first Fc-region polypeptide comprises the mutations T307Q and N434H and the second Fc-region polypeptide comprises the mutations M252Y and S254T and T256E and T307Q and N434H.

In one preferred embodiment the first Fc-region polypeptide comprises the mutations T307H and Q311H and E430H and N434H and the second Fc-region polypeptide comprises the mutations T307H and Q311H and E430H and N434H.

In one preferred embodiment the first Fc-region polypeptide comprises the mutations T307H and N434H and the second Fc-region polypeptide comprises the mutations T307H and N434H.

In one preferred embodiment the first Fc-region polypeptide comprises the mutations T307H and N434H and M252Y and S254T and T256E and the second Fc-region polypeptide comprises the mutations T307H and N434H and M252Y and S254T and T256E.

In one preferred embodiment the first Fc-region polypeptide comprises the mutation N434H and the second Fc-region polypeptide comprises the mutation N434H.

In one preferred embodiment the first Fc-region polypeptide comprises the mutations T307Q and N434A.

In one preferred embodiment the first Fc-region polypeptide comprises the mutations T307H and N434H.

In one preferred embodiment the first Fc-region polypeptide comprises the mutations T307H and N434H and M252Y and S254T and T256E.

In one preferred embodiment the first Fc-region polypeptide comprises the mutation N434H.

In one embodiment the first Fc-region polypeptide further comprises the mutations Y349C, T366S, L368A and Y407V ("hole Fc-region polypeptide") and the second Fc-region polypeptide further comprises the mutations S354C and T366W ("knob Fc-region polypeptide").

In one embodiment of all aspects the variant (human) IgG class Fc-region comprises a first and a second Fc-region polypeptide of human IgG1 subclass wherein
  a) the first and the second Fc-region polypeptide both further comprise the mutations L234A and L235A (numbering according to Kabat EU index numbering system), or
  b) the first and the second Fc-region polypeptide both further comprise the mutation P329G (numbering according to Kabat EU index numbering system), or
  c) the first and the second Fc-region polypeptide both further comprise the mutations L234A and L235A and P329G (numbering according to Kabat EU index numbering system), or d) the first and the second Fc-region polypeptide both further comprise the mutations L234A and L235A (numbering according to Kabat EU index numbering system) and the first Fc-region polypeptide further comprises the mutation Y349C or S354C and the mutation T366W and the second Fc-region polypeptide further comprises the mutation Y349C or S354C and the mutations T366S, L368A and Y407V, or e) the first and the second Fc-region polypeptide both further comprise the mutations L234A and L235A and P329G (numbering according to Kabat EU index numbering system) and the first Fc-region polypeptide further comprises the mutation Y349C or S354C and the mutation T366W and the second Fc-region polypeptide further comprises the mutation Y349C or S354C and the mutations T366S, L368A and Y407V.

In one embodiment the variant (human) IgG class Fc-region comprises a first and a second Fc-region polypeptide of human IgG4 subclass wherein a) the first and the second Fc-region polypeptide both further comprise the mutations S228P and L235E (numbering according to Kabat EU index numbering system), or b) the first and the second Fc-region polypeptide both further comprise the mutation P329G (numbering according to Kabat EU index numbering system), or c) the first and the second Fc-region polypeptide both further comprise the mutations S228P and L235E and P329G (numbering according to Kabat EU index numbering system), or d) the first and the second Fc-region polypeptide both further comprise the mutations S228P and L235E (numbering according to Kabat EU index numbering system) and the first Fc-region polypeptide further comprises the mutation Y349C or S354C and the mutation T366W and the second Fc-region polypeptide further comprises the mutation Y349C or S354C and the mutations T366S, L368A and Y407V, e) the first and the second Fc-region polypeptide both further comprise the mutations S228P and L235E and P329G (numbering according to Kabat EU index numbering system) and the first Fc-region polypeptide further comprises the mutation Y349C or S354C and the mutation T366W and the second Fc-region polypeptide further comprises the mutation Y349C or S354C and the mutations T366S, L368A and Y407V.

One aspect as reported herein is an antibody or Fc-region fusion polypeptide comprising the variant (human) IgG class Fc-region as reported herein.

In one embodiment the antibody is a monoclonal antibody.

In one embodiment the antibody is a human, humanized, or chimeric antibody.

One aspect as reported herein is a nucleic acid encoding the variant (human) IgG class Fc-region as reported herein.

One aspect as reported herein is a nucleic acid encoding the antibody as reported herein.

One aspect as reported herein is a nucleic acid encoding the Fc-region fusion polypeptide as reported herein.

One aspect as reported herein is a host cell comprising the nucleic acid as reported herein.

One aspect as reported herein is a method of producing the variant (human) IgG class Fc-region as reported herein comprising culturing the host cell as reported herein so that the variant (human) IgG class Fc-region is produced.

One aspect as reported herein is a method of producing the antibody as reported herein comprising culturing the host cell as reported herein so that the antibody is produced.

One aspect as reported herein is a method of producing the Fc-region fusion polypeptide as reported herein comprising culturing the host cell as reported herein so that the Fc-region fusion polypeptide is produced.

One aspect as reported herein is a pharmaceutical formulation comprising the variant (human) IgG class Fc-region as reported herein or the antibody as reported herein or the Fc-region fusion polypeptide as reported herein.

One aspect as reported herein is the variant (human) IgG class Fc-region as reported herein or the antibody as reported herein or the Fc-region fusion polypeptide as reported herein for use as a medicament.

One aspect as reported herein is the use of the variant (human) IgG class Fc-region as reported herein or the antibody as reported herein or the Fc-region fusion polypeptide as reported herein in the manufacture of a medicament.

The antibodies as reported herein can be used as e.g. T-cell recruiters, as Fc gamma receptor binder with high biological activity (potency) and fast clearance from the blood circulation (blood serum), as antibody-drug-conjugates with fast clearance in order to reduce systemic side effects, or as pre-targeting antibodies.

DETAILED DESCRIPTION OF EMBODIMENTS OF THE INVENTION

I. Definitions

Figure 1:
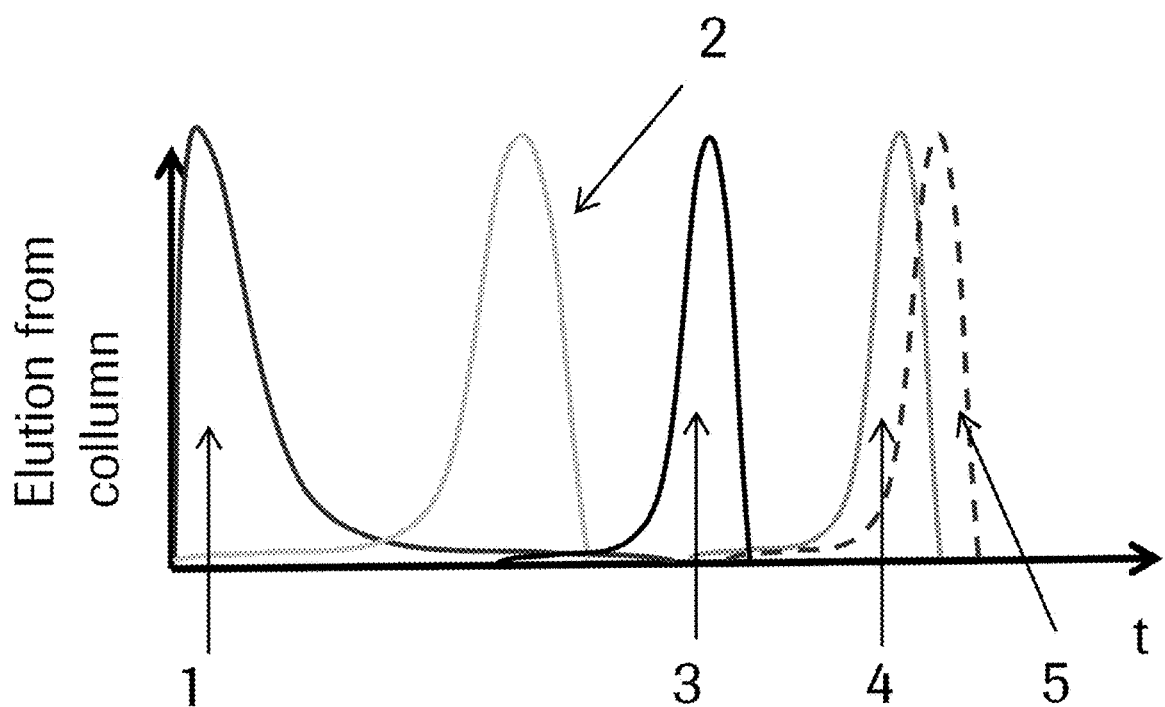
FIG. 1 Illustrative schematic FcRn affinity chromatography elution diagram of an antibody comprising different (variant) Fc-regions: 1: I253A/H310A/H435A mutation; 2: wild-type Fc-region; 3: M252Y/S254T/T256E in one Fc-region polypeptide, the other wild-type Fc-region; 4: M252Y/S254T/T256E in both Fc-region polypeptides; 5: knob-chain: M252Y/S254T/T256E, hole-chain: T307Q/N434A.
Figure 2:
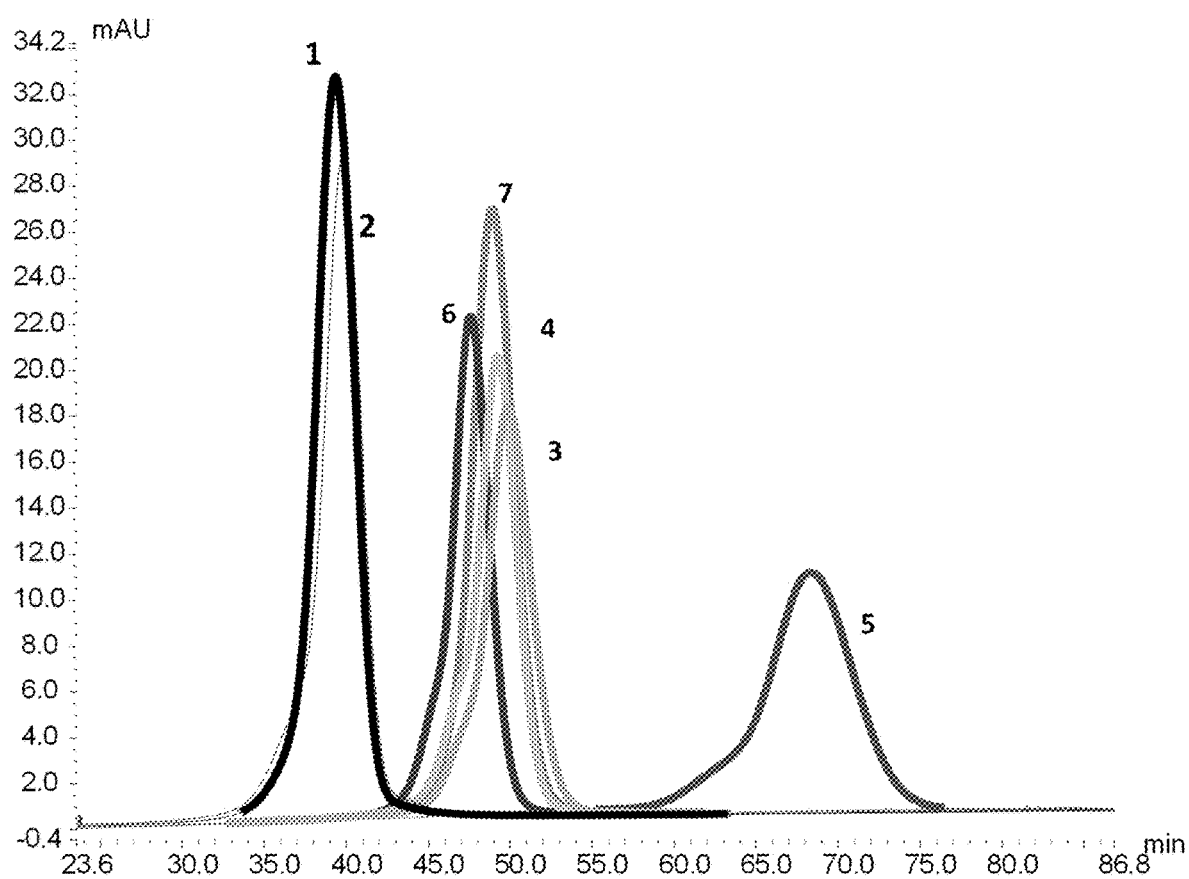
FIG. 2 FcRn affinity chromatography elution diagram of an antibody comprising different (variant) Fc-regions: 1: wild-type Fc-region; 2: glycoengineered Fc-region; 3: T307Q/N434A; 4: T307H/N434H; 5: T307H/N434H/M252Y/S254T/T256E; 6: N434H; 7: M252Y/S254T/T256E.
Figure 3:
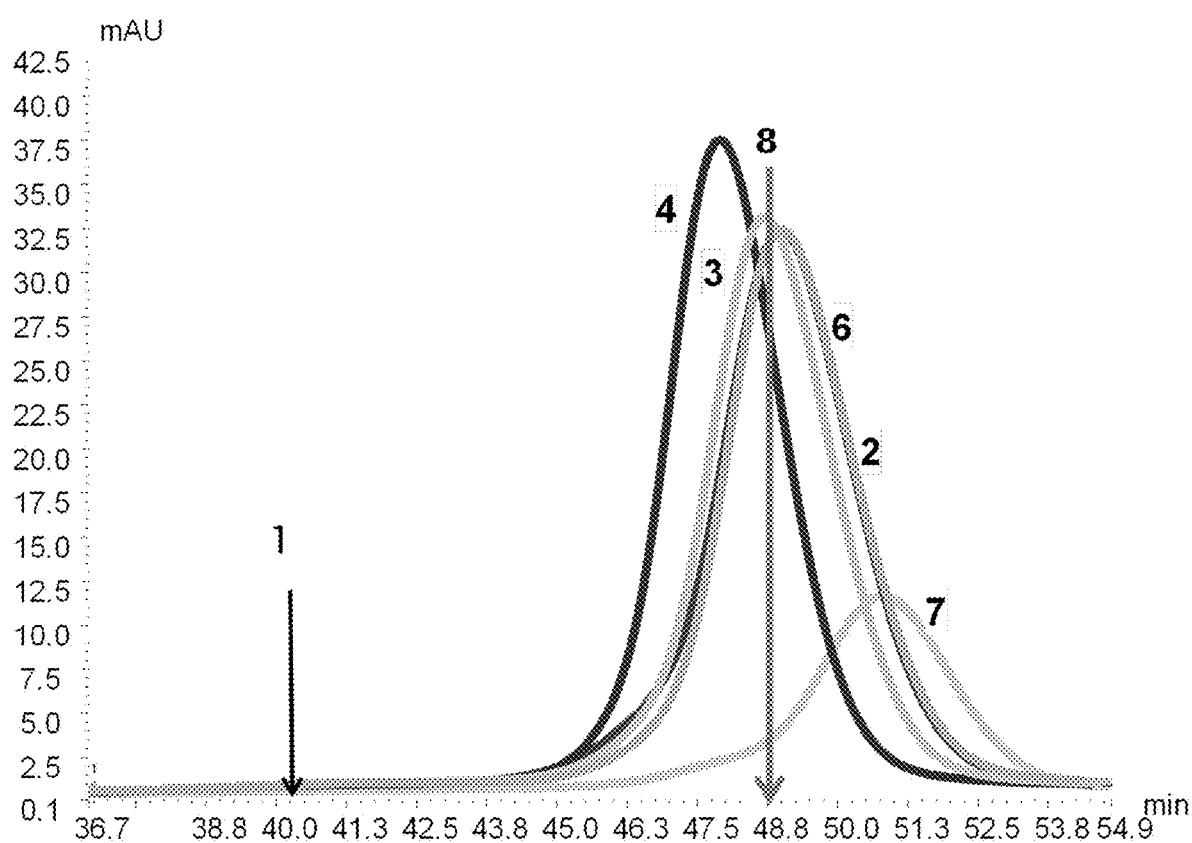
FIG. 3 FcRn affinity chromatography elution diagram of an antibody comprising different (variant) Fc-regions: 1: hole chain-knob chain Fc-region; 2: hole-chain: T307Q/N434A, knob-chain: M252Y/S254T/T256E; 3: hole-chain: T307H/N434H, knob-chain: M252Y/S254T/T256E; 4: hole-chain: T250Q/M428L, knob-chain: M252Y/S254T/T256E; 5: hole-chain: T307Q, N434H, knob-chain: M252Y/S254T/T256E/T307Q/N434H; 6: hole-chain: T307H/Q311H/E430H/N434H, knob-chain: M252Y/S254T/T256E; 7: hole-chain: T307H/Q311H/E430H/N434H, knob-chain: M252Y/S254T/T256E/T307H/Q311H/E430H/N434H; 8: hole-/knob-chain: M252Y/S254T/T256E.

The term "about" denotes a range of +/−20% of the thereafter following numerical value. In one embodiment the term about denotes a range of +/−10% of the thereafter following numerical value. In one embodiment the term about denotes a range of +/−5% of the thereafter following numerical value.

An "acceptor human framework" for the purposes herein is a framework comprising the amino acid sequence of a light chain variable domain (VL) framework or a heavy chain variable domain (VH) framework derived from a human immunoglobulin framework or a human consensus framework, as defined below. An acceptor human framework "derived from" a human immunoglobulin framework or a human consensus framework may comprise the same amino acid sequence thereof, or it may contain amino acid sequence alterations. In some embodiments, the number of amino acid alterations are 10 or less, 9 or less, 8 or less, 7 or less, 6 or less, 5 or less, 4 or less, 3 or less, or 2 or less. In some embodiments, the VL acceptor human framework is identical in sequence to the VL human immunoglobulin framework sequence or human consensus framework sequence.

An "affinity matured" antibody refers to an antibody with one or more alterations in one or more hypervariable regions (HVRs), compared to a parent antibody which does not possess such alterations, such alterations resulting in an improvement in the affinity of the antibody for antigen.

The term "alteration" denotes the mutation (substitution), insertion (addition), or deletion of one or more amino acid residues in a parent antibody or fusion polypeptide, e.g. a fusion polypeptide comprising at least an FcRn binding portion of an Fc-region, to obtain a modified antibody or fusion polypeptide. The term "mutation" denotes that the specified amino acid residue is substituted for a different amino acid residue. For example the mutation L234A denotes that the amino acid residue lysine at position 234 in an antibody Fc-region (polypeptide) is substituted by the amino acid residue alanine (substitution of lysine with alanine) (numbering according to the EU index).

The term "amino acid mutation" denotes the substitution of at least one existing amino acid residue with another different amino acid residue (=replacing amino acid residue). The replacing amino acid residue may be a "naturally occurring amino acid residues" and selected from the group consisting of alanine (three letter code: ala, one letter code: A), arginine (arg, R), asparagine (asn, N), aspartic acid (asp, D), cysteine (cys, C), glutamine (gln, Q), glutamic acid (glu, E), glycine (gly, G), histidine (his, H), isoleucine (ile, I), leucine (leu, L), lysine (lys, K), methionine (met, M), phenylalanine (phe, F), proline (pro, P), serine (ser, S), threonine (thr, T), tryptophan (trp, W), tyrosine (tyr, Y), and valine (val, V). The replacing amino acid residue may be a "non-naturally occurring amino acid residue". See e.g. U.S. Pat. No. 6,586,207, WO 98/48032, WO 03/073238, US 2004/0214988, WO 2005/35727, WO 2005/74524, Chin, J. W., et al., J. Am. Chem. Soc. 124 (2002) 9026-9027; Chin, J. W. and Schultz, P. G., ChemBioChem 11 (2002) 1135-1137; Chin, J. W., et al., PICAS United States of America 99 (2002) 11020-11024; and, Wang, L. and Schultz, P. G., Chem. (2002) 1-10 (all entirely incorporated by reference herein).

The term "amino acid insertion" denotes the (additional) incorporation of at least one amino acid residue at a predetermined position in an amino acid sequence. In one embodiment the insertion will be the insertion of one or two amino acid residues. The inserted amino acid residue(s) can be any naturally occurring or non-naturally occurring amino acid residue.

The term "amino acid deletion" denotes the removal of at least one amino acid residue at a predetermined position in an amino acid sequence.

The term "antibody" herein is used in the broadest sense and encompasses various antibody structures, including but not limited to monoclonal antibodies, multispecific antibodies (e.g. bispecific antibodies, trispecific antibodies), and antibody fragments so long as they exhibit the desired antigen- and/or protein A and/or FcRn-binding activity.

The term "asymmetric Fc-region" denotes a pair of Fc-region polypeptides that have different amino acid residues at corresponding positions according to the Kabat EU index numbering system.

The term "asymmetric Fc-region with respect to FcRn binding" denotes an Fc-region that consists of two polypeptide chains that have different amino acid residues at corresponding positions, whereby the positions are determined according to the Kabat EU index numbering system, whereby the different positions affect the binding of the Fc-region to the human neonatal Fc-receptor (FcRn). For the purpose herein the differences between the two polypeptide chains of the Fc-region in an "asymmetric Fc-region with respect to FcRn binding" do not include differences that have been introduced to facilitate the formation of heterodimeric Fc-regions, e.g. for the production of bispecific antibodies. These differences can also be asymmetric, i.e. the two chains have differences at non corresponding amino acid residues according to the Kabat EU index numbering system. These differences facilitate heterodimerization and reduce homodimerization. Examples of such differences are the so-called "knobs into holes" substitutions (see, e.g., U.S. Pat. No. 7,695,936 and US 2003/0078385). The following knobs and holes substitutions in the individual polypeptide chains of an Fc-region of an IgG antibody of subclass IgG1 have been found to increase heterodimer formation: 1) Y407T in one chain and T366Y in the other chain; 2) Y407A in one chain and T366W in the other chain; 3) F405A in one chain and T394W in the other chain; 4) F405W in one chain and T394S in the other chain; 5) Y407T in one chain and T366Y in the other chain; 6) T366Y and F405A in one chain and T394W and Y407T in the other chain; 7) T366W and F405W in one chain and T394S and Y407A in the other chain; 8) F405W and Y407A in one chain and T366W and T394S in the other chain; and 9) T366W in one chain and T366S, L368A, and Y407V in the other chain, whereby the last listed is especially suited. In addition, changes creating new disulfide bridges between the two Fc-region polypeptide chains facilitate heterodimer formation (see, e.g., US 2003/0078385). The following substitutions resulting in appropriately spaced apart cysteine residues for the formation of new intra-chain disulfide bonds in the individual polypeptide chains of an Fc-region of an IgG antibody of subclass IgG1 have been found to increase heterodimer formation: Y349C in one chain and S354C in the other; Y349C in one chain and E356C in the other; Y349C in one chain and E357C in the other; L351C in one chain and S354C in the other; T394C in one chain and E397C in the other; or D399C in one chain and K392C in the other. Further examples of heterodimerization facilitating amino acid changes are the so-called "charge pair substitutions" (see, e.g., WO 2009/089004). The following charge pair substitutions in the individual polypeptide chains of an Fc-region of an IgG antibody of subclass IgG1 have been found to increase heterodimer formation: 1) K409D or K409E in one chain and D399K or D399R in the other chain; 2) K392D or K392E in one chain and D399K or D399R in the other chain; 3) K439D or K439E in one chain and E356K or E356R in the other chain; 4) K370D or K370E in one chain and E357K or E357R in the other chain; 5) K409D and K360D in one chain plus D399K and E356K in the other chain; 6) K409D and K370D in one chain plus D399K and E357K in the other chain; 7) K409D and K392D in one chain plus D399K, E356K, and E357K in the other chain; 8) K409D and K392D in one chain and D399K in the other chain; 9) K409D and K392D in one chain and D399K and E356K in the other chain; 10) K409D and K392D in one chain and D399K and D357K in the other chain; 11) K409D and K370D in one chain and D399K and D357K in the other chain; 12) D399K in one chain and K409D and K360D in the other chain; and 13) K409D and K439D in one chain and D399K and E356K on the other.

The term "binding (to an antigen)" denotes the binding of an antibody to its antigen in an in vitro assay, in one embodiment in a binding assay in which the antibody is bound to a surface and binding of the antigen to the antibody is measured by Surface Plasmon Resonance (SPR). Binding means a binding affinity ($K_D$) of $10^{-8}$ M or less, in some embodiments of $10^{-13}$ to $10^{-8}$ M, in some embodiments of $10^{-13}$ to $10^{-9}$ M.

Binding can be investigated by a BIAcore assay (GE Healthcare Biosensor AB, Uppsala, Sweden). The affinity of the binding is defined by the terms $k_a$ (rate constant for the association of the antibody from the antibody/antigen complex), $k_d$ (dissociation constant), and $K_D(k_d/k_a)$.

The term "chimeric" antibody refers to an antibody in which a portion of the heavy and/or light chain is derived from a particular source or species, while the remainder of the heavy and/or light chain is derived from a different source or species.

The term "CH2-domain" denotes the part of an antibody heavy chain polypeptide that extends approximately from EU position 231 to EU position 340 (EU numbering system according to Kabat). In one embodiment a CH2 domain has the amino acid sequence of SEQ ID NO: 01: APELLGG PSVFLFPPKP KDTLMISRTP EVTCVWDVS HEDPE-VKFNW YVDGVEVHNA KTKPREEQ E STYRWSVLT VLHQDWLNGK EYKCKVSNKA LPAPIEKTIS KAK.

The term "CH3-domain" denotes the part of an antibody heavy chain polypeptide that extends approximately from EU position 341 to EU position 446. In one embodiment the CH3 domain has the amino acid sequence of SEQ ID NO: 2: GQPREPQ VYTLPPSRDE LTKNQVSLTC LVKG-FYPSDI AVEWESNGQP ENNYKTTPPV LDSDGSFFLY SKLTVDKSRW QQGNVFSCSV MHEALHNHYT QKSLSLSPG.

The "class" of an antibody refers to the type of constant domain or constant region possessed by its heavy chain. There are five major classes of antibodies: IgA, IgD, IgE, IgG, and IgM, and several of these may be further divided into subclasses (isotypes), e.g., $IgG_1$, $IgG_2$, $IgG_3$, $IgG_4$, $IgA_1$, and $IgA_2$. The heavy chain constant domains that correspond to the different classes of immunoglobulins are called α, δ, ε, γ, and μ, respectively.

The term "comparable length" denotes that two polypeptides comprise the identical number of amino acid residues or can be different in length by one or more and up to 10 amino acid residues at most. In one embodiment the Fc-region polypeptides comprise the identical number of amino acid residues or differ by a number of from 1 to 10 amino acid residues. In one embodiment the Fc-region polypeptides comprise the identical number of amino acid residues or differ by a number of from 1 to 5 amino acid residues. In one embodiment the Fc-region polypeptides comprise the identical number of amino acid residues or differ by a number of from 1 to 3 amino acid residues.

The term "derived from" denotes that an amino acid sequence is derived from a parent amino acid sequence by introducing alterations at at least one position. Thus a derived amino acid sequence differs from the corresponding parent amino acid sequence at at least one corresponding position (numbering according to Kabat EU index numbering system for antibody Fc-regions). In one embodiment an amino acid sequence derived from a parent amino acid sequence differs by one to fifteen amino acid residues at corresponding positions. In one embodiment an amino acid sequence derived from a parent amino acid sequence differs by one to ten amino acid residues at corresponding positions. In one embodiment an amino acid sequence derived from a parent amino acid sequence differs by one to six amino acid residues at corresponding positions. Likewise a derived amino acid sequence has a high amino acid sequence identity to its parent amino acid sequence. In one embodiment an amino acid sequence derived from a parent amino acid sequence has 80% or more amino acid sequence identity. In one embodiment an amino acid sequence derived from a parent amino acid sequence has 90% or more amino acid sequence identity. In one embodiment an amino acid sequence derived from a parent amino acid sequence has 95% or more amino acid sequence identity.

"Effector functions" refer to those biological activities attributable to the Fc-region of an antibody, which vary with the antibody class. Examples of antibody effector functions include: C1q binding and complement dependent cytotoxicity (CDC); Fc receptor binding; antibody-dependent cell-mediated cytotoxicity (ADCC); phagocytosis; down regulation of cell surface receptors (e.g. B-cell receptor); and B-cell activation.

An "effective amount" of an agent, e.g., a pharmaceutical formulation, refers to an amount effective, at dosages and for periods of time necessary, to achieve the desired therapeutic or prophylactic result.

The term "Fc-fusion polypeptide" denotes a fusion of a binding domain (e.g. an antigen binding domain such as a single chain antibody, or a polypeptide such as a ligand of a receptor) with an antibody Fc-region that exhibits the desired target- and/or protein A and/or FcRn-binding activity.

The term "Fc-region of human origin" denotes the C-terminal region of an immunoglobulin heavy chain of human origin that contains at least a part of the hinge region, the CH2 domain and the CH3 domain. In one embodiment, a human IgG heavy chain Fc-region extends from Cys226, or from Pro230, to the carboxyl-terminus of the heavy chain. In one embodiment the Fc-region has the amino acid sequence of SEQ ID NO: 60. However, the C-terminal lysine (Lys447) of the Fc-region may or may not be present. Unless otherwise specified herein, numbering of amino acid residues in the Fc-region or constant region is according to the EU numbering system, also called the EU index, as described in Kabat, E. A., et al., Sequences of Proteins of Immunological Interest, 5th ed., Public Health Service, National Institutes of Health, Bethesda, Md. (1991), NIH Publication 91 3242. The Fc-region is composed of two heavy chain Fc-region polypeptides, which can be covalently linked to each other via the hinge region cysteine residues forming inter-polypeptide disulfide bonds.

The term "FcRn" denotes the human neonatal Fc-receptor. FcRn functions to salvage IgG from the lysosomal degradation pathway, resulting in reduced clearance and increased half-life. The FcRn is a heterodimeric protein consisting of two polypeptides: a 50 kDa class I major histocompatibility complex-like protein (α-FcRn) and a 15 kDa β2-microglobulin (β2m). FcRn binds with high affinity to the CH2-CH3 portion of the Fc-region of IgG. The interaction between IgG and FcRn is strictly pH dependent and occurs in a 1:2 stoichiometry, with one IgG binding to two FcRn molecules via its two heavy chains (Huber, A. H., et al., J. Mol. Biol. 230 (1993) 1077-1083). FcRn binding occurs in the endosome at acidic pH (pH<6.5) and IgG is released at the neutral cell surface (pH of about 7.4). The pH-sensitive nature of the interaction facilitates the FcRn-mediated protection of IgGs pinocytosed into cells from intracellular degradation by binding to the receptor within the acidic environment of endosomes. FcRn then facilitates the recycling of IgG to the cell surface and subsequent release into the blood stream upon exposure of the FcRn-IgG complex to the neutral pH environment outside the cell.

The term "FcRn binding portion of an Fc-region" denotes the part of an antibody heavy chain polypeptide that extends approximately from EU position 243 to EU position 261 and approximately from EU position 275 to EU position 293 and approximately from EU position 302 to EU position 319 and approximately from EU position 336 to EU position 348 and approximately from EU position 367 to EU position 393 and EU position 408 and approximately from EU position 424 to EU position 440. In one embodiment one or more of the following amino acid residues according to the EU numbering of Kabat are altered F243, P244, P245 P, K246, P247, K248, D249, T250, L251, M252, I253, S254, R255, T256, P257, E258, V259, T260, C261, F275, N276, W277, Y278, V279, D280, V282, E283, V284, H285, N286, A287, K288, T289, K290, P291, R292, E293, V302, V303, S304, V305, L306, T307, V308, L309, H310, Q311, D312, W313, L314, N315, G316, K317, E318, Y319, I336, S337, K338, A339, K340, G341, Q342, P343, R344, E345, P346, Q347, V348, C367, V369, F372, Y373, P374, S375, D376, I377, A378, V379, E380, W381, E382, S383, N384, G385, Q386, P387, E388, N389, Y391, T393, S408, S424, C425, S426, V427, M428, H429, E430, A431, L432, H433, N434, H435, Y436, T437, Q438, K439, and S440 (EU numbering).

"Framework" or "FR" refers to variable domain residues other than hypervariable region (HVR) residues. The FR of a variable domain generally consists of four FR domains: FR1, FR2, FR3, and FR4. Accordingly, the HVR and FR sequences generally appear in the following sequence in VH (or VL): FR1-H1(L1)-FR2-H2(L2)-FR3-H3 (L3)-FR4.

The term "full length antibody" denotes an antibody having a structure substantially similar to a native antibody structure or having heavy chains that contain an Fc-region as defined herein. A full length antibody may comprise further domains, such as e.g. a scFv or a scFab conjugated to one or more of the chains of the full length antibody. These conjugates are also encompassed by the term full length antibody.

The terms "heterodimer" or "heterodimeric" denote a molecule that comprises two polypeptide chains (e.g. of comparable length), wherein the two polypeptide chains have an amino acid sequence that have at least one different amino acid residue in a corresponding position, whereby corresponding position is determined according to the EU index of Kabat.

The terms "homodimer" and "homodimeric" denote a molecule that comprises two polypeptide chains of comparable length, wherein the two polypeptide chains have an amino acid sequence that is identical in corresponding positions, whereby corresponding positions are determined according to the EU index of Kabat.

An antibody or Fc-region fusion polypeptide as reported herein can be homodimeric or heterodimeric with respect to its Fc-region which is determined with respect to mutations or properties in focus. For example, with respect to FcRn and/or protein A binding (i.e. the focused on properties) an Fc-region (antibody) is homodimeric (i.e. both heavy chain Fc-region polypeptides comprise these mutations) with respect to the mutations H310A, H433A and Y436A (these mutations are in focus with respect to FcRn and/or protein A binding property of the Fc-region fusion polypeptide or antibody) but at the same time heterodimeric with respect to the mutations Y349C, T366S, L368A and Y407V (these mutations are not in focus as these mutations are directed to the heterodimerization of the heavy chains and not to the FcRn/protein A binding properties) as well as the mutations S354C and T366W, respectively (the first set is comprised only in the first Fc-region polypeptide whereas the second set is comprised only in the second Fc-region polypeptide). Further for example, an Fc-region fusion polypeptide or an antibody as reported herein can be heterodimeric with respect to the mutations I253A, H310A, H433A, H435A and Y436A (i.e. these mutations are directed all to the FcRn and/or protein A binding properties of the dimeric polypeptide), i.e. one Fc-region polypeptide comprises the mutations I253A, H310A and H435A, whereas the other Fc-region polypeptide comprises the mutations H310A, H433A and Y436A.

The terms "host cell", "host cell line", and "host cell culture" are used interchangeably and refer to cells into which exogenous nucleic acid has been introduced, including the progeny of such cells. Host cells include "transformants" and "transformed cells," which include the primary transformed cell and progeny derived therefrom without regard to the number of passages. Progeny may not be completely identical in nucleic acid content to a parent cell, but may contain mutations. Mutant progeny that have the same function or biological activity as screened or selected for in the originally transformed cell are included herein.

A "human antibody" is one which possesses an amino acid sequence which corresponds to that of an antibody produced by a human or a human cell or derived from a non-human source that utilizes human antibody repertoires or other human antibody-encoding sequences. This definition of a human antibody specifically excludes a humanized antibody comprising non-human antigen-binding residues.

A "human consensus framework" is a framework which represents the most commonly occurring amino acid residues in a selection of human immunoglobulin VL or VH framework sequences. Generally, the selection of human immunoglobulin VL or VH sequences is from a subgroup of variable domain sequences. Generally, the subgroup of sequences is a subgroup as in Kabat, E. A. et al., Sequences of Proteins of Immunological Interest, 5th ed., Bethesda Md. (1991), NIH Publication 91-3242, Vols. 1-3. In one embodiment, for the VL, the subgroup is subgroup kappa I as in Kabat et al., supra. In one embodiment, for the VH, the subgroup is subgroup III as in Kabat et al., supra.

The term "human Fc-region polypeptide" denotes an amino acid sequence which is identical to a "native" or "wild-type" human Fc-region polypeptide. The term "variant (human) Fc-region polypeptide" denotes an amino acid sequence which derived from a "native" or "wild-type" human Fc-region polypeptide by virtue of at least one "amino acid alteration". A "human Fc-region" is consisting of two human Fc-region polypeptides. A "variant (human) Fc-region" is consisting of two Fc-region polypeptides, whereby both can be variant (human) Fc-region polypeptides or one is a human Fc-region polypeptide and the other is a variant (human) Fc-region polypeptide.

In one embodiment the human Fc-region polypeptide has the amino acid sequence of a human IgG1 Fc-region polypeptide of SEQ ID NO: 03, or of a human IgG2 Fc-region polypeptide of SEQ ID NO: 04, or of a human IgG3

Fc-region polypeptide of SEQ ID NO: 05, or of a human IgG4 Fc-region polypeptide of SEQ ID NO: 06. In one embodiment the variant (human) Fc-region polypeptide is derived from an Fc-region polypeptide of SEQ ID NO: 03, or 04, or 05, or 06 and has at least one amino acid mutation compared to the human Fc-region polypeptide of SEQ ID NO: 03, or 04, or 05, or 06. In one embodiment the variant (human) Fc-region polypeptide comprises/has from about one to about twelve amino acid mutations, and in one embodiment from about one to about eight amino acid mutations. In one embodiment the variant (human) Fc-region polypeptide has at least about 80% homology with a human Fc-region polypeptide of SEQ ID NO: 03, or 04, or 05, or 06. In one embodiment the variant (human) Fc-region polypeptide has least about 90% homology with a human Fc-region polypeptide of SEQ ID NO: 03, or 04, or 05, or 06. In one embodiment the variant (human) Fc-region polypeptide has at least about 95% homology with a human Fc-region polypeptide of SEQ ID NO: 03, or 04, or 05, or 06.

The variant (human) Fc-region polypeptide derived from a human Fc-region polypeptide of SEQ ID NO: 03, or 04, or 05, or 06 is defined by the amino acid alterations that are contained. Thus, for example, the term P329G denotes a variant (human) Fc-region polypeptide derived human Fc-region polypeptide with the mutation of proline to glycine at amino acid position 329 relative to the human Fc-region polypeptide of SEQ ID NO: 03, or 04, or 05, or 06.

As used herein, the amino acid positions of all constant regions and domains of the heavy and light chain are numbered according to the Kabat numbering system described in Kabat, et al., Sequences of Proteins of Immunological Interest, 5th ed., Public Health Service, National Institutes of Health, Bethesda, Md. (1991) and is referred to as "numbering according to Kabat" herein. Specifically the Kabat numbering system (see pages 647-660) of Kabat, et al., Sequences of Proteins of Immunological Interest, 5th ed., Public Health Service, National Institutes of Health, Bethesda, Md. (1991) is used for the light chain constant domain CL of kappa and lambda isotype and the Kabat EU index numbering system (see pages 661-723) is used for the constant heavy chain domains (CH1, Hinge, CH2 and CH3).

A human IgG1 Fc-region polypeptide has the following amino acid sequence:

```
                                              (SEQ ID NO: 03)
DKTHTCPPCPAPELLGGPSVFLFPPKPKDTLMISRTPEVTCVVVDVSHED

PEVKFNWYVDGVEVHNAKTKPREEQYNSTYRVVSVLTVLHQDWLNGKEYK

CKVSNKALPAPIEKTISKAKGQPREPQVYTLPPSRDELTKNQVSLTCLVK

GFYPSDIAVEWESNGQPENNYKTTPPVLDSDGSFFLYSKLTVDKSRWQQG

NVFSCSVMHEALHNHYTQKSLSLSPGK.
```

A human IgG1 Fc-region derived Fc-region polypeptide with the mutations L234A, L235A has the following amino acid sequence:

```
                                              (SEQ ID NO: 07)
DKTHTCPPCPAPEAAGGPSVFLFPPKPKDTLMISRTPEVTCVVVDVSHED

PEVKFNWYVDGVEVHNAKTKPREEQYNSTYRVVSVLTVLHQDWLNGKEYK

CKVSNKALPAPIEKTISKAKGQPREPQVYTLPPSRDELTKNQVSLTCLVK

GFYPSDIAVEWESNGQPENNYKTTPPVLDSDGSFFLYSKLTVDKSRWQQG

NVFSCSVMHEALHNHYTQKSLSLSPGK.
```

A human IgG1 Fc-region derived Fc-region polypeptide with Y349C, T366S, L368A and Y407V mutations has the following amino acid sequence:

```
                                              (SEQ ID NO: 08)
DKTHTCPPCPAPELLGGPSVFLFPPKPKDTLMISRTPEVTCVVVDVSHED

PEVKFNWYVDGVEVHNAKTKPREEQYNSTYRVVSVLTVLHQDWLNGKEYK

CKVSNKALPAPIEKTISKAKGQPREPQVCTLPPSRDELTKNQVSLSCAVK

GFYPSDIAVEWESNGQPENNYKTTPPVLDSDGSFFLVSKLTVDKSRWQQG

NVFSCSVMHEALHNHYTQKSLSLSPGK.
```

A human IgG1 Fc-region derived Fc-region polypeptide with S354C, T366W mutations has the following amino acid sequence:

```
                                              (SEQ ID NO: 09)
DKTHTCPPCPAPELLGGPSVFLFPPKPKDTLMISRTPEVTCVVVDVSHED

PEVKFNWYVDGVEVHNAKTKPREEQYNSTYRVVSVLTVLHQDWLNGKEYK

CKVSNKALPAPIEKTISKAKGQPREPQVYTLPPCRDELTKNQVSLWCLVK

GFYPSDIAVEWESNGQPENNYKTTPPVLDSDGSFFLYSKLTVDKSRWQQG

NVFSCSVMHEALHNHYTQKSLSLSPGK.
```

A human IgG1 Fc-region derived Fc-region polypeptide with L234A, L235A mutations and Y349C, T366S, L368A, Y407V mutations has the following amino acid sequence:

```
                                              (SEQ ID NO: 10)
DKTHTCPPCPAPEAAGGPSVFLFPPKPKDTLMISRTPEVTCVVVDVSHED

PEVKFNWYVDGVEVHNAKTKPREEQYNSTYRVVSVLTVLHQDWLNGKEYK

CKVSNKALPAPIEKTISKAKGQPREPQVCTLPPSRDELTKNQVSLSCAVK

GFYPSDIAVEWESNGQPENNYKTTPPVLDSDGSFFLVSKLTVDKSRWQQG

NVFSCSVMHEALHNHYTQKSLSLSPGK.
```

A human IgG1 Fc-region derived Fc-region polypeptide with a L234A, L235A and S354C, T366W mutations has the following amino acid sequence:

```
                                              (SEQ ID NO: 11)
DKTHTCPPCPAPEAAGGPSVFLFPPKPKDTLMISRTPEVTCVVVDVSHED

PEVKFNWYVDGVEVHNAKTKPREEQYNSTYRVVSVLTVLHQDWLNGKEYK

CKVSNKALPAPIEKTISKAKGQPREPQVYTLPPCRDELTKNQVSLWCLVK

GFYPSDIAVEWESNGQPENNYKTTPPVLDSDGSFFLYSKLTVDKSRWQQG

NVFSCSVMHEALHNHYTQKSLSLSPGK.
```

A human IgG1 Fc-region derived Fc-region polypeptide with a P329G mutation has the following amino acid sequence:

```
                                              (SEQ ID NO: 12)
DKTHTCPPCPAPELLGGPSVFLFPPKPKDTLMISRTPEVTCVVVDVSHED

PEVKFNWYVDGVEVHNAKTKPREEQYNSTYRVVSVLTVLHQDWLNGKEYK
```

-continued

CKVSNKALGAPIEKTISKAKGQPREPQVYTLPPSRDELTKNQVSLTCLVK

GFYPSDIAVEWESNGQPENNYKTTPPVLDSDGSFFLYSKLTVDKSRWQQG

NVFSCSVMHEALHNHYTQKSLSLSPGK.

A human IgG1 Fc-region derived Fc-region polypeptide with L234A, L235A mutations and P329G mutation has the following amino acid sequence:

(SEQ ID NO: 13)
DKTHTCPPCPAPEAAGGPSVFLFPPKPKDTLMISRTPEVTCVVVDVSHED

PEVKFNWYVDGVEVHNAKTKPREEQYNSTYRVVSVLTVLHQDWLNGKEYK

CKVSNKALGAPIEKTISKAKGQPREPQVYTLPPSRDELTKNQVSLTCLVK

GFYPSDIAVEWESNGQPENNYKTTPPVLDSDGSFFLYSKLTVDKSRWQQG

NVFSCSVMHEALHNHYTQKSLSLSPGK.

A human IgG1 Fc-region derived Fc-region polypeptide with a P239G mutation and Y349C, T366S, L368A, Y407V mutations has the following amino acid sequence:

(SEQ ID NO: 14)
DKTHTCPPCPAPELLGGPSVFLFPPKPKDTLMISRTPEVTCVVVDVSHED

PEVKFNWYVDGVEVHNAKTKPREEQYNSTYRVVSVLTVLHQDWLNGKEYK

CKVSNKALGAPIEKTISKAKGQPREPQVCTLPPSRDELTKNQVSLSCAVK

GFYPSDIAVEWESNGQPENNYKTTPPVLDSDGSFFLVSKLTVDKSRWQQG

NVFSCSVMHEALHNHYTQKSLSLSPGK.

A human IgG1 Fc-region derived Fc-region polypeptide with a P329G mutation and S354C, T366W mutation has the following amino acid sequence:

(SEQ ID NO: 15)
DKTHTCPPCPAPELLGGPSVFLFPPKPKDTLMISRTPEVTCVVVDVSHED

PEVKFNWYVDGVEVHNAKTKPREEQYNSTYRVVSVLTVLHQDWLNGKEYK

CKVSNKALGAPIEKTISKAKGQPREPQVYTLPPCRDELTKNQVSLWCLVK

GFYPSDIAVEWESNGQPENNYKTTPPVLDSDGSFFLYSKLTVDKSRWQQG

NVFSCSVMHEALHNHYTQKSLSLSPGK.

A human IgG1 Fc-region derived Fc-region polypeptide with L234A, L235A, P329G and Y349C, T366S, L368A, Y407V mutations has the following amino acid sequence:

(SEQ ID NO: 16)
DKTHTCPPCPAPEAAGGPSVFLFPPKPKDTLMISRTPEVTCVVVDVSHED

PEVKFNWYVDGVEVHNAKTKPREEQYNSTYRVVSVLTVLHQDWLNGKEYK

CKVSNKALGAPIEKTISKAKGQPREPQVCTLPPSRDELTKNQVSLSCAVK

GFYPSDIAVEWESNGQPENNYKTTPPVLDSDGSFFLVSKLTVDKSRWQQG

NVFSCSVMHEALHNHYTQKSLSLSPGK.

A human IgG1 Fc-region derived Fc-region polypeptide with L234A, L235A, P329G mutations and S354C, T366W mutations has the following amino acid sequence:

(SEQ ID NO: 17)
DKTHTCPPCPAPEAAGGPSVFLFPPKPKDTLMISRTPEVTCVVVDVSHED

PEVKFNWYVDGVEVHNAKTKPREEQYNSTYRVVSVLTVLHQDWLNGKEYK

CKVSNKALGAPIEKTISKAKGQPREPQVYTLPPCRDELTKNQVSLWCLVK

GFYPSDIAVEWESNGQPENNYKTTPPVLDSDGSFFLYSKLTVDKSRWQQG

NVFSCSVMHEALHNHYTQKSLSLSPGK.

A human IgG4 Fc-region polypeptide has the following amino acid sequence:

(SEQ ID NO: 06)
ESKYGPPCPSCPAPEFLGGPSVFLFPPKPKDTLMISRTPEVTCVVVDVSQ

EDPEVQFNWYVDGVEVHNAKTKPREEQFNSTYRVVSVLTVLHQDWLNGKE

YKCKVSNKGLPSSIEKTISKAKGQPREPQVYTLPPSQEEMTKNQVSLTCL

VKGFYPSDIAVEWESNGQPENNYKTTPPVLDSDGSFFLYSRLTVDKSRWQ

EGNVFSCSVMHEALHNHYTQKSLSLSLGK.

A human IgG4 Fc-region derived Fc-region polypeptide with S228P and L235E mutations has the following amino acid sequence:

(SEQ ID NO: 18)
ESKYGPPCPPCPAPEFEGGPSVFLFPPKPKDTLMISRTPEVTCVVVDVSQ

EDPEVQFNWYVDGVEVHNAKTKPREEQFNSTYRVVSVLTVLHQDWLNGKE

YKCKVSNKGLPSSIEKTISKAKGQPREPQVYTLPPSQEEMTKNQVSLTCL

VKGFYPSDIAVEWESNGQPENNYKTTPPVLDSDGSFFLYSRLTVDKSRWQ

EGNVFSCSVMHEALHNHYTQKSLSLSLGK.

A human IgG4 Fc-region derived Fc-region polypeptide with S228P, L235E mutations and P329G mutation has the following amino acid sequence:

(SEQ ID NO: 19)
ESKYGPPCPPCPAPEFEGGPSVFLFPPKPKDTLMISRTPEVTCVVVDVSQ

EDPEVQFNWYVDGVEVHNAKTKPREEQFNSTYRVVSVLTVLHQDWLNGKE

YKCKVSNKGLGSSIEKTISKAKGQPREPQVYTLPPSQEEMTKNQVSLTCL

VKGFYPSDIAVEWESNGQPENNYKTTPPVLDSDGSFFLYSRLTVDKSRWQ

EGNVFSCSVMHEALHNHYTQKSLSLSLGK.

A human IgG4 Fc-region derived Fc-region polypeptide with S354C, T366W mutations has the following amino acid sequence:

(SEQ ID NO: 20)
ESKYGPPCPSCPAPEFLGGPSVFLFPPKPKDTLMISRTPEVTCVVVDVSQ

EDPEVQFNWYVDGVEVHNAKTKPREEQFNSTYRVVSVLTVLHQDWLNGKE

YKCKVSNKGLPSSIEKTISKAKGQPREPQVYTLPPCQEEMTKNQVSLWCL

VKGFYPSDIAVEWESNGQPENNYKTTPPVLDSDGSFFLYSRLTVDKSRWQ

EGNVFSCSVMHEALHNHYTQKSLSLSLGK.

A human IgG4 Fc-region derived Fc-region polypeptide with Y349C, T366S, L368A, Y407V mutations has the following amino acid sequence:

(SEQ ID NO: 21)
ESKYGPPCPSCPAPEFLGGPSVFLFPPKPKDTLMISRTPEVTCVVVDVSQ

EDPEVQFNWYVDGVEVHNAKTKPREEQFNSTYRVVSVLTVLHQDWLNGKE

YKCKVSNKGLPSSIEKTISKAKGQPREPQVCTLPPSQEEMTKNQVSLSCA

VKGFYPSDIAVEWESNGQPENNYKTTPPVLDSDGSFFLYSRLTVDKSRWQ

EGNVFSCSVMHEALHNHYTQKSLSLSLGK.

A human IgG4 Fc-region derived Fc-region polypeptide with a S228P, L235E and S354C, T366W mutations has the following amino acid sequence:

(SEQ ID NO: 22)
ESKYGPPCPPCPAPEFEGGPSVFLFPPKPKDTLMISRTPEVTCVVVDVSQ

EDPEVQFNWYVDGVEVHNAKTKPREEQFNSTYRVVSVLTVLHQDWLNGKE

YKCKVSNKGLPSSIEKTISKAKGQPREPQVYTLPPCQEEMTKNQVSLWCL

VKGFYPSDIAVEWESNGQPENNYKTTPPVLDSDGSFFLYSRLTVDKSRWQ

EGNVFSCSVMHEALHNHYTQKSLSLSLGK.

A human IgG4 Fc-region derived Fc-region polypeptide with a S228P, L235E and Y349C, T366S, L368A, Y407V mutations has the following amino acid sequence:

(SEQ ID NO: 23)
ESKYGPPCPPCPAPEFEGGPSVFLFPPKPKDTLMISRTPEVTCVVVDVSQ

EDPEVQFNWYVDGVEVHNAKTKPREEQFNSTYRVVSVLTVLHQDWLNGKE

YKCKVSNKGLPSSIEKTISKAKGQPREPQVCTLPPSQEEMTKNQVSLSCA

VKGFYPSDIAVEWESNGQPENNYKTTPPVLDSDGSFFLVSRLTVDKSRWQ

EGNVFSCSVMHEALHNHYTQKSLSLSLGK.

A human IgG4 Fc-region derived Fc-region polypeptide with a P329G mutation has the following amino acid sequence:

(SEQ ID NO: 24)
ESKYGPPCPSCPAPEFLGGPSVFLFPPKPKDTLMISRTPEVTCVVVDVSQ

EDPEVQFNWYVDGVEVHNAKTKPREEQFNSTYRVVSVLTVLHQDWLNGKE

YKCKVSNKGLGSSIEKTISKAKGQPREPQVYTLPPSQEEMTKNQVSLTCL

VKGFYPSDIAVEWESNGQPENNYKTTPPVLDSDGSFFLYSRLTVDKSRWQ

EGNVFSCSVMHEALHNHYTQKSLSLSLGK.

A human IgG4 Fc-region derived Fc-region polypeptide with a P239G and Y349C, T366S, L368A, Y407V mutations has the following amino acid sequence:

(SEQ ID NO: 25)
ESKYGPPCPSCPAPEFLGGPSVFLFPPKPKDTLMISRTPEVTCVVVDVSQ

EDPEVQFNWYVDGVEVHNAKTKPREEQFNSTYRVVSVLTVLHQDWLNGKE

YKCKVSNKGLGSSIEKTISKAKGQPREPQVCTLPPSQEEMTKNQVSLSCA

VKGFYPSDIAVEWESNGQPENNYKTTPPVLDSDGSFFLVSRLTVDKSRWQ

EGNVFSCSVMHEALHNHYTQKSLSLSLGK.

A human IgG4 Fc-region derived Fc-region polypeptide with a P329G and S354C, T366W mutations has the following amino acid sequence:

(SEQ ID NO: 26)
ESKYGPPCPSCPAPEFLGGPSVFLFPPKPKDTLMISRTPEVTCVVVDVSQ

EDPEVQFNWYVDGVEVHNAKTKPREEQFNSTYRVVSVLTVLHQDWLNGKE

YKCKVSNKGLGSSIEKTISKAKGQPREPQVYTLPPCQEEMTKNQVSLWCL

VKGFYPSDIAVEWESNGQPENNYKTTPPVLDSDGSFFLYSRLTVDKSRWQ

EGNVFSCSVMHEALHNHYTQKSLSLSLGK.

A human IgG4 Fc-region derived Fc-region polypeptide with a S228P, L235E, P329G and Y349C, T366S, L368A, Y407V mutations has the following amino acid sequence:

(SEQ ID NO: 27)
ESKYGPPCPPCPAPEFEGGPSVFLFPPKPKDTLMISRTPEVTCVVVDVSQ

EDPEVQFNWYVDGVEVHNAKTKPREEQFNSTYRVVSVLTVLHQDWLNGKE

YKCKVSNKGLGSSIEKTISKAKGQPREPQVCTLPPSQEEMTKNQVSLSCA

VKGFYPSDIAVEWESNGQPENNYKTTPPVLDSDGSFFLVSRLTVDKSRWQ

EGNVFSCSVMHEALHNHYTQKSLSLSLGK.

A human IgG4 Fc-region derived Fc-region polypeptide with a S228P, L235E, P329G and S354C, T366W mutations has the following amino acid sequence:

(SEQ ID NO: 28)
ESKYGPPCPPCPAPEFEGGPSVFLFPPKPKDTLMISRTPEVTCVVVDVSQ

EDPEVQFNWYVDGVEVHNAKTKPREEQFNSTYRVVSVLTVLHQDWLNGKE

YKCKVSNKGLGSSIEKTISKAKGQPREPQVYTLPPCQEEMTKNQVSLWCL

VKGFYPSDIAVEWESNGQPENNYKTTPPVLDSDGSFFLYSRLTVDKSRWQ

EGNVFSCSVMHEALHNHYTQKSLSLSLGK.

A "humanized" antibody refers to a chimeric antibody comprising amino acid residues from non-human HVRs and amino acid residues from human FRs. In certain embodiments, a humanized antibody will comprise substantially all of at least one, and typically two, variable domains, in which all or substantially all of the HVRs (e.g., the CDRs) correspond to those of a non-human antibody, and all or substantially all of the FRs correspond to those of a human antibody. A humanized antibody optionally may comprise at least a portion of an antibody constant region derived from a human antibody. A "humanized form" of an antibody, e.g., a non-human antibody, refers to an antibody that has undergone humanization.

The term "hypervariable region" or "HVR", as used herein, refers to each of the regions of an antibody variable domain which are hypervariable in sequence ("complementarity determining regions" or "CDRs") and form structurally defined loops ("hypervariable loops"), and/or contain the antigen-contacting residues ("antigen contacts"). Generally, antibodies comprise six HVRs; three in the VH (H1, H2, H3), and three in the VL (L1, L2, L3). HVRs as denoted herein include (a) hypervariable loops occurring at amino acid residues 26-32 (L1), 50-52 (L2), 91-96 (L3), 26-32 (H1), 53-55 (H2), and 96-101 (H3) (Chothia, C. and Lesk, A. M., J. Mol. Biol. 196 (1987) 901-917);

(b) CDRs occurring at amino acid residues 24-34 (L1), 50-56 (L2), 89-97 (L3), 31-35b (H1), 50-65 (H2), and 95-102 (H3) (Kabat, E. A. et al., Sequences of Proteins of Immunological Interest, 5th ed. Public Health Service, National Institutes of Health, Bethesda, Md. (1991), NIH Publication 91-3242.);

(c) antigen contacts occurring at amino acid residues 27c-36 (L1), 46-55 (L2), 89-96 (L3), 30-35b (H1), 47-58 (H2), and 93-101 (H3) (MacCallum et al. J. Mol. Biol. 262: 732-745 (1996)); and (d) combinations of (a), (b), and/or (c), including HVR amino acid residues 46-56 (L2), 47-56 (L2), 48-56 (L2), 49-56 (L2), 26-35 (H1), 26-35b (H1), 49-65 (H2), 93-102 (H3), and 94-102 (H3).

Unless otherwise indicated, HVR residues and other residues in the variable domain (e.g., FR residues) are numbered herein according to the Kabat EU index numbering system (Kabat et al., supra).

An "individual" or "subject" is a mammal. Mammals include, but are not limited to, domesticated animals (e.g. cows, sheep, cats, dogs, and horses), primates (e.g., humans and non-human primates such as monkeys), rabbits, and rodents (e.g., mice and rats). In certain embodiments, the individual or subject is a human.

An "isolated" antibody is one which has been separated from a component of its natural environment. In some embodiments, an antibody is purified to greater than 95% or 99% purity as determined by, for example, electrophoretic (e.g., SDS-PAGE, isoelectric focusing (IEF), capillary electrophoresis) or chromatographic (e.g., size-exclusion chromatography or ion exchange or reverse phase HPLC). For review of methods for assessment of antibody purity, see, e.g., Flatman, S. et al., J. Chrom. B 848 (2007) 79-87.

An "isolated" nucleic acid refers to a nucleic acid molecule that has been separated from a component of its natural environment. An isolated nucleic acid includes a nucleic acid molecule contained in cells that ordinarily contain the nucleic acid molecule, but the nucleic acid molecule is present extrachromosomally or at a chromosomal location that is different from its natural chromosomal location.

The term "monoclonal antibody" as used herein refers to an antibody obtained from a population of substantially homogeneous antibodies, i.e., the individual antibodies comprising the population are identical and/or bind the same epitope, except for possible variant antibodies, e.g., containing naturally occurring mutations or arising during production of a monoclonal antibody preparation, such variants generally being present in minor amounts. In contrast to polyclonal antibody preparations, which typically include different antibodies directed against different determinants (epitopes), each monoclonal antibody of a monoclonal antibody preparation is directed against a single determinant on an antigen. Thus, the modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by a variety of techniques, including but not limited to the hybridoma method, recombinant DNA methods, phage-display methods, and methods utilizing transgenic animals containing all or part of the human immunoglobulin loci, such methods and other exemplary methods for making monoclonal antibodies being described herein.

"Native antibodies" refer to naturally occurring immunoglobulin molecules with varying structures. For example, native IgG antibodies are heterotetrameric glycoproteins of about 150,000 daltons, composed of two identical light chains and two identical heavy chains that are disulfide-bonded. From N- to C-terminus, each heavy chain has a variable region (VH), also called a variable heavy domain or a heavy chain variable domain, followed by three constant domains (CH1, CH2, and CH3). Similarly, from N- to C-terminus, each light chain has a variable region (VL), also called a variable light domain or a light chain variable domain, followed by a constant light (CL) domain. The light chain of an antibody may be assigned to one of two types, called kappa (κ) and lambda (λ), based on the amino acid sequence of its constant domain.

The term "package insert" is used to refer to instructions customarily included in commercial packages of therapeutic products, that contain information about the indications, usage, dosage, administration, combination therapy, contraindications and/or warnings concerning the use of such therapeutic products.

"Percent (%) amino acid sequence identity" with respect to a reference polypeptide sequence is defined as the percentage of amino acid residues in a candidate sequence that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for aligning sequences, including any algorithms needed to achieve maximal alignment over the full length of the sequences being compared. For purposes herein, however, % amino acid sequence identity values are generated using the sequence comparison computer program ALIGN-2. The ALIGN-2 sequence comparison computer program was authored by Genentech, Inc., and the source code has been filed with user documentation in the U.S. Copyright Office, Washington D.C., 20559, where it is registered under U.S. Copyright Registration No. TXU510087. The ALIGN-2 program is publicly available from Genentech, Inc., South San Francisco, Calif., or may be compiled from the source code. The ALIGN-2 program should be compiled for use on a UNIX operating system, including digital UNIX V4.0D. All sequence comparison parameters are set by the ALIGN-2 program and do not vary.

In situations where ALIGN-2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows:

$$100 \text{ times the fraction } X/Y$$

where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. Unless specifically stated otherwise, all % amino acid sequence identity values used herein are obtained as described in the immediately preceding paragraph using the ALIGN-2 computer program.

The term "pharmaceutical formulation" refers to a preparation which is in such form as to permit the biological activity of an active ingredient contained therein to be effective, and which contains no additional components which are unacceptably toxic to a subject to which the formulation would be administered.

A "pharmaceutically acceptable carrier" refers to an ingredient in a pharmaceutical formulation, other than an active ingredient, which is nontoxic to a subject. A pharmaceutically acceptable carrier includes, but is not limited to, a buffer, excipient, stabilizer, or preservative.

The term "peptidic linker" as used herein denotes a peptide with amino acid sequences, which is in one embodiment of synthetic origin. The peptidic linker is in one embodiment a peptide with an amino acid sequence with a length of at least 30 amino acids, in one embodiment with a length of 32 to 50 amino acids. In one embodiment the peptidic linker is a peptide with an amino acid sequence with a length of 32 to 40 amino acids. In one embodiment the peptidic linker is (G×S)n with G=glycine, S=serine, (x=3, n=8, 9 or 10) or (x=4 and n=6, 7 or 8), in one embodiment with x=4, n=6 or 7, in one embodiment with x=4, n=7. In one embodiment the peptidic linker is $(G_4S)_6G_2$.

The term "recombinant antibody" denotes all antibodies (chimeric, humanized and human) that are prepared, expressed, created or isolated by recombinant means. This includes antibodies isolated from a host cell such as a NS0 or CHO cell or from an animal (e.g. a mouse) that is transgenic for human immunoglobulin genes or antibodies expressed using a recombinant expression vector transfected into a host cell. Such recombinant antibodies have variable and constant regions in a rearranged form. The recombinant antibodies as reported herein can be subjected to in vivo somatic hypermutation. Thus, the amino acid sequences of the VH and VL regions of the recombinant antibodies are sequences that, while derived from and related to human germ line VH and VL sequences, may not naturally exist within the human antibody germ line repertoire in vivo.

As used herein, "treatment" (and grammatical variations thereof such as "treat" or "treating") refers to clinical intervention in an attempt to alter the natural course of the individual being treated, and can be performed either for prophylaxis or during the course of clinical pathology. Desirable effects of treatment include, but are not limited to, preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis. In some embodiments, antibodies or Fc-region fusion polypeptides as reported herein are used to delay development of a disease or to slow the progression of a disease.

The term "valent" as used within the current application denotes the presence of a specified number of binding sites in a (antibody) molecule. As such, the terms "bivalent", "tetravalent", and "hexavalent" denote the presence of two binding site, four binding sites, and six binding sites, respectively, in a (antibody) molecule. The bispecific antibodies as reported herein are in one preferred embodiment "bivalent".

The term "variable region" or "variable domain" refer to the domain of an antibody heavy or light chain that is involved in binding of the antibody to its antigen. The variable domains of the heavy chain and light chain (VH and VL, respectively) of an antibody generally have similar structures, with each domain comprising four framework regions (FRs) and three hypervariable regions (HVRs) (see, e.g., Kindt, T. J. et al. Kuby Immunology, 6th ed., W.H. Freeman and Co., N.Y. (2007), page 91). A single VH or VL domain may be sufficient to confer antigen-binding specificity. Furthermore, antibodies that bind a particular antigen may be isolated using a VH or VL domain from an antibody that binds the antigen to screen a library of complementary VL or VH domains, respectively. See, e.g., Portolano, S. et al., J. Immunol. 150 (1993) 880-887; Clackson, T. et al., Nature 352 (1991) 624-628).

The term "ocular vascular disease" includes, but is not limited to intraocular neovascular syndromes such as diabetic retinopathy, diabetic macular edema, retinopathy of prematurity, neovascular glaucoma, retinal vein occlusions, central retinal vein occlusions, macular degeneration, age-related macular degeneration, retinitis pigmentosa, retinal angiomatous proliferation, macular telangectasia, ischemic retinopathy, iris neovascularization, intraocular neovascularization, corneal neovascularization, retinal neovascularization, choroidal neovascularization, and retinal degeneration (see e.g. Garner, A., Vascular diseases, In: Pathobiology of ocular disease, A dynamic approach, Garner, A., and Klintworth, G. K., (eds.), 2nd edition, Marcel Dekker, New York (1994), pp. 1625-1710).

The term "vector", as used herein, refers to a nucleic acid molecule capable of propagating another nucleic acid to which it is linked. The term includes the vector as a self-replicating nucleic acid structure as well as the vector incorporated into the genome of a host cell into which it has been introduced. Certain vectors are capable of directing the expression of nucleic acids to which they are operatively linked. Such vectors are referred to herein as "expression vectors".

The term "with (the) mutation IHH-AAA" as used herein refers to the combination of the mutations I253A (Ile253Ala), H310A (His310Ala), and H435A (His435Ala) and the term "with (the) mutation HHY-AAA" as used herein refers to the combination of the mutations H310A (His310Ala), H433A (His433Ala), and Y436A (Tyr436Ala) and the term "with (the) mutation YTE" as used herein refers to the combination of mutations M252Y (Met252Tyr), S254T (Ser254Thr), and T256E (Thr256Glu) in the constant heavy chain region of IgG1 or IgG4 subclass, wherein the numbering is according to the EU Index of Kabat.

The term "with (the) mutations P329G LALA" as used herein refers to the combination of the mutations L234A (Leu234Ala), L235A (Leu235Ala) and P329G (Pro329Gly) in the constant heavy chain region of IgG1 subclass, wherein the numbering is according to the EU Index of Kabat. The term "with (the) mutation SPLE" as used herein refers to the combination of the mutations S228P (Ser228Pro) and L235E (Leu235Glu) in the constant heavy chain region of IgG4 subclass, wherein the numbering is according to the EU Index of Kabat. The term "with (the) mutation SPLE and P239G" as used herein refers to the combination of the mutations S228P (Ser228Pro), L235E (Leu235Glu) and P329G (Pro329Gly) in the constant heavy chain region of IgG4 subclass, wherein the numbering is according to the EU Index of Kabat.

II. The Current Invention

The invention is based, at least in part, on the finding that the FcRn-binding of an antibody or Fc-region fusion polypeptide can be modified by altering amino acid residues at non-corresponding positions in the individual Fc-region polypeptides as these alterations act together in the modification of the FcRn-binding. Fc-regions, antibodies and Fc-region fusion polypeptides as reported herein are useful, e.g., for the treatment of diseases in which tailor-made systemic retention times are required.

Herein are reported variant Fc-regions that have modified FcRn binding properties compared to a corresponding wild-type Fc-region. These variant Fc-regions contain specific amino acid mutations in the CH2- and/or CH3-domain. It has been found that these mutations when used either alone or in combination in the same or in both heavy chains of an Fc-region allow to tailor-design the in vivo half-live of the variant Fc-region.

A. The Neonatal Fc-Receptor (FcRn)

The neonatal Fc-receptor (FcRn) is important for the metabolic fate of antibodies of the IgG class in vivo. The FcRn functions to salvage wild-type IgG from the lysosomal degradation pathway, resulting in reduced clearance and increased half-life. It is a heterodimeric protein consisting of two polypeptides: a 50 kDa class I major histocompatibility complex-like protein (α-FcRn) and a 15 kDa β2-microglobulin (β2m). FcRn binds with high affinity to the CH2-CH3 portion of the Fc-region of an antibody of the class IgG. The interaction between an antibody of the class IgG and the FcRn is pH dependent and occurs in a 1:2 stoichiometry, i.e. one IgG antibody molecule can interact with two FcRn molecules via its two heavy chain Fc-region polypeptides (see e.g. Huber, A. H., et al., J. Mol. Biol. 230 (1993) 1077-1083).

Thus, an IgGs in vitro FcRn binding properties/characteristics are indicative of its in vivo pharmacokinetic properties in the blood circulation.

In the interaction between the FcRn and the Fc-region of an antibody of the IgG class different amino acid residues of the heavy chain CH2- and CH3-domain are participating. The amino acid residues interacting with the FcRn are located approximately between EU position 243 and EU position 261, approximately between EU position 275 and EU position 293, approximately between EU position 302 and EU position 319, approximately between EU position 336 and EU position 348, approximately between EU position 367 and EU position 393, at EU position 408, and approximately between EU position 424 and EU position 440. More specifically the following amino acid residues according to the EU numbering of Kabat are involved in the interaction between the Fc-region and the FcRn: F243, P244, P245 P, K246, P247, K248, D249, T250, L251, M252, I253, S254, R255, T256, P257, E258, V259, T260, C261, F275, N276, W277, Y278, V279, D280, V282, E283, V284, H285, N286, A287, K288, T289, K290, P291, R292, E293, V302, V303, S304, V305, L306, T307, V308, L309, H310, Q311, D312, W313, L314, N315, G316, K317, E318, Y319, I336, S337, K338, A339, K340, G341, Q342, P343, R344, E345, P346, Q347, V348, C367, V369, F372, Y373, P374, S375, D376, I377, A378, V379, E380, W381, E382, S383, N384, G385, Q386, P387, E388, N389, Y391, T393, S408, S424, C425, S426, V427, M428, H429, E430, A431, L432, H433, N434, H435, Y436, T437, Q438, K439, and S440.

Site-directed mutagenesis studies have proven that the critical binding sites in the Fc-region of IgGs for FcRn are Histidine 310, Histidine 435, and Isoleucine 253 and to a lesser extent Histidine 433 and Tyrosine 436 (see e.g. Kim, J. K., et al., Eur. J. Immunol. 29 (1999) 2819-2825; Raghavan, M., et al., Biochem. 34 (1995) 14649-14657; Medesan, C., et al., J. Immunol. 158 (1997) 2211-2217).

Methods to increase IgG binding to FcRn have been performed by mutating IgG at various amino acid residues: Threonine 250, Methionine 252, Serine 254, Threonine 256, Threonine 307, Glutamic acid 380, Methionine 428, Histidine 433, and Asparagine 434 (see Kuo, T. T., et al., J. Clin. Immunol. 30 (2010) 777-789).

In some cases antibodies with reduced half-life in the blood circulation are desired. For example, drugs for intravitreal application should have a long half-live in the eye and a short half-life in the circulation of the patient. Such antibodies also have the advantage of increased exposure to a disease site, e.g. in the eye.

Different mutations that influence the FcRn binding and therewith the half-live in the blood circulation are known. Fc-region residues critical to the mouse Fc-mouse FcRn interaction have been identified by site-directed mutagenesis (see e.g. Dall'Acqua, W. F., et al. J. Immunol 169 (2002) 5171-5180). Residues I253, H310, H433, N434, and H435 (EU numbering according to Kabat) are involved in the interaction (Medesan, C., et al., Eur. J. Immunol. 26 (1996) 2533-2536; Firan, M., et al., Int. Immunol. 13 (2001) 993-1002; Kim, J. K., et al., Eur. J. Immunol. 24 (1994) 542-548). Residues I253, H310, and H435 were found to be critical for the interaction of human Fc with murine FcRn (Kim, J. K., et al., Eur. J. Immunol. 29 (1999) 2819-2825). Residues M252Y, S254T, T256E have been described by Dall'Acqua et al. to improve FcRn binding by protein-protein interaction studies (Dall'Acqua, W. F., et al. J. Biol. Chem. 281 (2006) 23514-23524). Studies of the human Fc-human FcRn complex have shown that residues I253, S254, H435, and Y436 are crucial for the interaction (Firan, M., et al., Int. Immunol. 13 (2001) 993-1002; Shields, R. L., et al., J. Biol. Chem. 276 (2001) 6591-6604). In Yeung, Y. A., et al. (J. Immunol. 182 (2009) 7667-7671) various mutants of residues 248 to 259 and 301 to 317 and 376 to 382 and 424 to 437 have been reported and examined. Exemplary mutations and their effect on FcRn binding are listed in the following Table.

TABLE

| mutation | effect on FcRn binding | half-live in the circulation | reference |
| --- | --- | --- | --- |
| H285<br>H310Q/H433N<br>(murine IgG1) | reduced<br>(murine) | reduced<br>(in mouse) | Kim, J. K.,<br>Scand. J.<br>Immunol.<br>40 (1994)<br>457-465 |
| I253A<br>H310A<br>H435A<br>H436A<br>(murine IgG1) | reduced<br>(murine) | reduced<br>(in mouse) | Ghetie, V.<br>and Ward, E. S.,<br>Immunol.<br>Today 18<br>(1997) 592-598 |
| T252L/T254S/T256F<br>T252A/T254S/T256A<br>(murine IgG1) | increased<br>(murine) | increased<br>(in mouse) | Ghetie, V.<br>and Ward, E. S.,<br>Immunol.<br>Today 18<br>(1997) 592-598 |

TABLE-continued

| mutation | effect on FcRn binding | half-live in the circulation | reference |
| --- | --- | --- | --- |
| I253A<br>H310A<br>H435A<br>H436A<br>H433A/N434Q<br>(murine IgG1) | reduced (murine) | reduced (in mouse) | Medesan, C., et al., J. Immunol. 158 (1997) 2211-2217 |
| I253A<br>H310A<br>H435A<br>H435R<br>(human IgG1) | H310A: <0.1 rel. binding to muFcRn (murine) | reduced (in mouse) | Kim, J. K., Eur. J. Immunol. 29 (1999) 2819-2825 |
| H433A<br>(human IgG1) | 1.1 rel. binding to muFcRn, 0.4 rel. binding hu FcRn (murine) | | Kim, J. K., Eur. J. Immunol. 29 (1999) 2819-2825 |
| I253A<br>S254A<br>H435A<br>Y436A<br>(human IgG1) | reduced <0.1 relative binding to huFcRn | reduced | Shields, R. L., et al., J. Biol. Chem. 276 (2001) 6591-6604 |
| R255A<br>K288A<br>L309A<br>S415A<br>H433A<br>(human IgG1) | reduced (human) | reduced | Shields, R. L., et al., J. Biol. Chem. 276 (2001) 6591-6604 |
| P238A<br>T256A<br>E272A<br>V305A<br>T307A<br>Q311A<br>D312A<br>K317A<br>D376A<br>A378Q<br>E380A<br>E382A<br>S424A<br>N434A<br>K288A/N434A<br>E380A/N434A<br>T307A/E380A/N434A<br>(human IgG1) | increased (human) | increased | Shields, R. L., et al., J. Biol. Chem. 276 (2001) 6591-6604 |
| H435A<br>(humanized IgG1) | reduced <0.1 rel. binding to huFcRn | reduced | Firan, M., et al., Int. Immunol. 13 (2001) 993-1002 |
| I253A (no binding)<br>M252W<br>M252Y<br>M252Y/T256Q<br>M252F/T256D<br>N434F/Y436H<br>M252Y/S254T/T256E<br>G385A/Q386P/N389S<br>H433K/N434F/Y436H<br>H433R/N434Y/Y436H<br>G385R/Q386T/P387R/N389P<br>M252Y/S254T/T256E/H433K/N434F/Y436H<br>M252Y/S254T/T256E/G385R/Q386T/P387R/N389P<br>(human IgG1) | increased (murine and human) | reduced (in mouse) | Dall'Acqua, J. Immunol. 169 (2002) 5171-5180 |
| M428L<br>T250Q/M428L<br>(human IgG2) | increased (human) | increased (in monkey) | Hinton, P. R., et al., J. Biol. Chem. 279 (2004) 6213-6216 |

TABLE-continued

| mutation | effect on FcRn binding | half-live in the circulation | reference |
|---|---|---|---|
| M252Y/S254T/T256E + H433K/N434F (human IgG) | increased (human) | increased (in mouse) | Vaccaro, C., et al., Nat. Biotechnol. 23 (2005) 1283-1288 |
| T307A/E380A/N434A (chimeric IgG1) | increased | increased in transgenic mouse | Pop, L. M., et al., Int. Immunopharmacol. 5 (2005) 1279-1290 |
| T250Q<br>E380A<br>M428L<br>N434A<br>K288A/N434A<br>E380A/N434A<br>T307A/E380A/N434A<br>(human IgG1) | increased (human) | increased in transgenic mouse | Petkova, S. B., et al., Int. Immunol 18 (2006) 1759-1769 |
| I253A (human IgG1) | reduced (human) | reduced in transgenic mouse | Petkova, S. B., et al., Int. Immunol 18 (2006) 1759-1769 |
| S239D/A330L/I332E M252Y/S254T/T256E (humanized) | increased (human and Cynomolgus) | increased in Cynomolgus | Dall'Acqua, W. F., et al., J. Biol. Chem. 281 (2006) 23514-23524 |
| T250Q<br>M428L<br>T250Q/M428L<br>(human IgG1) | increased (human) | increased in Rhesus apes | Hinton, P. R., et al., J. Immunol. 176 (2006) 346-356 |
| T250Q/M428L P257I/Q311I (humanized IgG1) | increased (mouse and Cynomolgus) | no change in Cynomolgus increased in mouse | Datta-Mannan, A., et al., J. Biol. Chem. 282 (2007) 1709-1717 |
| P257I/Q311I<br>P257I/N434H<br>D376V/N434H<br>(humanized IgG1) | increased at pH 6 (human, Cynomolgus, mouse) | reduced in mice P257I/N434H reduced in Cynomolgus | Datta-Mannan, A., et al., Drug Metab. Dispos. 35 (2007) 86-94 |
| abrogate FcRn binding:<br>I253<br>H310<br>H433<br>H435<br>reduce FcRn binding:<br>Y436<br>increased FcRn binding:<br>T250<br>N252<br>S254<br>T256<br>T307<br>M428<br>N434 | increased and reduced | reducing the binding ability of IgG for FcRn reduces its serum persistence; a higher-affinity FcRn-IgG interaction prolongs the half-lives of IgG and Fc-coupled drugs in the serum | Ropeenian, D. C. and Akilesh, S., Nat. Rev. Immunol. 7 (2007) 715-725 |
| N434A<br>T307Q/N434A<br>T307Q/N434S<br>V308P/N434A<br>T307Q/E380A/N434A<br>(human IgG1) | increased (Cynomolgus monkey) | increased in Cynomolgus monkey | Yeung, Y. A., et al., Cancer Res. 70 (2010) 3269-3277 |

TABLE-continued

| mutation | effect on FcRn binding | half-live in the circulation | reference |
|---|---|---|---|
| 256P<br>280K<br>339T<br>385H<br>428L<br>434W/Y/F/A/H<br>(human IgG) | increased at neutral pH | | WO 2011/122011 |

It has been found that one mutation one-sided in one Fc-region polypeptide is sufficient to weaken the binding to an Fc receptor significantly. The more mutations are introduced into the Fc-region the weaker the binding to the FcRn becomes. But one-sided asymmetric mutations are not sufficient to completely inhibit FcRn binding. Mutations on both sides are necessary to completely inhibit FcRn binding.

Thus, the variant (human) IgG class Fc-region is a heterodimer and the pairing of the first (heavy chain) Fc-region polypeptide and the second (heavy chain) Fc-region polypeptide to form a functional Fc-region results in the formation of a heterodimer.

The results of a symmetric engineering of an IgG1 Fc-region to influence FcRn binding is shown in the following table (alignment of mutations and retention time on an FcRn-affinity chromatography column).

TABLE

| effector function influencing mutations | FcRn-binding influencing mutation 1 | FcRn-binding influencing mutation 2 | FcRn-binding influencing mutation 3 | FcRn-affinity column retention time [min] |
|---|---|---|---|---|
| L234A/L235A/P329G | — | — | — | 45.3 |
| L234A/L235A/P329G | I253A | H310A | H435A | 2.3 |
| L234A/L235A/P329G | I253A | — | — | 2.7 |
| L234A/L235A/P329G | — | H310A | — | 2.4 |
| L234A/L235A/P329G | — | — | H435A | 2.7 |
| L234A/L235A/P329G | I253A | H310A | — | 2.3 |
| L234A/L235A/P329G | I253A | — | H435A | 2.3 |
| L234A/L235A/P329G | — | H310A | H435A | 2.4 |
| L234A/L235A/P329G | — | H310A | Y436A | 2.3 |
| L234A/L235A/P329G | H310A | H433A | Y436A | 2.4 |
| L234A/L235A/P329G | — | — | Y436A | 41.3 |

Retention times below 3 minutes correspond to no binding as the substance is in the flow-through (void peak).

The single mutation H310A is the most silent symmetrical mutation to delete any FcRn-binding.

The symmetric single mutation I253A and H435A result in a relative shift of retention time of 0.3-0.4 min. This can be generally regarded as a non-detectable binding.

The single mutation Y436A results in detectable interaction strength to the FcRn affinity column. Without being bound by this theory this mutation could have an FcRn mediated half-life which can be differentiated from a zero interaction such as the combination of the I253A, H310A and H435A mutations (IHH-AAA mutation).

The results obtained with a symmetrically modified anti-HER2 antibody are presented in the following table (see WO 2006/031370 for reference).

TABLE

| mutation | retention time [min] |
|---|---|
| I253H | no binding |
| M252D | no binding |
| S254D | no binding |
| R255D | 41.4 |
| M252H | 43.6 |
| K288E | 45.2 |
| L309H | 45.5 |
| E258H | 45.6 |
| T256H | 46.0 |
| K290H | 46.2 |
| D98E | 46.2 |
| wild-type | 46.3 |
| K317H | 46.3 |
| Q311H | 46.3 |
| E430H | 46.4 |
| T307H | 47.0 |
| N434H | 52.0 |

The Fc-region in the Fc-region fusion polypeptide confers the above described characteristics to its fusion partner. The fusion partner can be any molecules having a biological activity whose in vivo half-live shall be reduced or increased, i.e. whose in vivo half-live shall be clearly defined and tailor-made for its intended application.

Fc-region fusion polypeptides may comprise e.g. a variant (human) IgG class Fc-region as reported herein and a receptor protein that binds to a target including a ligand, such as, for example, TNFR-Fc-region fusion polypeptide (TNFR=human tumor necrosis factor receptor), or IL-1R-Fc-region fusion polypeptide (IL-1R=human interleukin-1 receptor), or VEGFR-Fc-region fusion polypeptides (VEGFR=human vascular endothelial growth factor receptor), or ANG2R-Fc-region fusion polypeptides (ANG2R=human angiopoietin 2 receptor).

Fc-region fusion polypeptides may comprise e.g. a variant (human) IgG class Fc-region as reported herein and an antibody fragment that binds to a target including, such as, for example, an antibody Fab fragment, scFvs (see e.g. Nat. Biotechnol. 23 (2005) 1126-1136), or domain antibodies (dAbs) (see e.g. WO 2004/058821, WO 2003/002609).

Fc-region fusion polypeptides may comprise e.g. a variant (human) IgG class Fc-region as reported herein and a receptor ligand (either naturally occurring or artificial).

B. Exemplary Fc-Regions and Antibodies Comprising these Fc-Regions

In one aspect, the invention provides Fc-regions that have modified FcRn-binding, i.e. these Fc-regions bind to human FcRn with an affinity higher or lower than an Fc-region having no mutations affecting the FcRn-binding.

In one aspect, the invention provides isolated antibodies that have modified FcRn-binding, i.e. these antibodies bind to human FcRn with an affinity higher or lower than an antibody having no mutations affecting the FcRn-binding.

One aspect as reported herein is an antibody comprising a (variant) Fc-region comprising a first Fc-region polypeptide and a second Fc-region polypeptide,
wherein
a) the first Fc-region polypeptide and the second Fc-region polypeptide are derived from the same human Fc-region polypeptide, and
b) the first Fc-region polypeptide has been modified in that its amino acid sequence differs from the second Fc-region polypeptide amino acid sequence at least at one corresponding position according to the Kabat EU index numbering system, and the second Fc-region polypeptide has been modified in that its amino acid sequence differs from the first Fc-region polypeptide amino acid sequence at least at one corresponding position according to the Kabat EU index numbering system, whereby the modified position in the first Fc-region polypeptide and the modified position in the second Fc-region polypeptide are different, and
c) the Fc-region has a different affinity to a human Fc-receptor compared to an Fc-region that comprises as first and second Fc-region polypeptide the human Fc-region polypeptide of a) (i.e. that has the same amino acid residues as the human Fc-region polypeptide of a) at corresponding positions according to the Kabat EU index numbering system).

In one embodiment of all aspects as reported herein either the first Fc-region polypeptide or the second Fc-region polypeptide or both Fc-region polypeptides comprise one of the following mutations or combination of mutations:
T307H, or
Q311H, or
E430 H, or
N434H, or
T307H and Q311H, or
T307H and E430H, or
T307H and N434A, or
T307H and N434H, or
T307Q and Q311H, or
T307Q and E430H, or
T307Q and N434H, or
T307H and Q311H and E430H and N434A, or
T307H and Q311H and E430H and N434H, or
T307H and Q311H and E430H and N434Y, or
T307Q and Q311H and E430H and N434A, or
T307Q and Q311H and E430H and N434H, or
T307Q and Q311H and E430H and N434Y, or
T307Q and V308P and N434Y and Y436H, or
T307H and M252Y and S254T and T256E, or
T307Q and M252Y and S254T and T256E, or
Q311H and M252Y and S254T and T256E, or
E430 H and M252Y and S254T and T256E, or
N434H and M252Y and S254T and T256E, or
T307H and Q311H and M252Y and S254T and T256E, or
T307H and E430H and M252Y and S254T and T256E, or
T307H and N434A and M252Y and S254T and T256E, or
T307H and N434H and M252Y and S254T and T256E, or
T307Q and Q311H and M252Y and S254T and T256E, or
T307Q and E430H and M252Y and S254T and T256E, or
T307Q and N434H and M252Y and S254T and T256E, or
T307H and Q311H and E430H and N434A and M252Y and S254T and T256E, or
T307H and Q311H and E430H and N434H and M252Y and S254T and T256E, or
T307H and Q311H and E430H and N434Y and M252Y and S254T and T256E, or
T307Q and Q311H and E430H and N434A and M252Y and S254T and T256E, or
T307Q and Q311H and E430H and N434H and M252Y and S254T and T256E, or
T307Q and Q311H and E430H and N434Y and M252Y and S254T and T256E, or
T307Q and V308P and N434Y and Y436H and M252Y and S254T and T256E.

In one embodiment of all aspects as reported herein the first Fc-region polypeptide comprise independently of the second Fc-region polypeptide one of the following mutations or combination of mutations:
T307H, or
Q311H, or
E430 H, or
N434H, or
T307H and Q311H, or
T307H and E430H, or
T307H and N434A, or
T307H and N434H, or
T307Q and Q311H, or
T307Q and E430H, or
T307Q and N434H, or
M252Y and S254T and T256E, or
I253A and H310A and H435A, or
H310A and H433A and Y436A, or
T307H and Q311H and E430H and N434A, or
T307H and Q311H and E430H and N434H, or
T307H and Q311H and E430H and N434Y, or
T307Q and Q311H and E430H and N434A, or
T307Q and Q311H and E430H and N434H, or
T307Q and Q311H and E430H and N434Y, or
T307Q and V308P and N434Y and Y436H, or
T307H and M252Y and S254T and T256E, or
Q311H and M252Y and S254T and T256E, or
E430 H and M252Y and S254T and T256E, or
N434H and M252Y and S254T and T256E, or
T307H and Q311H and M252Y and S254T and T256E, or
T307H and E430H and M252Y and S254T and T256E, or
T307H and N434A and M252Y and S254T and T256E, or
T307H and N434H and M252Y and S254T and T256E, or
T307Q and Q311H and M252Y and S254T and T256E, or
T307Q and E430H and M252Y and S254T and T256E, or
T307Q and N434H and M252Y and S254T and T256E, or
T307H and Q311H and E430H and N434A and M252Y and S254T and T256E, or
T307H and Q311H and E430H and N434H and M252Y and S254T and T256E, or
T307H and Q311H and E430H and N434Y and M252Y and S254T and T256E, or T307Q and V308P and N434Y and Y436H and M252Y and S254T and T256E, or
T307Q and V308P and N434Y and Y436H and M252Y and S254T and T256E,
and
the second Fc-region polypeptide comprise independently of the first Fc-region polypeptide one of the following mutations or combination of mutations
T307H, or
T307Q, or
Q311H, or
E430 H, or
N434H, or
T307H and Q311H, or
T307H and E430H, or
T307H and N434A, or
T307H and N434H, or
T307Q and Q311H, or
T307Q and E430H, or
T307Q and N434H, or
T307H and Q311H and E430H and N434A, or
T307H and Q311H and E430H and N434H, or
T307H and Q311H and E430H and N434Y, or
T307Q and Q311H and E430H and N434A, or
T307Q and Q311H and E430H and N434H, or
T307Q and Q311H and E430H and N434Y, or
T307Q and V308P and N434Y and Y436H, or
T307H and M252Y and S254T and T256E, or
Q311H and M252Y and S254T and T256E, or
E430 H and M252Y and S254T and T256E, or
N434H and M252Y and S254T and T256E.

In one embodiment of all aspects as reported herein the first Fc-region polypeptide comprises
one of the following combinations of mutations:
none, or
M252Y and S254T and T256E, or
I253A and H310A and H435A, or
H310A and H433A and Y436A,
and
one of the following mutations or combination of mutations:
none
T307H, or
T307Q, or
Q311H, or
E430 H, or
N434H, or
T307H and Q311H, or
T307H and E430H, or
T307H and N434A, or
T307H and N434H, or
T307Q and Q311H, or
T307Q and E430H, or
T307Q and N434H, or
T307Q and N434A, or
T307H and Q311H and E430H and N434A, or
T307H and Q311H and E430H and N434H, or
T307H and Q311H and E430H and N434Y, or
T307Q and Q311H and E430H and N434A, or
T307Q and Q311H and E430H and N434H, or
T307Q and Q311H and E430H and N434Y, or
T307Q and V308P and N434Y and Y436H,
and the second Fc-region polypeptide comprises
one of the following mutations or combination of mutations:
none, if the first Fc-region polypeptide comprises at least one mutation, or
T307H, or
T307Q, if the first Fc-region polypeptide does not comprises solely the T307Q mutation, or
Q311H, or
E430 H, or
N434H, or
T307H and Q311H, or
T307H and E430H, or
T307H and N434H, or
T307Q and Q311H, or
T307Q and E430H, or
T307Q and N434H, or
T307Q and N434A, or
M252Y and S254T and T256E, if the first Fc-region polypeptide does not comprises solely the combination M252Y and S254T and T256E of mutations, or
I253A and H310A and H435A, if the first Fc-region polypeptide does not comprises solely the combination I253A and H310A and H435A of mutations, or
H310A and H433A and Y436A, if the first Fc-region polypeptide does not comprises solely the combination H310A and H433A and Y436A of mutations, or
T307H and Q311H and E430H and N434A, or
T307H and Q311H and E430H and N434H, or
T307H and Q311H and E430H and N434Y, or
T307Q and Q311H and E430H and N434A, or
T307Q and Q311H and E430H and N434H, or
T307Q and Q311H and E430H and N434Y, or
T307Q and V308P and N434Y and Y436H.

In one preferred embodiment the first Fc-region polypeptide comprises the mutations I253A and H310A and H435A and the second Fc-region polypeptide comprises the mutations M252Y and S254T and T256E.

In one preferred embodiment the first Fc-region polypeptide comprises the mutations I253A and H310A and H435A and the second Fc-region polypeptide comprises the mutations M252Y and S254T and T256E and T307Q and N434Y.

In one preferred embodiment the first Fc-region polypeptide comprises the mutations I253A and H310A and H435A and the second Fc-region polypeptide comprises the mutations M252Y and S254T and T256E and T307Q and V308P and N434Y and Y436H.

In one preferred embodiment the first Fc-region polypeptide comprises the mutations T307H and Q311H and E430H and N434H and the second Fc-region polypeptide comprises the mutations M252Y and S254T and T256E.

In one preferred embodiment the first Fc-region polypeptide comprises the mutations T307H and N434H and the second Fc-region polypeptide comprises the mutations M252Y and S254T and T256E.

In one preferred embodiment the first Fc-region polypeptide comprises the mutations T307Q and N434A and the second Fc-region polypeptide comprises the mutations M252Y and S254T and T256E.

In one preferred embodiment the first Fc-region polypeptide comprises the mutations T250Q and M428L and the second Fc-region polypeptide comprises the mutations M252Y and S254T and T256E.

In one preferred embodiment the first Fc-region polypeptide comprises the mutations T307Q and N434H and the second Fc-region polypeptide comprises the mutations M252Y and S254T and T256E and T307Q and N434H.

In one preferred embodiment the first Fc-region polypeptide comprises the mutations T307H and Q311H and E430H and N434H and the second Fc-region polypeptide comprises the mutations T307H and Q311H and E430H and N434H.

In one preferred embodiment the first Fc-region polypeptide comprises the mutations T307H and N434H and the second Fc-region polypeptide comprises the mutations T307H and N434H.

In one preferred embodiment the first Fc-region polypeptide comprises the mutations T307H and N434H and M252Y and S254T and T256E and the second Fc-region polypeptide comprises the mutations T307H and N434H and M252Y and S254T and T256E.

In one preferred embodiment the first Fc-region polypeptide comprises the mutation N434H and the second Fc-region polypeptide comprises the mutation N434H.

In one preferred embodiment the first Fc-region polypeptide comprises the mutations T307Q and N434A.

In one preferred embodiment the first Fc-region polypeptide comprises the mutations T307H and N434H.

In one preferred embodiment the first Fc-region polypeptide comprises the mutations T307H and N434H and M252Y and S254T and T256E.

In one preferred embodiment the first Fc-region polypeptide comprises the mutation N434H.

In one embodiment of all aspects the Fc-region is a variant (human) IgG class Fc-region. In one embodiment the variant (human) IgG class Fc-region is an IgG class heterodimeric Fc-region.

In one embodiment of all aspects the pairing of the first Fc-region polypeptide and the second Fc-region polypeptide to form a (functional) Fc-region results in the formation of a heterodimer.

In one embodiment the human Fc-region polypeptide is a human Fc-region polypeptide of the IgG1 subclass or of the IgG4 subclass.

In one embodiment the human Fc-region polypeptide is a human Fc-region polypeptide of the IgG1 subclass which further comprises the mutations L234A, L235A and P329G.

In one embodiment the human Fc-region polypeptide is a human Fc-region polypeptide of the IgG4 subclass which further comprises the mutations S228P and L235E.

In one embodiment the first Fc-region polypeptide further comprises the mutations S354C and T366W and the second Fc-region polypeptide further comprises the mutations Y349C, T366S, L368A and Y407V.

In one embodiment the bispecific antibody is characterized in that the Fc-region of iii) is of human IgG1 subclass. In one embodiment the bispecific antibody is characterized in that the Fc-region of human IgG1 subclass further comprises the mutations L234A, L235A and P329G (numbering according to EU Index of Kabat).

In one embodiment the bispecific antibody is characterized in that the Fc-region of iii) is of human IgG4 subclass. In one embodiment the bispecific antibody is characterized in that the Fc-region of human IgG4 subclass further comprises the mutations S228P and L235E (numbering according to EU Index of Kabat). In one embodiment the bispecific antibody is characterized in that the Fc-region of human IgG4 subclass further comprises the mutations S228P, L235E and P329G (numbering according to EU Index of Kabat).

Still further aspects as reported herein are a pharmaceutical formulation comprising the bispecific antibody, the pharmaceutical formulation for use in the treatment of ocular vascular diseases, the use of the bispecific antibody for the manufacture of a medicament for the treatment of ocular vascular diseases, a method of treatment of patient suffering from ocular vascular diseases by administering the bispecific antibody to a patient in the need of such treatment. In one embodiment the bispecific antibody or the pharmaceutical formulation comprising the bispecific antibody is administered via intravitreal application.

A further aspect according to the current invention is a nucleic acid molecule encoding a heavy and/or light chain of a bispecific antibody as reported herein.

The invention further provides expression vectors containing the nucleic acid as reported herein capable of expressing the nucleic acid in a prokaryotic or eukaryotic host cell, and host cells containing such vectors for the recombinant production of a bispecific antibody as reported herein.

The invention further comprises a prokaryotic or eukaryotic host cell comprising a vector as reported herein.

The invention further comprises a method for the production of a bispecific antibody as reported herein, characterized by expressing a nucleic acid as reported herein in a prokaryotic or eukaryotic host cell and recovering the bispecific antibody from the cell or the cell culture supernatant. One embodiment is a method for the preparation of a bispecific antibody as reported herein comprising the steps of a) transforming a host cell with vectors comprising nucleic acid molecules encoding the antibody;
b) culturing the host cell under conditions that allow synthesis of the antibody; and
c) recovering the antibody from the culture.

The invention further comprises the antibody obtained by such method for the production of a bispecific antibody.

The antibodies as reported herein have highly valuable properties due to their specific modifications in the Fc-region causing a benefit for a patient suffering from ocular vascular diseases. They show high stability in the intravitreal environment and slow diffusion from the eye (compared to smaller antibody fragments without a constant heavy chain region), where the actual disease is located and treated (so treatment schedule may potentially be improved compared to non-IgG like antibodies like e.g. Fab and (Fab)$_2$ fragments). The antibodies as reported herein are cleared on the other hand quite rapidly from serum (which is highly desired to reduce potential side effects arising from systemic exposure). Surprisingly they also show lower viscosity (compared to versions without the combination of the mutations I253A, H310A and H435A in the constant region) and are therefore especially useful for intravitreal application through thin needles during the treatment of eye diseases (for such application typically thin needles are used and high viscosity makes an appropriate application rather difficult). The lower viscosity also allows higher concentration formulations.

Also surprisingly the antibodies as reported herein show a lower aggregation tendency during storage (compared to versions without the combination of the mutations I253A, H310A and H435A in the Fc-region) which is critical for intravitreal application in the eye (as an aggregation in the eye can lead to complications during such treatment).

The bispecific antibodies as reported herein show good efficacy in inhibition of vascular diseases.

In certain embodiments, the bispecific antibodies as reported herein due to their specific modifications in the constant region (e.g. P329G LALA) show valuable properties like no binding to/of Fcgamma receptors which reduces the risk of side effects like thrombosis and/or unwanted cell death (due to e.g. ADCC).

In one embodiment as reported herein the bispecific antibody as reported herein is bivalent.

In one embodiment the antibody heavy chain variable domain (VH) and the antibody light chain variable domain (VL) of the heavy and light chain of the second full length antibody are further stabilized by the introduction of a disulfide bond between the following positions: heavy chain variable domain position 44 and light chain variable domain position 100 (numbering according to Kabat (Kabat, E. A., et al., Sequences of Proteins of Immunological Interest, 5th ed., Public Health Service, National Institutes of Health, Bethesda, Md. (1991)). Techniques to introduce disulfide bridges for stabilization are described e.g. in WO 94/029350, Rajagopal, V., et al, Prot. Eng. 10 (1997) 1453-1459, Kobayashi et al., Nuclear Medicine & Biology 25 (1998) 387-393, and Schmidt, M., et al., Oncogene 18 (1999) 1711-1721.

In one embodiment the CH3 domains of the bispecific, bivalent antibody as reported herein are altered by the "knob-into-holes" technology which is described in detail with several examples e.g. in WO 96/027011, Ridgway J. B., et al., Protein Eng. 9 (1996) 617-621, and Merchant, A. M., et al., Nat. Biotechnol. 16 (1998) 677-681. In this method the interaction surfaces of the two CH3 domains are altered to increase the heterodimerization of both heavy chains containing these two CH3 domains. Each of the two CH3 domains (of the two heavy chains) can be the "knob-chain" while the other is the "hole-chain". The introduction of a disulfide bridge further stabilizes the heterodimers (Merchant, A. M, et al., Nature Biotech. 16 (1998) 677-681, Atwell, S., et al. J. Mol. Biol. 270 (1997) 26-35) and increases the yield.

In one preferred embodiment of all aspects as reported herein the bispecific antibodies is characterized in that
the CH3 domain of one heavy chain and the CH3 domain of the other heavy chain each meet at an interface which comprises an original interface between the antibody CH3 domains,
wherein the interface is altered to promote the formation of the bispecific antibody, wherein the alteration is characterized in that:
a) the CH3 domain of one heavy chain is altered,
so that within the original interface the CH3 domain of one heavy chain that meets the original interface of the CH3 domain of the other heavy chain within the bispecific antibody
an amino acid residue is replaced with an amino acid residue having a larger side chain volume, thereby generating a protuberance within the interface of the CH3 domain of one heavy chain which is positionable in a cavity within the interface of the CH3 domain of the other heavy chain,
and
b) the CH3 domain of the other heavy chain is altered,
so that within the original interface of the second CH3 domain that meets the original interface of the first CH3 domain within the bispecific antibody
an amino acid residue is replaced with an amino acid residue having a smaller side chain volume, thereby generating a cavity within the interface of the second CH3 domain within which a protuberance within the interface of the first CH3 domain is positionable.

Thus, the antibody according to invention is in one preferred embodiment characterized in that
the CH3 domain of the heavy chain of the full length antibody of a) and the CH3 domain of the heavy chain of the full length antibody of b) each meet at an interface which comprises an alteration in the original interface between the antibody's CH3 domains, wherein
i) in the CH3 domain of one heavy chain
an amino acid residue is replaced with an amino acid residue having a larger side chain volume, thereby generating a protuberance within the interface of the CH3 domain of one heavy chain which is positionable in a cavity within the interface of the CH3 domain of the other heavy chain,
and wherein
ii) in the CH3 domain of the other heavy chain
an amino acid residue is replaced with an amino acid residue having a smaller side chain volume, thereby generating a cavity within the interface of the second CH3 domain within which a protuberance within the interface of the first CH3 domain is positionable.

In one preferred embodiment the amino acid residue having a larger side chain volume is selected from the group consisting of arginine (R), phenylalanine (F), tyrosine (Y), tryptophan (W).

In one preferred embodiment the amino acid residue having a smaller side chain volume is selected from the group consisting of alanine (A), serine (S), threonine (T), valine (V).

In one embodiment both CH3 domains are further altered by the introduction of a cysteine residue (C) in the corresponding positions of each CH3 domain such that a disulfide bridge between both CH3 domains can be formed.

In one embodiment, the bispecific antibody comprises a T366W mutation in the CH3 domain of the "knobs chain" and the T366S, L368A and Y407V mutations in the CH3 domain of the "hole-chain". An additional interchain disulfide bridge between the CH3 domains can also be used (Merchant, A. M, et al., Nature Biotech 16 (1998) 677-681) e.g. by introducing a Y349C or S354C mutation into the CH3 domain of the "knobs chain" and a Y439C or E356C or S354C mutation into the CH3 domain of the "hole chain".

In one embodiment the bispecific antibody as reported herein comprises the mutation Y349C or S354C and the mutation T366W in one of the two CH3 domains and the mutations S354C or E356C or Y349C and the mutations T366S, L368A and Y407V in the other of the two CH3 domains. In one preferred embodiment the bispecific antibody comprises the Y349C, T366W mutations in one of the two CH3 domains and the S354C, T366S, L368A, Y407V mutations in the other of the two CH3 domains (the additional Y349C mutation in one CH3 domain and the additional S354C mutation in the other CH3 domain forming a interchain disulfide bridge) (numbering according to EU index of Kabat (Kabat, E. A., et al., Sequences of Proteins of Immunological Interest, 5th ed., Public Health Service, National Institutes of Health, Bethesda, Md. (1991)). In one preferred embodiment the bispecific antibody comprises the S354C, T366W mutations in one of the two CH3 domains and the Y349C, T366S, L368A, Y407V mutations in the other of the two CH3 domains (the additional Y349C mutation in one CH3 domain and the additional S354C mutation in the other CH3 domain forming a interchain disulfide bridge) (numbering according to EU index of Kabat (Kabat, E. A., et al., Sequences of Proteins of Immunological Interest, 5th ed., Public Health Service, National Institutes of Health, Bethesda, Md. (1991)).

But also other knobs-in-holes technologies as described by EP 1 870 459 A1, can be used alternatively or additionally. Thus another example for the bispecific antibody are the R409D and K370E mutations in the CH3 domain of the "knobs chain" and the D399K and E357K mutations in the CH3 domain of the "hole chain" (numbering according to EU index of Kabat (Kabat, E. A., et al., Sequences of Proteins of Immunological Interest, 5th ed., Public Health Service, National Institutes of Health, Bethesda, Md. (1991)).

In another embodiment the bispecific antibody comprises a T366W mutation in the CH3 domain of the "knobs chain" and the T366S, L368A and Y407V mutations in the CH3 domain of the "hole chain" and additionally the R409D, K370E mutations in the CH3 domain of the "knobs chain" and the D399K, E357K mutations in the CH3 domain of the "hole chain".

In one embodiment the bispecific antibody comprises the Y349C, T366W mutations in one of the two CH3 domains and the S354C, T366S, L368A and Y407V mutations in the other of the two CH3 domains, or the bispecific antibody comprises the Y349C, T366W mutations in one of the two CH3 domains and the S354C, T366S, L368A and Y407V mutations in the other of the two CH3 domains and additionally the R409D, K370E mutations in the CH3 domain of the "knobs chain" and the D399K, E357K mutations in the CH3 domain of the "hole chain".

In one embodiment the bispecific antibody comprises the S354C, T366W mutations in one of the two CH3 domains and the Y349C, T366S, L368A, Y407V mutations in the other of the two CH3 domains, or the bispecific antibody comprises the S354C, T366W mutations in one of the two CH3 domains and the Y349C, T366S, L368A and Y407V mutations in the other of the two CH3 domains and additionally the R409D, K370E mutations in the CH3 domain of the "knobs chain" and the D399K, E357K mutations in the CH3 domain of the "hole chain".

An antigen-binding site of the bispecific antibody as reported herein contains six complementarity determining regions (CDRs) which contribute in varying degrees to the affinity of the binding site for its antigen. There are three heavy chain variable domain CDRs (CDRH1, CDRH2 and CDRH3) and three light chain variable domain CDRs (CDRL1, CDRL2 and CDRL3). The extent of CDR and framework regions (FRs) is determined by comparison to a compiled database of amino acid sequences in which those regions have been defined according to variability among the sequences.

In one embodiment of all aspects the antibody does not specifically bind to the human FcRn. In one embodiment of all aspects the antibody in addition does specifically bind to Staphylococcal protein A.

In one embodiment of all aspects the antibody does not specifically bind to the human FcRn. In one embodiment of all aspects the antibody in addition does not specifically bind to Staphylococcal protein A In one embodiment of all aspects the first polypeptide further comprises the mutations Y349C, T366S, L368A and Y407V ("hole") and the second polypeptide comprises the mutations S354C and T366W ("knob").

In one embodiment of all aspects the first polypeptide further comprises the mutations S354C, T366S, L368A and Y407V ("hole") and the second polypeptide comprises the mutations Y349C and T366W ("knob").

In one embodiment of all aspects the Fc-region polypeptides are of the human IgG1 subclass. In one embodiment the first Fc-region polypeptide and the second Fc-region polypeptide further comprise the mutations L234A and L235A. In one embodiment the first Fc-region polypeptide and the second Fc-region polypeptide further comprise the mutation P329G.

In one embodiment of all aspects the Fc-region polypeptides are of the human IgG4 subclass. In one embodiment the first Fc-region polypeptide and the second Fc-region polypeptide further comprise the mutations S228P and L235E. In one embodiment the first Fc-region polypeptide and the second Fc-region polypeptide further comprise the mutation P329G.

The antibody as reported herein is produced by recombinant means. Thus, one aspect as reported herein is a nucleic acid encoding the antibody as reported herein and a further aspect is a cell comprising the nucleic acid encoding an antibody as reported herein. Methods for recombinant production are widely known in the state of the art and comprise protein expression in prokaryotic and eukaryotic cells with subsequent isolation of the antibody and usually purification to a pharmaceutically acceptable purity. For the expression of the antibodies as aforementioned in a host cell, nucleic acids encoding the respective (modified) light and heavy chains are inserted into expression vectors by standard methods. Expression is performed in appropriate prokaryotic or eukaryotic host cells like CHO cells, NS0 cells, SP2/0 cells, HEK293 cells, COS cells, PER.C6 cells, yeast, or E. coli cells, and the antibody is recovered from the cells (cultivation supernatant or cells after lysis). General methods for recombinant production of antibodies are well-known in the state of the art and described, for example, in the review articles of Makrides, S. C., Protein Expr. Purif. 17 (1999) 183-202, Geisse, S., et al., Protein Expr. Purif. 8 (1996) 271-282, Kaufman, R. J., Mol. Biotechnol. 16 (2000) 151-160, and Werner, R. G., Drug Res. 48 (1998) 870-880.

Accordingly one aspect as reported herein is a method for the preparation of a bispecific antibody as reported herein, comprising the steps of a) transforming a host cell with vectors comprising nucleic acid molecules encoding the antibody, b) culturing the host cell under conditions that allow synthesis of the antibody, and c) recovering the antibody from the culture.

In one embodiment the recovering step under c) includes the use of a light chain constant domain specific capture reagent (which e.g. specific for the kappa or the lambda constant light chain, depending on whether a kappa or a lambda light chain is contained in the bispecific antibody). In one embodiment this light chain specific capture reagent is used in a bind-and-elute-mode. Examples of such light chain constant domain specific capture reagents are e.g. KappaSelect™ and LambdaFabSelect™ (available from GE Healthcare/BAC), which are based on a highly rigid agarose base matrix that allows high flow rates and low back pressure at large scale. These materials contain a ligand that binds to the constant region of the kappa or the lambda light chain, respectively (i.e. fragments lacking the constant region of the light chain will not bind). Both are therefore capable of binding other target molecules containing the constant region of the light chain, for example, IgG, IgA and IgM. The ligands are attached to the matrix via a long hydrophilic spacer arm to make them easily available for binding to the target molecule. They are based on a single-chain antibody fragment that is screened for either human Ig kappa or lambda.

In one embodiment the recovering step under c) includes the use of an Fc-region specific capture reagent. In one embodiment the Fc-region specific capture reagent is used in a bind-and-elute-mode. Examples of such Fc-region specific capture reagents are e.g. Staphylococcus protein A-based affinity chromatography materials.

The bispecific antibodies are suitably separated from the culture medium by conventional immunoglobulin purification procedures such as, for example, affinity chromatography (protein A-Sepharose, or KappaSelect™, LambdaFabSelect™), hydroxylapatite chromatography, gel electrophoresis, or dialysis.

DNA and RNA encoding the monoclonal antibodies is readily isolated and sequenced using conventional procedures. B-cells or hybridoma cells can serve as a source of such DNA and RNA. Once isolated, the DNA may be inserted into expression vectors, which are then transfected into host cells such as HEK 293 cells, CHO cells, or myeloma cells that do not otherwise produce immunoglobulin protein, to obtain the synthesis of recombinant monoclonal antibodies in the host cells.

Some of the molecules as reported herein provide ease of isolation/purification by comprising Fc-regions that are differentially modified, wherein at least one of the modifications results in i) a differential affinity of the molecule for (Staphylococcal) protein A and ii) a differential affinity of the molecule for the human FcRn, and the molecule is isolable from a disrupted cell, from medium, or from a mixture of molecules based on its affinity for protein A.

Purification of antibodies is performed in order to eliminate cellular components or other contaminants, e.g. other cellular nucleic acids or proteins, by standard techniques, including alkaline/SDS treatment, CsCl banding, column chromatography, agarose gel electrophoresis, and others well known in the art (see e.g. Ausubel, F., et al., ed. Current Protocols in Molecular Biology, Greene Publishing and Wiley Interscience, New York (1987)). Different methods are well established and widespread used for protein purification, such as affinity chromatography with microbial proteins (e.g. protein A or protein G affinity chromatography), ion exchange chromatography (e.g. cation exchange (carboxymethyl resins), anion exchange (amino ethyl resins) and mixed-mode exchange), thiophilic adsorption (e.g. with beta-mercaptoethanol and other SH ligands), hydrophobic interaction or aromatic adsorption chromatography (e.g. with phenyl-sepharose, aza-arenophilic resins, or m-aminophenylboronic acid), metal chelate affinity chromatography (e.g. with Ni(II)- and Cu(II)-affinity material), size exclusion chromatography, and electrophoretical methods (such as gel electrophoresis, capillary electrophoresis) (Vijayalakshmi, M. A., Appl. Biochem. Biotech. 75 (1998) 93-102).

One aspect as reported herein is a pharmaceutical formulation comprising an antibody as reported herein. Another aspect as reported herein is the use of an antibody as reported herein for the manufacture of a pharmaceutical formulation. A further aspect as reported herein is a method for the manufacture of a pharmaceutical formulation comprising an antibody as reported herein. In another aspect, a formulation is provided, e.g. a pharmaceutical formulation, containing an antibody as reported herein, formulated together with a pharmaceutical carrier.

A formulation of the present invention can be administered by a variety of methods known in the art. As will be appreciated by the skilled artisan, the route and/or mode of administration will vary depending upon the desired results. To administer a compound as reported herein by certain routes of administration, it may be necessary to coat the compound with, or co-administer the compound with a material to prevent its inactivation. For example, the compound may be administered to a subject in an appropriate carrier, for example, liposomes, or a diluent. Pharmaceutically acceptable diluents include saline and aqueous buffer solutions. Pharmaceutical carriers include sterile aqueous solutions or dispersions and sterile powders for the extemporaneous preparation of sterile injectable solutions or dispersion. The use of such media and agents for pharmaceutically active substances is known in the art.

Many possible modes of delivery can be used, including, but not limited to intraocular application or topical application. In one embodiment the application is intraocular and includes, but it's not limited to, subconjunctival injection, intracanieral injection, injection into the anterior chamber via the termporai limbus, intrastromal injection, intracorneal injection, subretinal injection, aqueous humor injection, subtenon injection or sustained delivery device, intravitreal injection (e.g., front, mid or back vitreal injection). In one embodiment the application is topical and includes, but it's not limited to eye drops to the cornea.

In one embodiment the bispecific antibody or pharmaceutical formulation as reported herein is administered via intravitreal application, e.g. via intravitreal injection. This can be performed in accordance with standard procedures known in the art (see, e.g., Ritter et al., J. Clin. Invest. 116 (2006) 3266-3276, Russelakis-Carneiro et al., Neuropathol. Appl. Neurobiol. 25 (1999) 196-206, and Wray et al., Arch. Neurol. 33 (1976) 183-185).

In some embodiments, therapeutic kits as reported herein can contain one or more doses of a (bispecific) antibody present in a pharmaceutical formulation described herein, a suitable device for intravitreal injection of the pharmaceutical formulation, and an instruction detailing suitable subjects and protocols for carrying out the injection. In these embodiments, the formulations are typically administered to the subject in need of treatment via intravitreal injection. This can be performed in accordance with standard procedures known in the art (see, e.g., Ritter et al., J. Clin. Invest. 116 (2006) 3266-3276, Russelakis-Carneiro et al., Neuropathol. Appl. Neurobiol. 25 (1999) 196-206, and Wray et al., Arch. Neurol. 33 (1976) 183-185).

The formulations may also contain adjuvants such as preservatives, wetting agents, emulsifying agents and dispersing agents. Prevention of presence of microorganisms may be ensured both by sterilization procedures, supra, and by the inclusion of various antibacterial and antifungal agents, for example, paraben, chlorobutanol, phenol, sorbic acid, and the like. It may also be desirable to include isotonic agents, such as sugars, sodium chloride, and the like into the formulations. In addition, prolonged absorption of the injectable pharmaceutical form may be brought about by the inclusion of agents which delay absorption such as aluminum monostearate and gelatin.

Regardless of the route of administration selected, the compounds as reported herein, which may be used in a suitable hydrated form, and/or the pharmaceutical formulations as reported herein, are formulated into pharmaceutically acceptable dosage forms by conventional methods known to those of skill in the art.

Actual dosage levels of the active ingredients in the pharmaceutical formulations as reported herein may be varied so as to obtain an amount of the active ingredient which is effective to achieve the desired therapeutic response for a particular patient, formulation, and mode of administration, without being toxic to the patient. The selected dosage level will depend upon a variety of pharmacokinetic factors including the activity of the particular formulations employed, the route of administration, the time of administration, the rate of excretion of the particular compound being employed, the duration of the treatment, other drugs, compounds and/or materials used in combination with the particular formulations employed, the age, sex, weight, condition, general health and prior medical history of the patient being treated, and like factors well known in the medical arts.

The formulation must be sterile and fluid to the extent that the formulation is deliverable by syringe. In addition to water, the carrier preferably is an isotonic buffered saline solution.

Proper fluidity can be maintained, for example, by use of coating such as lecithin, by maintenance of required particle size in the case of dispersion and by use of surfactants. In many cases, it is preferable to include isotonic agents, for example, sugars, polyalcohols such as mannitol or sorbitol, and sodium chloride in the formulation.

The formulation can comprise an ophthalmic depot formulation comprising an active agent for subconjunctival administration. The ophthalmic depot formulation comprises microparticles of essentially pure active agent, e.g., the bispecific antibody as reported herein. The microparticles comprising the bispecific antibody as reported herein can be embedded in a biocompatible pharmaceutically acceptable polymer or a lipid encapsulating agent. The depot formulations may be adapted to release all of substantially all the active material over an extended period of time. The polymer or lipid matrix, if present, may be adapted to degrade sufficiently to be transported from the site of administration after release of all or substantially all the active agent. The depot formulation can be liquid formulation, comprising a pharmaceutical acceptable polymer and a dissolved or dispersed active agent. Upon injection, the polymer forms a depot at the injections site, e.g. by gelifying or precipitating.

Another aspect as reported herein is the bispecific antibody as reported herein for use in the treatment of ocular vascular diseases.

Another aspect as reported herein is the pharmaceutical formulation as reported herein for use in the treatment of ocular vascular diseases.

Another aspect as reported herein is the use of an antibody as reported herein for the manufacture of a medicament for the treatment of ocular vascular disease.

Another aspect as reported herein is method of treatment of patient suffering from ocular vascular diseases by administering an antibody as reported herein to a patient in the need of such treatment.

It is herewith expressly stated that the term "comprising" as used herein comprises the term "consisting of". Thus, all aspects and embodiments that contain the term "comprising" are likewise disclosed with the term "consisting of".
Modifications In a further aspect, an Fc-region or antibody as reported herein as well as according to any of the above embodiments may incorporate any of the features, singly or in combination, as described in Sections 1-6 below:
1. Antibody Affinity In one embodiment, Kd is measured using a BIACORE® surface plasmon resonance assay. For example, an assay using a BIACORE®-2000 or a BIACORE®-3000 (GE Healthcare Inc., Piscataway, N.J.) is performed at 25° C. with immobilized antigen CM5 chips at ~10 response units (RU). In one embodiment, carboxymethylated dextran biosensor chips (CM5, GE Healthcare Inc.) are activated with N-ethyl-N'-(3-dimethylaminopropyl)-carbodiimide hydrochloride (EDC) and N-hydroxysuccinimide (NETS) according to the supplier's instructions. Antigen is diluted with 10 mM sodium acetate, pH 4.8, to 5 μg/mL (~0.2 μM) before injection at a flow rate of 5 μL/minute to achieve approximately 10 response units (RU) of coupled protein. Following the injection of antigen, 1 M ethanolamine is injected to block non-reacted groups. For kinetics measurements, twofold serial dilutions of Fab (0.78 nM to 500 nM) are injected in PBS with 0.05% polysorbate 20 (TWEEN-20™) surfactant (PBST) at 25° C. at a flow rate of approximately 25 μL/min. Association rates ($k_{on}$) and dissociation rates ($k_{off}$) are calculated using a simple one-to-one Langmuir binding model (BIACORE® Evaluation Software version 3.2) by simultaneously fitting the association and dissociation sensorgrams. The equilibrium dissociation constant (Kd) is calculated as the ratio $k_{off}/k_{on}$ (see, e.g., Chen, Y. et al., J. Mol. Biol. 293 (1999) 865-881). If the on-rate exceeds $10^6$ $M^{-1}$ $s^{-1}$ by the surface plasmon resonance assay above, then the on-rate can be determined by using a fluorescent quenching technique that measures the increase or decrease in fluorescence emission intensity (excitation=295 nm; emission=340 nm, 16 nm band-pass) at 25° C. of a 20 nM anti-antigen antibody (Fab form) in PBS, pH 7.2, in the presence of increasing concentrations of antigen as measured in a spectrometer, such as a stop-flow equipped spectrophotometer (Aviv Instruments) or a 8000-series SLM-AMINCO™ spectrophotometer (ThermoSpectronic) with a stirred cuvette.
2. Chimeric and Humanized Antibodies In certain embodiments, an antibody provided herein is a chimeric antibody. Certain chimeric antibodies are described, e.g., in U.S. Pat. No. 4,816,567; and Morrison, S. L., et al., Proc. Natl. Acad. Sci. USA 81 (1984) 6851-6855). In one example, a chimeric antibody comprises a non-human variable region (e.g., a variable region derived from a mouse, rat, hamster, rabbit, or non-human primate, such as a monkey) and a human constant region. In a further example, a chimeric antibody is a "class switched" antibody in which the class or subclass has been changed from that of the parent antibody. Chimeric antibodies include antigen-binding fragments thereof.

In certain embodiments, a chimeric antibody is a humanized antibody. Typically, a non-human antibody is humanized to reduce immunogenicity to humans, while retaining the specificity and affinity of the parental non-human antibody. Generally, a humanized antibody comprises one or more variable domains in which HVRs, e.g., CDRs, (or portions thereof) are derived from a non-human antibody, and FRs (or portions thereof) are derived from human antibody sequences. A humanized antibody optionally will also comprise at least a portion of a human constant region. In some embodiments, some FR residues in a humanized antibody are substituted with corresponding residues from a non-human antibody (e.g., the antibody from which the HVR residues are derived), e.g., to restore or improve antibody specificity or affinity.

Humanized antibodies and methods of making them are reviewed, e.g., in Almagro, J. C. and Fransson, J., Front. Biosci. 13 (2008) 1619-1633, and are further described, e.g., in Riechmann, I., et al., Nature 332 (1988) 323-329; Queen, C., et al., Proc. Natl. Acad. Sci. USA 86 (1989) 10029-10033; U.S. Pat. Nos. 5,821,337, 7,527,791, 6,982,321, and 7,087,409; Kashmiri, S. V., et al., Methods 36 (2005) 25-34 (describing specificity determining region (SDR) grafting); Padlan, E. A., Mol. Immunol. 28 (1991) 489-498 (describing "resurfacing"); Dall'Acqua, W. F. et al., Methods 36 (2005) 43-60 (describing "FR shuffling"); Osbourn, J. et al., Methods 36 (2005) 61-68; and Klimka, A. et al., Br. J. Cancer 83 (2000) 252-260 (describing the "guided selection" approach to FR shuffling).

Human framework regions that may be used for humanization include but are not limited to: framework regions selected using the "best-fit" method (see, e.g., Sims, M. J., et al., J. Immunol. 151 (1993) 2296-2308; framework regions derived from the consensus sequence of human antibodies of a particular subgroup of light or heavy chain variable regions (see, e.g., Carter, P., et al., Proc. Natl. Acad. Sci. USA 89 (1992) 4285-4289; and Presta, L. G., et al., J. Immunol. 151 (1993) 2623-2632); human mature (somatically mutated) framework regions or human germline framework regions (see, e.g., Almagro, J. C. and Fransson, J., Front. Biosci. 13 (2008) 1619-1633); and framework regions derived from screening FR libraries (see, e.g., Baca, M. et al., J. Biol. Chem. 272 (1997) 10678-10684 and Rosok, M. J. et al., J. Biol. Chem. 271 (19969 22611-22618).

3. Human Antibodies

In certain embodiments, an antibody provided herein is a human antibody. Human antibodies can be produced using various techniques known in the art. Human antibodies are described generally in van Dijk, M. A. and van de Winkel, J. G., Curr. Opin. Pharmacol. 5 (2001) 368-374 and Lonberg, N., Curr. Opin. Immunol. 20 (2008) 450-459.

Human antibodies maybe prepared by administering an immunogen to a transgenic animal that has been modified to produce intact human antibodies or intact antibodies with human variable regions in response to antigenic challenge. Such animals typically contain all or a portion of the human immunoglobulin loci, which replace the endogenous immunoglobulin loci, or which are present extrachromosomally or integrated randomly into the animal's chromosomes. In such transgenic mice, the endogenous immunoglobulin loci have generally been inactivated. For review of methods for obtaining human antibodies from transgenic animals, see Lonberg, N., Nat. Biotech. 23 (2005) 1117-1125. See also, e.g., U.S. Pat. Nos. 6,075,181 and 6,150,584 describing XENOMOUSE™ technology; U.S. Pat. No. 5,770,429 describing HuMAB® technology; U.S. Pat. No. 7,041,870 describing K-M MOUSE® technology, and US 2007/0061900, describing VELOCIMOUSE® technology). Human variable regions from intact antibodies generated by such animals may be further modified, e.g., by combining with a different human constant region.

Human antibodies can also be made by hybridoma-based methods. Human myeloma and mouse-human heteromyeloma cell lines for the production of human monoclonal antibodies have been described (see, e.g., Kozbor, D., J. Immunol. 133 (1984) 3001-3005; Brodeur, B. R., et al., Monoclonal Antibody Production Techniques and Applications, Marcel Dekker, Inc., New York (1987), pp. 51-63; and Boerner, P., et al., J. Immunol. 147 (1991) 86-95). Human antibodies generated via human B-cell hybridoma technology are also described in Li, J. et al., Proc. Natl. Acad. Sci. USA 103 (2006) 3557-3562. Additional methods include those described, for example, in U.S. Pat. No. 7,189,826 (describing production of monoclonal human IgM antibodies from hybridoma cell lines) and Ni, J., Xiandai Mianyixue 26 (2006) 265-268 (describing human-human hybridomas). Human hybridoma technology (Trioma technology) is also described in Vollmers, H. P. and Brandlein, S., Histology and Histopathology 20 (2005) 927-937 and Vollmers, H. P. and Brandlein, S., Methods and Findings in Experimental and Clinical Pharmacology 27 (2005) 185-191.

Human antibodies may also be generated by isolating Fv clone variable domain sequences selected from human-derived phage display libraries. Such variable domain sequences may then be combined with a desired human constant domain. Techniques for selecting human antibodies from antibody libraries are described below.

4. Library-Derived Antibodies

Antibodies as reported herein may be isolated by screening combinatorial libraries for antibodies with the desired activity or activities. For example, a variety of methods are known in the art for generating phage display libraries and screening such libraries for antibodies possessing the desired binding characteristics. Such methods are reviewed, e.g., in Hoogenboom, H. R. et al., Methods in Molecular Biology 178 (2001) 1-37 and further described, e.g., in the McCafferty, J. et al., Nature 348 (1990) 552-554; Clackson, T. et al., Nature 352 (1991) 624-628; Marks, J. D. et al., J. Mol. Biol. 222 (1992) 581-597; Marks, J. D. and Bradbury, A., Methods in Molecular Biology 248 (2003) 161-175; Sidhu, S. S. et al., J. Mol. Biol. 338 (2004) 299-310; Lee, C. V. et al., J. Mol. Biol. 340 (2004) 1073-1093; Fellouse, F. A., Proc. Natl. Acad. Sci. USA 101 (2004) 12467-12472; and Lee, C. V. et al., J. Immunol. Methods 284 (2004) 119-132.

In certain phage display methods, repertoires of VH and VL genes are separately cloned by polymerase chain reaction (PCR) and recombined randomly in phage libraries, which can then be screened for antigen-binding phage as described in Winter, G., et al., Ann. Rev. Immunol. 12 (1994) 433-455. Phage typically display antibody fragments, either as single-chain Fv (scFv) fragments or as Fab fragments. Libraries from immunized sources provide high-affinity antibodies to the immunogen without the requirement of constructing hybridomas. Alternatively, the naive repertoire can be cloned (e.g., from human) to provide a single source of antibodies to a wide range of non-self and also self-antigens without any immunization as described by Griffiths, A. D., et al., EMBO J. 12 (1993) 725-734.

Finally, naive libraries can also be made synthetically by cloning non-rearranged V-gene segments from stem cells, and using PCR primers containing random sequence to encode the highly variable CDR3 regions and to accomplish rearrangement in vitro, as described by Hoogenboom, H. R. and Winter, G., J. Mol. Biol. 227 (1992) 381-388. Patent publications describing human antibody phage libraries include, for example: U.S. Pat. No. 5,750,373, and US 2005/0079574, US 2005/0119455, US 2005/0266000, US 2007/0117126, US 2007/0160598, US 2007/0237764, US 2007/0292936, and US 2009/0002360.

Antibodies or antibody fragments isolated from human antibody libraries are considered human antibodies or human antibody fragments herein.

5. Multispecific Antibodies

In certain embodiments, an antibody provided herein is a multispecific antibody, e.g. a bispecific antibody. Multispecific antibodies are monoclonal antibodies that have binding specificities for at least two different sites. Bispecific antibodies may also be used to localize cytotoxic agents to cells which express one or more of the target antigens. Bispecific antibodies can be prepared as full length antibodies or antibody fragments.

Techniques for making multispecific antibodies include, but are not limited to, recombinant co-expression of two immunoglobulin heavy chain-light chain pairs having different specificities (see Milstein, C. and Cuello, A. C., Nature 305 (1983) 537-540, WO 93/08829, and Traunecker, A., et al., EMBO J. 10 (1991) 3655-3659), and "knob-in-hole" engineering (see, e.g., U.S. Pat. No. 5,731,168). Multispecific antibodies may also be made by engineering electrostatic steering effects for making antibody Fc-heterodimeric molecules (WO 2009/089004); cross-linking two or more antibodies or fragments (see, e.g., U.S. Pat. No. 4,676,980, and Brennan, M. et al., Science 229 (1985) 81-83); using leucine zippers to produce bi-specific antibodies (see, e.g., Kostelny, S. A., et al., J. Immunol. 148 (1992) 1547-1553; using "diabody" technology for making bispecific antibody fragments (see, e.g., Holliger, P. et al., Proc. Natl. Acad. Sci. USA 90 (1993) 6444-6448); and using single-chain Fv (sFv) dimers (see, e.g. Gruber, M et al., J. Immunol. 152 (1994) 5368-5374); and preparing trispecific antibodies as described, e.g., in Tutt, A. et al., J. Immunol. 147 (1991) 60-69).

Engineered antibodies with three or more functional antigen binding sites, including "Octopus antibodies," are also included herein (see, e.g. US 2006/0025576).

The antibody or fragment herein also includes a "Dual Acting Fab" or "DAF" comprising an antigen binding site that binds to a first antigen as well as another, different antigen (see, US 2008/0069820, for example).

The antibody or fragment herein also includes multispecific antibodies described in WO 2009/080251, WO 2009/080252, WO 2009/080253, WO 2009/080254, WO 2010/112193, WO 2010/115589, WO 2010/136172, WO 2010/145792, and WO 2010/145793.

6. Fc-Region and Antibody Variants

In certain embodiments, amino acid sequence variants of the Fc-regions or antibodies provided herein are contemplated. For example, it may be desirable to improve the antigen binding affinity and/or other biological properties of the antibody. Amino acid sequence variants of an Fc-region or antibody may be prepared by introducing appropriate modifications into the nucleotide sequence encoding the antibody, or by peptide synthesis. Such modifications include, for example, deletions from, and/or insertions into and/or substitutions of residues within the amino acid sequences of the Fc-region or antibody. Any combination of deletion, insertion, and substitution can be made to arrive at the final construct, provided that the final construct possesses the desired characteristics, e.g., antigen-binding.

a) Substitution, Insertion, and Deletion Variants

In certain embodiments, Fc-region or antibody variants having one or more amino acid substitutions are provided. Sites of interest for substitutional mutagenesis include the HVRs and FRs. Conservative substitutions are shown in the Table below under the heading of "preferred substitutions". More substantial changes are provided in the following Table under the heading of "exemplary substitutions", and as further described below in reference to amino acid side chain classes. Amino acid substitutions may be introduced into an antibody of interest and the products screened for a desired activity, e.g., retained/improved antigen binding, decreased immunogenicity, or improved ADCC or CDC.

TABLE

| Original Residue | Exemplary Substitutions | Preferred Substitutions |
|---|---|---|
| Ala (A) | Val; Leu; Ile | Val |
| Arg (R) | Lys; Gln; Asn | Lys |
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |

TABLE-continued

| Original Residue | Exemplary Substitutions | Preferred Substitutions |
|---|---|---|
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Amino acids may be grouped according to common side-chain properties:
(1) hydrophobic: Norleucine, Met, Ala, Val, Leu, Ile;
(2) neutral hydrophilic: Cys, Ser, Thr, Asn, Gln;
(3) acidic: Asp, Glu;
(4) basic: His, Lys, Arg;
(5) residues that influence chain orientation: Gly, Pro;
(6) aromatic: Trp, Tyr, Phe.

Non-conservative substitutions will entail exchanging a member of one of these classes for another class.

One type of substitutional variant involves substituting one or more hypervariable region residues of a parent Fc-region or antibody (e.g. a humanized or human antibody). Generally, the resulting variant(s) selected for further study will have modifications (e.g., improvements) in certain biological properties (e.g., increased affinity, reduced immunogenicity) relative to the parent Fc-region or antibody and/or will have substantially retained certain biological properties of the parent Fc-region or antibody. An exemplary substitutional variant is an affinity matured antibody, which may be conveniently generated, e.g., using phage display-based affinity maturation techniques such as those described herein. Briefly, one or more HVR residues are mutated and the variant antibodies displayed on phage and screened for a particular biological activity (e.g. binding affinity).

Alterations (e.g., substitutions) may be made in HVRs, e.g., to improve antibody affinity. Such alterations may be made in HVR "hotspots," i.e., residues encoded by codons that undergo mutation at high frequency during the somatic maturation process (see, e.g., Chowdhury, P. S., Methods Mol. Biol. 207 (2008) 179-196), and/or residues that contact antigen, with the resulting variant VH or VL being tested for binding affinity. Affinity maturation by constructing and reselecting from secondary libraries has been described, e.g., in Hoogenboom, H. R. et al. in Methods in Molecular Biology 178 (2002) 1-37. In some embodiments of affinity maturation, diversity is introduced into the variable genes chosen for maturation by any of a variety of methods (e.g., error-prone PCR, chain shuffling, or oligonucleotide-directed mutagenesis). A secondary library is then created. The library is then screened to identify any antibody variants with the desired affinity. Another method to introduce diversity involves HVR-directed approaches, in which several HVR residues (e.g., 4-6 residues at a time) are randomized. HVR residues involved in antigen binding may be specifically identified, e.g., using alanine scanning mutagenesis or modeling. CDR-H3 and CDR-L3 in particular are often targeted.

In certain embodiments, substitutions, insertions, or deletions may occur within one or more HVRs so long as such alterations do not substantially reduce the ability of the antibody to bind antigen. For example, conservative alterations (e.g., conservative substitutions as provided herein) that do not substantially reduce binding affinity may be made in HVRs. Such alterations may, for example, be outside of antigen contacting residues in the HVRs. In certain embodiments of the variant VH and VL sequences provided above, each HVR either is unaltered, or contains no more than one, two or three amino acid substitutions.

A useful method for identification of residues or regions of an Fc-region or antibody that may be targeted for mutagenesis is called "alanine scanning mutagenesis" as described by Cunningham, B. C. and Wells, J. A., Science 244 (1989) 1081-1085. In this method, a residue or group of target residues (e.g., charged residues such as arg, asp, his, lys, and glu) are identified and replaced by a neutral or negatively charged amino acid (e.g., alanine or polyalanine) to determine whether the desired biological property, such as e.g. the interaction of the antibody with antigen, is affected. Further substitutions may be introduced at the amino acid locations demonstrating functional sensitivity to the initial substitutions. Alternatively, or additionally, a crystal structure of an Fc-region or antibody comprising complex to identify contact points can be used. Such contact residues and neighboring residues may be targeted or eliminated as candidates for substitution. Variants may be screened to determine whether they contain the desired properties.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an Fc-region or antibody with an N-terminal methionyl residue. Other insertional variants of the Fc-region or antibody molecule include the fusion to the N- or C-terminus of the Fc-region or antibody to an enzyme (e.g. for ADEPT) or a polypeptide which increases the serum half-life of the Fc-region or antibody.

b) Glycosylation Variants

In certain embodiments, an Fc-region or antibody provided herein is altered to increase or decrease the extent to which the Fc-region or antibody is glycosylated. Addition or deletion of glycosylation sites to an Fc-region or antibody may be conveniently accomplished by altering the amino acid sequence such that one or more glycosylation sites is created or removed.

Where the antibody comprises an Fc-region, the carbohydrate attached thereto may be altered. Native Fc-regions or antibodies produced by mammalian cells typically comprise a branched, biantennary oligosaccharide that is generally attached by an N-linkage to Asn297 of the CH2 domain of the Fc-region. See, e.g., Wright, A. and Morrison, S. L., TIBTECH 15 (1997) 26-32. The oligosaccharide may include various carbohydrates, e.g., mannose, N-acetyl glucosamine (GlcNAc), galactose, and sialic acid, as well as a fucose attached to a GlcNAc in the "stem" of the biantennary oligosaccharide structure. In some embodiments, modifications of the oligosaccharide in an Fc-region or antibody as reported herein may be made in order to create antibody variants with certain improved properties.

In one embodiment, antibody variants are provided having a carbohydrate structure that lacks fucose attached (directly or indirectly) to an Fc-region. For example, the amount of fucose in such antibody may be from 1% to 80%, from 1% to 65%, from 5% to 65% or from 20% to 40%. The amount of fucose is determined by calculating the average amount of fucose within the sugar chain at Asn297, relative to the sum of all glycostructures attached to Asn 297 (e. g. complex, hybrid and high mannose structures) as measured by MALDI-TOF mass spectrometry, as described in WO 2008/077546, for example. Asn297 refers to the asparagine residue located at about position 297 in the Fc-region (EU numbering of Fc-region residues); however, Asn297 may also be located about ±3 amino acids upstream or downstream of position 297, i.e., between positions 294 and 300, due to minor sequence variations in antibodies. Such fucosylation variants may have improved ADCC function. See, e.g., US 2003/0157108; US 2004/0093621. Examples of publications related to "defucosylated" or "fucose-deficient" antibody variants include: US 2003/0157108; WO 2000/61739; WO 2001/29246; US 2003/0115614; US 2002/0164328; US 2004/0093621; US 2004/0132140; US 2004/0110704; US 2004/0110282; US 2004/0109865; WO 2003/085119; WO 2003/084570; WO 2005/035586; WO 2005/035778; WO 2005/053742; WO 2002/031140; Okazaki, A. et al., J. Mol. Biol. 336 (2004) 1239-1249; Yamane-Ohnuki, N. et al., Biotech. Bioeng. 87 (2004) 614-622. Examples of cell lines capable of producing defucosylated antibodies include Lec13 CHO cells deficient in protein fucosylation (Ripka, J., et al., Arch. Biochem. Biophys. 249 (1986) 533-545; US 2003/0157108; and WO 2004/056312, especially at Example 11), and knockout cell lines, such as alpha-1,6-fucosyltransferase gene, FUT8, knockout CHO cells (see, e.g., Yamane-Ohnuki, N., et al., Biotech. Bioeng. 87 (2004) 614-622; Kanda, Y. et al., Biotechnol. Bioeng. 94 (2006) 680-688; and WO 2003/085107).

Fc-region or antibody variants are further provided with bisected oligosaccharides, e.g., in which a biantennary oligosaccharide attached to the Fc-region of the antibody is bisected by GlcNAc. Such Fc-region or antibody variants may have reduced fucosylation and/or improved ADCC function. Examples of such antibody variants are described, e.g., in WO 2003/011878; U.S. Pat. No. 6,602,684; and US 2005/0123546. Fc-region or antibody variants with at least one galactose residue in the oligosaccharide attached to the Fc-region are also provided. Such antibody variants may have improved CDC function. Such antibody variants are described, e.g., in WO 1997/30087; WO 1998/58964; and WO 1999/22764.

c) Fc-Region Variants

In certain embodiments, one or more further amino acid modifications may be introduced into the Fc-region provided herein, thereby generating an Fc-region variant. The Fc-region variant may comprise a human Fc-region sequence (e.g., a human IgG1, IgG2, IgG3 or IgG4 Fc-region) comprising an amino acid modification (e.g. a substitution/mutation) at one or more amino acid positions.

In certain embodiments, the invention contemplates an Fc-region variant that possesses some but not all effector functions, which make it a desirable candidate for applications in which the half-life of the Fc-region in vivo is important yet certain effector functions (such as CDC and ADCC) are unnecessary or deleterious. In vitro and/or in vivo cytotoxicity assays can be conducted to confirm the reduction/depletion of CDC and/or ADCC activities. For example, Fc receptor (FcR) binding assays can be conducted to ensure that the Fc-region or antibody lacks FcγR binding (hence likely lacking ADCC activity), but retains FcRn binding ability. The primary cells for mediating ADCC, NK cells, express FcγRIII only, whereas monocytes express FcγRI, FcγRII and FcγRIII FcR expression on hematopoietic cells is summarized in Table 3 on page 464 of Ravetch, J. V. and Kinet, J. P., Annu. Rev. Immunol. 9 (1991) 457-492. Non-limiting examples of in vitro assays to assess ADCC activity of a molecule of interest are described in U.S. Pat. No. 5,500,362 (see, e.g. Hellstrom, I. et al., Proc. Natl. Acad. Sci. USA 83 (1986) 7059-7063; and Hellstrom, I. et al., Proc. Natl. Acad. Sci. USA 82 (1985) 1499-1502); U.S. Pat. No. 5,821,337 (see Bruggemann, M. et al., J. Exp. Med. 166

(1987) 1351-1361). Alternatively, non-radioactive assays methods may be employed (see, for example, ACTI™ non-radioactive cytotoxicity assay for flow cytometry (CellTechnology, Inc. Mountain View, Calif.; and CytoTox 96® non-radioactive cytotoxicity assay (Promega, Madison, Wis.). Useful effector cells for such assays include peripheral blood mononuclear cells (PBMC) and Natural Killer (NK) cells. Alternatively, or additionally, ADCC activity of the molecule of interest may be assessed in vivo, e.g., in an animal model such as that disclosed in Clynes, R. et al., Proc. Natl. Acad. Sci. USA 95 (1998) 652-656. C1q binding assays may also be carried out to confirm that the Fc-region or antibody is unable to bind C1q and hence lacks CDC activity. See, e.g., C1q and C3c binding ELISA in WO 2006/029879 and WO 2005/100402. To assess complement activation, a CDC assay may be performed (see, for example, Gazzano-Santoro, H. et al., J. Immunol. Methods 202 (1996) 163-171; Cragg, M. S. et al., Blood 101 (2003) 1045-1052; and Cragg, M. S. and M. J. Glennie, Blood 103 (2004) 2738-2743). FcRn binding and in vivo clearance/half-life determinations can also be performed using methods known in the art (see, e.g., Petkova, S. B. et al., Int. Immunol. 18 (2006) 1759-1769).

Fc-regions or antibodies with reduced effector function include those with substitution of one or more of Fc-region residues 238, 265, 269, 270, 297, 327 and 329 (U.S. Pat. No. 6,737,056). Such Fc-region variants include Fc-regions with substitutions at two or more of amino acid positions 265, 269, 270, 297 and 327, including the so-called "DANA" Fc-region mutant with substitution of residues 265 and 297 to alanine (U.S. Pat. No. 7,332,581).

Certain Fc-region or antibody variants with improved or diminished binding to FcRs are described (see, e.g., U.S. Pat. No. 6,737,056; WO 2004/056312, and Shields, R. L. et al., J. Biol. Chem. 276 (2001) 6591-6604).

In certain embodiments, an Fc-region or antibody variant comprises an Fc-region with one or more amino acid substitutions which improve ADCC, e.g., substitutions at positions 298, 333, and/or 334 of the Fc-region (EU numbering of residues).

In some embodiments, alterations are made in the Fc-region that result in altered (i.e., either improved or diminished) C1q binding and/or Complement Dependent Cytotoxicity (CDC), e.g., as described in U.S. Pat. No. 6,194,551, WO 99/51642, and Idusogie, E. E. et al., J. Immunol. 164 (2000) 4178-4184.

Antibodies with increased half-lives and improved binding to the neonatal Fc receptor (FcRn), which is responsible for the transfer of maternal IgGs to the fetus (Guyer, R. L. et al., J. Immunol. 117 (1976) 587-593, and Kim, J. K. et al., J. Immunol. 24 (1994) 2429-2434), are described in US 2005/0014934. Those antibodies comprise an Fc-region with one or more substitutions therein which improve binding of the Fc-region to FcRn. Such Fc-region variants include those with substitutions at one or more of Fc-region residues: 238, 256, 265, 272, 286, 303, 305, 307, 311, 312, 317, 340, 356, 360, 362, 376, 378, 380, 382, 413, 424 or 434, e.g., substitution of Fc-region residue 434 (U.S. Pat. No. 7,371,826).

See also Duncan, A. R. and Winter, G., Nature 322 (1988) 738-740; U.S. Pat. Nos. 5,648,260; 5,624,821; and WO 94/29351 concerning other examples of Fc-region variants.

d) Cysteine Engineered Antibody Variants

In certain embodiments, it may be desirable to create cysteine engineered antibodies, e.g., "thioMAbs," in which one or more residues of an antibody are substituted with cysteine residues. In particular embodiments, the substituted residues occur at accessible sites of the antibody. By substituting those residues with cysteine, reactive thiol groups are thereby positioned at accessible sites of the antibody and may be used to conjugate the antibody to other moieties, such as drug moieties or linker-drug moieties, to create an immunoconjugate, as described further herein. In certain embodiments, any one or more of the following residues may be substituted with cysteine: V205 (Kabat numbering) of the light chain; A118 (EU numbering) of the heavy chain; and S400 (EU numbering) of the heavy chain Fc-region. Cysteine engineered antibodies may be generated as described, e.g., in U.S. Pat. No. 7,521,541.

e) Fc-Region and Antibody Derivatives

In certain embodiments, an Fc-region or antibody provided herein may be further modified to contain additional non-proteinaceous moieties that are known in the art and readily available. The moieties suitable for derivatization of the Fc-region or antibody include but are not limited to water soluble polymers. Non-limiting examples of water soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1,3-dioxolane, poly-1,3,6-trioxane, ethylene/maleic anhydride copolymer, polyaminoacids (either homopolymers or random copolymers), and dextran or poly(n-vinyl pyrrolidone)polyethylene glycol, propropylene glycol homopolymers, prolypropylene oxide/ethylene oxide co-polymers, polyoxyethylated polyols (e.g., glycerol), polyvinyl alcohol, and mixtures thereof. Polyethylene glycol propionaldehyde may have advantages in manufacturing due to its stability in water. The polymer may be of any molecular weight, and may be branched or non-branched. The number of polymers attached to the Fc-region or antibody may vary, and if more than one polymer is attached, they can be the same or different molecules. In general, the number and/or type of polymers used for derivatization can be determined based on considerations including, but not limited to, the particular properties or functions of the Fc-region or antibody to be improved, whether the Fc-region or antibody derivative will be used in a therapy under defined conditions, etc.

In another embodiment, conjugates of an Fc-region or antibody and one or more non-proteinaceous moiety that may be selectively heated by exposure to radiation are provided. In one embodiment, the non-proteinaceous moiety is a carbon nanotube (Kam, N. W. et al., Proc. Natl. Acad. Sci. USA 102 (2005) 11600-11605). The radiation may be of any wavelength, and includes, but is not limited to, wavelengths that do not harm ordinary cells, but which heat the non-proteinaceous moiety to a temperature at which cells proximal to the antibody-non-proteinaceous moiety are killed.

f) Heterodimerization

There exist several approaches for CH3-modifications to enforce the heterodimerization, which are well described e.g. in WO 96/27011, WO 98/050431, EP 1870459, WO 2007/110205, WO 2007/147901, WO 2009/089004, WO 2010/129304, WO 2011/90754, WO 2011/143545, WO 2012058768, WO 2013157954, WO 2013096291. Typically in all such approaches the first CH3 domain and the second CH3 domains are both engineered in a complementary manner so that each CH3 domain (or the heavy chain comprising it) cannot longer homodimerize with itself but is forced to heterodimerize with the complementary engineered other CH3 domain (so that the first and second CH3 domain heterodimerize and no homodimers between the two first or the two second CH3 domains are formed). These different approaches for improved heavy chain heterodimerization are contemplated as different alternatives in combination with the heavy-light chain modifications (VH and VL exchange/replacement in one binding arm and the introduction of substitutions of charged amino acids with opposite charges in the CH1/CL interface) in the multispecific antibodies according to the invention which reduce light chain mispairing an Bence-Jones type side products.

In one preferred embodiment of the invention (in case the multispecific antibody comprises CH3 domains in the heavy chains) the CH3 domains of said multispecific antibody according to the invention can be altered by the "knob-into-holes" technology which is described in detail with several examples in e.g. WO 96/027011, Ridgway, J. B., et al., Protein Eng. 9 (1996) 617-621; and Merchant, A. M., et al., Nat. Biotechnol. 16 (1998) 677-681; WO 98/050431. In this method the interaction surfaces of the two CH3 domains are altered to increase the heterodimerization of both heavy chains containing these two CH3 domains. Each of the two CH3 domains (of the two heavy chains) can be the "knob", while the other is the "hole". The introduction of a disulfide bridge further stabilizes the heterodimers (Merchant, A. M., et al., Nature Biotech. 16 (1998) 677-681; Atwell, S., et al., J. Mol. Biol. 270 (1997) 26-35) and increases the yield.

Thus in one embodiment of the invention said multispecific antibody (comprises a CH3 domain in each heavy chain and) is further characterized in that
the first CH3 domain of the first heavy chain of the antibody under a) and the second CH3 domain of the second heavy chain of the antibody under b) each meet at an interface which comprises an original interface between the antibody CH3 domains.
wherein said interface is altered to promote the formation of the multispecific antibody, wherein the alteration is characterized in that:
i) the CH3 domain of one heavy chain is altered,
so that within the original interface of the CH3 domain of one heavy chain that meets the original interface of the CH3 domain of the other heavy chain within the multispecific antibody,
an amino acid residue is replaced with an amino acid residue having a larger side chain volume, thereby generating a protuberance within the interface of the CH3 domain of one heavy chain which is positionable in a cavity within the interface of the CH3 domain of the other heavy chain
and
ii) the CH3 domain of the other heavy chain is altered,
so that within the original interface of the second CH3 domain that meets the original interface of the first CH3 domain within the multispecific antibody
an amino acid residue is replaced with an amino acid residue having a smaller side chain volume, thereby generating a cavity protuberance within the interface of the first CH3 domain is positionable.

Preferably said amino acid residue having a larger side chain volume is selected from the group consisting of arginine (R), phenylalanine (F), tyrosine (Y), tryptophan (W).

Preferably said amino acid residue having a smaller side chain volume is selected from the group consisting of alanine (A), serine (S), threonine (T), valine (V).

In one aspect of the invention both CH3 domains are further altered by the introduction of cysteine (C) as amino acid in the corresponding positions of each CH3 domain such that a disulfide bridge between both CH3 domains can be formed.

In one preferred embodiment, said multispecific antibody comprises an amino acid T366W mutation in the first CH3 domain of the "knob-chain" and amino acid T366S, L368A, Y407V mutations in the second CH3 domain of the "hole-chain". An additional interchain disulfide bridge between the CH3 domains can also be used (Merchant, A. M., et al., Nature Biotech. 16 (1998) 677-681) e.g. by introducing an amino acid Y349C mutation into the CH3 domain of the "hole chain" and an amino acid E356C mutation or an amino acid S354C mutation into the CH3 domain of the "knobs chain".

In one preferred embodiment, said multispecific antibody (which comprises a CH3 domain in each heavy chain) comprises amino acid S354C, T366W mutations in one of the two CH3 domains and amino acid Y349C, T366S, L368A, Y407V mutations in the other of the two CH3 domains (the additional amino acid S354C mutation in one CH3 domain and the additional amino acid Y349C mutation in the other CH3 domain forming an interchain disulfide bridge) (numbering according to Kabat).

Other techniques for CH3-modifications to enforcing the heterodimerization are contemplated as alternatives of the invention and described e.g. in WO 96/27011, WO 98/050431, EP 1870459, WO 2007/110205, WO 2007/147901, WO 2009/089004, WO 2010/129304, WO 2011/90754, WO 2011/143545, WO 2012/058768, WO 2013/157954, WO 2013/096291.

In one embodiment the heterodimerization approach described in EP 1 870 459A1, can be used alternatively. This approach is based on the by the introduction of substitutions/mutations of charged amino acids with the opposite charge at specific amino acid positions of the in the CH3/CH3 domain interface between both heavy chains. One preferred embodiment for said multispecific antibody are amino acid R409D; K370E mutations in the first CH3 domain of the (of the multispecific antibody) and amino acid D399K; E357K mutations in the seconds CH3 domain of the multispecific antibody (numbering according to Kabat).

In another embodiment said multispecific antibody comprises a amino acid T366W mutation in the CH3 domain of the "knobs chain" and amino acid T366S, L368A, Y407V mutations in the CH3 domain of the "hole chain" and additionally amino acid R409D; K370E mutations in the CH3 domain of the "knobs chain" and amino acid D399K; E357K mutations in the CH3 domain of the "hole chain".

In another embodiment said multispecific antibody comprises amino acid S354C, T366W mutations in one of the two CH3 domains and amino acid Y349C, T366S, L368A, Y407V mutations in the other of the two CH3 domains or said multispecific antibody comprises amino acid Y349C, T366W mutations in one of the two CH3 domains and amino acid S354C, T366S, L368A, Y407V mutations in the other of the two CH3 domains and additionally amino acid R409D; K370E mutations in the CH3 domain of the "knobs chain" and amino acid D399K; E357K mutations in the CH3 domain of the "hole chain".

In one embodiment the heterodimerization approach described in WO2013/157953 can be used alternatively. In one embodiment a first CH3 domain comprises amino acid T366K mutation and a second CH3 domain polypeptide comprises amino acid L351D mutation. In a further embodiment the first CH3 domain comprises further amino acid L351K mutation. In a further embodiment the second CH3 domain comprises further amino acid mutation selected from Y349E, Y349D and L368E (preferably L368E).

In one embodiment the heterodimerization approach described in WO2012/058768 can be used alternatively. In one embodiment a first CH3 domain comprises amino acid L351Y, Y407A mutations and a second CH3 domain comprises amino acid T366A, K409F mutations. In a further embodiment the second CH3 domain comprises a further amino acid mutation at position T411, D399, S400, F405, N390, or K392 e.g. selected from a) T411 N, T411R, T411Q, T411 K, T411D, T411E or T411W, b) D399R, D399W, D399Y or D399K, c S400E, S400D, S400R, or S400K F405I, F405M, F405T, F405S, F405V or F405W N390R, N390K or N390D K392V, K392M, K392R, K392L, K392F or K392E. In a further embodiment a first CH3 domain comprises amino acid L351Y, Y407A mutations and a second CH3 domain comprises amino acid T366V, K409F mutations. In a further embodiment a first CH3 domain comprises amino acid Y407A mutations and a second CH3 domain comprises amino acid T366A, K409F mutations. In a further embodiment the second CH3 domain comprises a further amino acid K392E, T411E, D399R and S400R mutations.

In one embodiment the heterodimerization approach described in WO2011/143545 can be used alternatively e.g. with the amino acid modification at a position selected from the group consisting of 368 and 409.

In one embodiment the heterodimerization approach described in WO2011/090762 which also uses the knobs-into-holes technology described above can be used alternatively. In one embodiment a first CH3 domain comprises amino acid T366W mutations and a second CH3 domain comprises amino acid Y407A mutations. In one embodiment a first CH3 domain comprises amino acid T366Y mutations and a second CH3 domain comprises amino acid Y407T mutations.

In one embodiment the multispecific antibody is of IgG2 isotype and the heterodimerization approach described in WO2010/129304 can be used alternatively.

In one embodiment the heterodimerization approach described in WO2009/089004 can be used alternatively. In one embodiment a first CH3 domain comprises amino acid substitution of K392 or N392 with a negative-charged amino acid (e.g. glutamic acid (E), or aspartic acid (D), preferably K392D or N392D) and a second CH3 domain comprises amino acid substitution of D399, E356, D356, or E357 with a positive-charged amino acid (e.g. Lysine (K) or arginine (R), preferably D399K, E356K, D356K, or E357K and more preferably D399K and E356K. In a further embodiment the first CH3 domain further comprises amino acid substitution of K409 or R409 with a negative-charged amino acid (e.g. glutamic acid (E), or aspartic acid (D), preferably K409D or R409D). In a further embodiment the first CH3 domain further or alternatively comprises amino acid substitution of K439 and/or K370 with a negative-charged amino acid (e.g. glutamic acid (E), or aspartic acid (D)).

In one embodiment the heterodimerization approach described in WO2007/147901 can be used alternatively. In one embodiment a first CH3 domain comprises amino acid K253E, D282K, and K322D mutations and a second CH3 domain comprises amino acid D239K, E240K, and K292D mutations.

In one embodiment the heterodimerization approach described in WO2007/110205 can be used alternatively.

Recombinant Methods and Formulations

Fc-regions and antibodies may be produced using recombinant methods and formulations, e.g., as described in U.S. Pat. No. 4,816,567. In one embodiment, isolated nucleic acid(s) encoding an Fc-region or antibody as described herein is(are) provided. Such nucleic acid may encode an amino acid sequence comprising the VL and/or an amino acid sequence comprising the VH of the antibody (e.g., the light and/or heavy chains of the antibody). In a further embodiment, one or more vectors (e.g., expression vectors) comprising such nucleic acid are provided. In a further embodiment, a host cell comprising such nucleic acid is provided. In one such embodiment, a host cell comprises (e.g., has been transformed with): (1) a vector comprising a nucleic acid that encodes an amino acid sequence comprising the VL of the antibody and an amino acid sequence comprising the VH of the antibody, or (2) a first vector comprising a nucleic acid that encodes an amino acid sequence comprising the VL of the antibody and a second vector comprising a nucleic acid that encodes an amino acid sequence comprising the VH of the antibody. In one embodiment, the host cell is eukaryotic, e.g. a Chinese Hamster Ovary (CHO) cell or lymphoid cell (e.g., Y0, NS0, Sp20 cell). In one embodiment, a method of making an antibody as reported herein is provided, wherein the method comprises culturing a host cell comprising a nucleic acid encoding the antibody, as provided above, under conditions suitable for expression of the antibody, and optionally recovering the antibody from the host cell (or host cell culture medium).

For recombinant production of an variant Fc-region, nucleic acid encoding the variant Fc-region, e.g., as described above, is isolated and inserted into one or more vectors for further cloning and/or expression in a host cell. Such nucleic acid may be readily isolated and sequenced using conventional procedures (e.g., by using oligonucleotide probes that are capable of binding specifically to genes encoding the variant Fc-region polypeptides or heavy and light chains of the antibody).

Suitable host cells for cloning or expression of antibody-encoding vectors include prokaryotic or eukaryotic cells described herein. For example, antibodies may be produced in bacteria, in particular when glycosylation and Fc effector function are not needed. For expression of antibody fragments and polypeptides in bacteria, see, e.g., U.S. Pat. Nos. 5,648,237, 5,789,199, and 5,840,523 (see also Charlton, K. A., In: Methods in Molecular Biology, Vol. 248, Lo, B. K. C. (ed.), Humana Press, Totowa, N.J. (2003), pp. 245-254, describing expression of antibody fragments in *E. coli*). After expression, the antibody may be isolated from the bacterial cell paste in a soluble fraction and can be further purified.

In addition to prokaryotes, eukaryotic microbes such as filamentous fungi or yeast are suitable cloning or expression hosts for antibody-encoding vectors, including fungi and yeast strains whose glycosylation pathways have been "humanized", resulting in the production of an antibody with a partially or fully human glycosylation pattern. See Gerngross, T. U., Nat. Biotech. 22 (2004) 1409-1414; and Li, H. et al., Nat. Biotech. 24 (2006) 210-215.

Suitable host cells for the expression of glycosylated Fc-region or antibody are also derived from multicellular organisms (invertebrates and vertebrates). Examples of invertebrate cells include plant and insect cells. Numerous baculoviral strains have been identified which may be used in conjunction with insect cells, particularly for transfection of *Spodoptera frugiperda* cells.

Plant cell cultures can also be utilized as hosts. See, e.g., U.S. Pat. Nos. 5,959,177, 6,040,498, 6,420,548, 7,125,978, and 6,417,429 (describing PLANTIBODIES™ technology for producing antibodies in transgenic plants).

Vertebrate cells may also be used as hosts. For example, mammalian cell lines that are adapted to grow in suspension may be useful. Other examples of useful mammalian host cell lines are monkey kidney CV1 line transformed by SV40 (COS-7); human embryonic kidney line (HEK293 or 293 cells as described, e.g., in Graham, F. L., et al., J. Gen Virol. 36 (1977) 59-74); baby hamster kidney cells (BHK); mouse sertoli cells (TM4 cells as described, e.g., in Mather, J. P., Biol. Reprod. 23 (1980) 243-252); monkey kidney cells (CV1); African green monkey kidney cells (VERO-76); human cervical carcinoma cells (HELA); canine kidney cells (MDCK); buffalo rat liver cells (BRL 3A); human lung cells (W138); human liver cells (Hep G2); mouse mammary tumor (MMT 060562); TRI cells, as described, e.g., in Mather, J. P., et al., Annals N.Y. Acad. Sci. 383 (1982) 44-68; MRC 5 cells; and FS4 cells. Other useful mammalian host cell lines include Chinese hamster ovary (CHO) cells, including DHFR$^-$ CHO cells (Urlaub, G., et al., Proc. Natl. Acad. Sci. USA 77 (1980) 4216-4220); and myeloma cell lines such as Y0, NS0 and Sp2/0. For a review of certain mammalian host cell lines suitable for antibody production, see, e.g., Yazaki, P. and Wu, A. M., Methods in Molecular Biology, Vol. 248, Lo, B. K. C. (ed.), Humana Press, Totowa, N.J. (2004), pp. 255-268.

Assays

Antibodies provided herein may be identified, screened for, or characterized for their physical/chemical properties and/or biological activities by various assays known in the art.

In one aspect, an antibody as reported herein is tested for its antigen binding activity, e.g., by known methods such as ELISA, Western Blot, etc.

Immunoconjugates

The invention also provides immunoconjugates comprising an antibody as reported herein conjugated to one or more cytotoxic agents, such as chemotherapeutic agents or drugs, growth inhibitory agents, toxins (e.g., protein toxins, enzymatically active toxins of bacterial, fungal, plant, or animal origin, or fragments thereof), or radioactive isotopes.

In one embodiment, an immunoconjugate is an antibody-drug conjugate (ADC) in which an antibody is conjugated to one or more drugs, including but not limited to a maytansinoid (see U.S. Pat. Nos. 5,208,020, 5,416,064 and EP 0 425 235 B1); an auristatin such as monomethyl auristatin drug moieties DE and DF (MMAE and MMAF) (see U.S. Pat. Nos. 5,635,483, 5,780,588, and 7,498,298); a dolastatin; a calicheamicin or derivative thereof (see U.S. Pat. Nos. 5,712,374, 5,714,586, 5,739,116, 5,767,285, 5,770,701, 5,770,710, 5,773,001, and 5,877,296; Hinman, L. M. et al., Cancer Res. 53 (1993) 3336-3342; and Lode, H. N. et al., Cancer Res. 58 (1998) 2925-2928); an anthracycline such as daunomycin or doxorubicin (see Kratz, F. et al., Curr. Med. Chem. 13 (2006) 477-523; Jeffrey, S. C. et al., Bioorg. Med. Chem. Lett. 16 (2006) 358-362; Torgov, M. Y. et al., Bioconjug. Chem. 16 (2005) 717-721; Nagy, A. et al., Proc. Natl. Acad. Sci. USA 97 (2000) 829-834; Dubowchik, G. M. et al., Bioorg.& Med. Chem. Letters 12 (2002) 1529-1532; King, H. D. et al., J. Med. Chem. 45 (2002) 4336-4343; and U.S. Pat. No. 6,630,579); methotrexate; vindesine; a taxane such as docetaxel, paclitaxel, larotaxel, tesetaxel, and ortataxel; a trichothecene; and CC1065.

In another embodiment, an immunoconjugate comprises an antibody as described herein conjugated to an enzymatically active toxin or fragment thereof, including but not limited to diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *Momordica charantia* inhibitor, curcin, crotin, *Sapaonaria officinalis* inhibitor, gelonin, mitogellin, restrictocin, phenomycin, enomycin, and the tricothecenes.

In another embodiment, an immunoconjugate comprises an antibody as described herein conjugated to a radioactive atom to form a radioconjugate. A variety of radioactive isotopes are available for the production of radioconjugates. Examples include At$^{211}$, I$^{131}$, I$^{125}$ Y$^{90}$, Re$^{186}$, Re$^{188}$, Sm$^{153}$, Bi$^{212}$, P$^{32}$, Pb$^{212}$ and radioactive isotopes of Lu. When the radioconjugate is used for detection, it may comprise a radioactive atom for scintigraphic studies, for example TC$^{99m}$ or I$^{123}$, or a spin label for nuclear magnetic resonance (NMR) imaging (also known as magnetic resonance imaging, MRI), such as iodine-123, iodine-131, indium-111, fluorine-19, carbon-13, nitrogen-15, oxygen-17, gadolinium, manganese or iron.

Conjugates of an antibody and cytotoxic agent may be made using a variety of bifunctional protein coupling agents such as N-succinimidyl-3-(2-pyridyldithio) propionate (SPDP), succinimidyl-4-(N-maleimidomethyl) cyclohexane-1-carboxylate (SMCC), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis (p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). For example, a ricin immunotoxin can be prepared as described in Vitetta, E. S. et al., Science 238 (1987) 1098-1104. Carbon-14-labeled 1-isothiocyanatobenzyl-3-methyldiethylene triamine pentaacetic acid (MX-DTPA) is an exemplary chelating agent for conjugation of radionucleotide to the antibody. See WO 94/11026. The linker may be a "cleavable linker" facilitating release of a cytotoxic drug in the cell. For example, an acid-labile linker, peptidase-sensitive linker, photolabile linker, dimethyl linker or disulfide-containing linker (Chari, R. V. et al., Cancer Res. 52 (1992) 127-131; U.S. Pat. No. 5,208,020) may be used.

The immuno-conjugates or ADCs herein expressly contemplate, but are not limited to such conjugates prepared with cross-linker reagents including, but not limited to, BMPS, EMCS, GMBS, HBVS, LC-SMCC, MBS, MPBH, SBAP, SIA, STAB, SMCC, SMPB, SMPH, sulfo-EMCS, sulfo-GMBS, sulfo-KMUS, sulfo-MBS, sulfo-STAB, sulfo-SMCC, and sulfo-SMPB, and SVSB (succinimidyl-(4-vinylsulfone) benzoate) which are commercially available (e.g., from Pierce Biotechnology, Inc., Rockford, Ill., U.S.A).

Methods and Formulations for Diagnostics and Detection

In certain embodiments, any of the antibodies provided herein is useful for detecting the presence of its cognate antigen(s) in a biological sample. The term "detecting" as used herein encompasses quantitative or qualitative detection. In certain embodiments, a biological sample comprises a cell or tissue.

In one embodiment, an antibody as reported herein for use in a method of diagnosis or detection is provided.

In certain embodiments, labeled antibodies as reported herein are provided. Labels include, but are not limited to, labels or moieties that are detected directly (such as fluorescent, chromophoric, electron-dense, chemiluminescent, and radioactive labels), as well as moieties, such as enzymes or ligands, that are detected indirectly, e.g., through an enzymatic reaction or molecular interaction. Exemplary labels include, but are not limited to, the radioisotopes $^{32}$P, $^{14}$C, $^{125}$I, $^{3}$H, and $^{131}$I, fluorophores such as rare earth chelates or fluorescein and its derivatives, rhodamine and its derivatives, dansyl, umbelliferone, luceriferases, e.g., firefly luciferase and bacterial luciferase (U.S. Pat. No. 4,737,456), luciferin, 2,3-dihydrophthalazinediones, horseradish peroxidase (HRP), alkaline phosphatase, β-galactosidase, glucoamylase, lysozyme, saccharide oxidases, e.g., glucose oxidase, galactose oxidase, and glucose-6-phosphate dehydrogenase, heterocyclic oxidases such as uricase and xanthine oxidase, coupled with an enzyme that employs hydrogen peroxide to oxidize a dye precursor such as HRP, lactoperoxidase, or microperoxidase, biotin/avidin, spin labels, bacteriophage labels, stable free radicals, and the like.

Pharmaceutical Formulations

Pharmaceutical formulations of an antibody as described herein are prepared by mixing such antibody having the desired degree of purity with one or more optional pharmaceutically acceptable carriers (Remington's Pharmaceutical Sciences, 16th edition, Osol, A. (ed.) (1980)), in the form of lyophilized formulations or aqueous solutions. Pharmaceutically acceptable carriers are generally nontoxic to recipients at the dosages and concentrations employed, and include, but are not limited to: buffers such as phosphate, citrate, and other organic acids; antioxidants including ascorbic acid and methionine; preservatives (such as octadecyl dimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as poly(vinylpyrrolidone); amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as polyethylene glycol (PEG). Exemplary pharmaceutically acceptable carriers herein further include interstitial drug dispersion agents such as soluble neutral-active hyaluronidase glycoproteins (sHASEGP), for example, human soluble PH-20 hyaluronidase glycoproteins, such as rhuPH20 (HYLENEX®, Baxter International, Inc.). Certain exemplary sHASEGPs and methods of use, including rhuPH20, are described in US 2005/0260186 and US 2006/0104968. In one aspect, a sHASEGP is combined with one or more additional glycosaminoglycanases such as chondroitinases.

Exemplary lyophilized antibody formulations are described in U.S. Pat. No. 6,267,958. Aqueous antibody formulations include those described in U.S. Pat. No. 6,171,586 and WO 2006/044908, the latter formulations including a histidine-acetate buffer.

The formulation herein may also contain more than one active ingredients as necessary for the particular indication being treated, preferably those with complementary activities that do not adversely affect each other. Such active ingredients are suitably present in combination in amounts that are effective for the purpose intended.

Active ingredients may be entrapped in microcapsules prepared, for example, by coacervation techniques or by interfacial polymerization, for example, hydroxymethylcellulose or gelatin-microcapsules and poly-(methyl methacrylate) microcapsules, respectively, in colloidal drug delivery systems (for example, liposomes, albumin microspheres, microemulsions, nano-particles and nanocapsules) or in macroemulsions. Such techniques are disclosed in Remington's Pharmaceutical Sciences, 16th edition, Osol, A. (ed.) (1980).

Sustained-release preparations may be prepared. Suitable examples of sustained-release preparations include semipermeable matrices of solid hydrophobic polymers containing the antibody, which matrices are in the form of shaped articles, e.g. films, or microcapsules.

The formulations to be used for in vivo administration are generally sterile. Sterility may be readily accomplished, e.g., by filtration through sterile filtration membranes.

Therapeutic Methods and Formulations

Any of the antibodies provided herein may be used in therapeutic methods.

In one aspect, an antibody as reported herein for use as a medicament is provided.

In certain embodiments, an antibody for use in a method of treatment is provided. In one such embodiment, the method further comprises administering to the individual an effective amount of at least one additional therapeutic agent, e.g., as described below. An "individual" according to any of the above embodiments is in one preferred embodiment a human.

In a further aspect, the invention provides for the use of an antibody in the manufacture or preparation of a medicament. An "individual" according to any of the above embodiments may be a human.

In a further aspect, the invention provides pharmaceutical formulations comprising any of the antibodies provided herein, e.g., for use in any of the above therapeutic methods. In one embodiment, a pharmaceutical formulation comprises any of the antibodies provided herein and a pharmaceutically acceptable carrier. In another embodiment, a pharmaceutical formulation comprises any of the antibodies provided herein and at least one additional therapeutic agent, e.g., as described below.

Antibodies as reported herein can be used either alone or in combination with other agents in a therapy. For instance, an antibody as reported herein may be co-administered with at least one additional therapeutic agent.

An antibody as reported herein (and any additional therapeutic agent) can be administered by any suitable means, including parenteral, intrapulmonary, and intranasal, and, if desired for local treatment, intralesional administration. Parenteral infusions include intramuscular, intravenous, intraarterial, intraperitoneal, or subcutaneous administration. Dosing can be by any suitable route, e.g. by injections, such as intravenous or subcutaneous injections, depending in part on whether the administration is brief or chronic. Various dosing schedules including but not limited to single or multiple administrations over various time-points, bolus administration, and pulse infusion are contemplated herein.

Antibodies as reported herein would be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The antibody need not be, but is optionally formulated with one or more agents currently used to prevent or treat the disorder in question. The effective amount of such other agents depends on the amount of antibody present in the formulation, the type of disorder or treatment, and other factors discussed above. These are generally used in the same dosages and with administration routes as described herein, or about from 1 to 99% of the dosages described herein, or in any dosage and by any route that is empirically/clinically determined to be appropriate.

For the prevention or treatment of disease, the appropriate dosage of an antibody as reported herein (when used alone or in combination with one or more other additional therapeutic agents) will depend on the type of disease to be treated, the type of antibody, the severity and course of the disease, whether the antibody is administered for preventive or therapeutic purposes, previous therapy, the patient's clinical history and response to the antibody, and the discretion of the attending physician. The antibody is suitably administered to the patient at one time or over a series of treatments. Depending on the type and severity of the disease, about 1 µg/kg to 15 mg/kg (e.g. 0.5 mg/kg-10 mg/kg) of antibody can be an initial candidate dosage for administration to the patient, whether, for example, by one or more separate administrations, or by continuous infusion. One typical daily dosage might range from about 1 µg/kg to 100 mg/kg or more, depending on the factors mentioned above. For repeated administrations over several days or longer, depending on the condition, the treatment would generally be sustained until a desired suppression of disease symptoms occurs. One exemplary dosage of the antibody would be in the range from about 0.05 mg/kg to about 10 mg/kg. Thus, one or more doses of about 0.5 mg/kg, 2.0 mg/kg, 4.0 mg/kg or 10 mg/kg (or any combination thereof) may be administered to the patient. Such doses may be administered intermittently, e.g. every week or every three weeks (e.g. such that the patient receives from about two to about twenty, or e.g. about six doses of the antibody). An initial higher loading dose, followed by one or more lower doses may be administered. The progress of this therapy is easily monitored by conventional techniques and assays.

It is understood that any of the above formulations or therapeutic methods may be carried out using an immunoconjugate as reported herein in place of or in addition to an antibody as reported herein.

Articles of Manufacture

In another aspect as reported herein, an article of manufacture containing materials useful for the treatment, prevention and/or diagnosis of the disorders described above is provided. The article of manufacture comprises a container and a label or package insert on or associated with the container. Suitable containers include, for example, bottles, vials, syringes, IV solution bags, etc. The containers may be formed from a variety of materials such as glass or plastic. The container holds a formulation which is by itself or combined with another formulation effective for treating, preventing and/or diagnosing the condition and may have a sterile access port (for example the container may be an intravenous solution bag or a vial having a stopper pierceable by a hypodermic injection needle). At least one active agent in the formulation is an antibody as reported herein. The label or package insert indicates that the formulation is used for treating the condition of choice. Moreover, the article of manufacture may comprise (a) a first container with a formulation contained therein, wherein the formulation comprises an antibody as reported herein; and (b) a second container with a formulation contained therein, wherein the formulation comprises a further cytotoxic or otherwise therapeutic agent. The article of manufacture in this embodiment as reported herein may further comprise a package insert indicating that the formulations can be used to treat a particular condition. Alternatively, or additionally, the article of manufacture may further comprise a second (or third) container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

It is understood that any of the above articles of manufacture may include an immunoconjugate as reported herein in place of or in addition to an antibody as reported herein.

III. Specific Embodiments

1. An IgG class Fc-region comprising a first variant Fc-region polypeptide and a second variant Fc-region polypeptide,
   wherein
   a) the first variant Fc-region polypeptide is derived from a first parent IgG class Fc-region polypeptide and the second variant Fc-region polypeptide is derived from a second parent IgG class Fc-region polypeptide, whereby the first parent IgG class Fc-region polypeptide is identical to or different from the second parent IgG class Fc-region polypeptide, and
   b) the first variant Fc-region polypeptide differs from the second variant Fc-region polypeptide in one or more amino acid residues other than those amino acid residues in which the first parent IgG class Fc-region polypeptide differs from the second parent IgG class Fc-region polypeptide, and
   c) the IgG class Fc-region comprising the first variant Fc-region polypeptide and the second variant Fc-region polypeptide has an affinity to a human Fc-receptor that is different than that of an IgG class Fc-region comprising the first parent IgG class Fc-region polypeptide of a) and the second parent IgG class Fc-region polypeptide of a).

2. The IgG class Fc-region according to embodiment 1, wherein the human Fc-receptor is the human neonatal Fc receptor (FcRn) or the human FcgammaIII receptor (FcγRIII).

3. The IgG class Fc-region according to any one of embodiments 1 to 2, wherein the human Fc-receptor is the human neonatal Fc-receptor.

4. The IgG class Fc-region according to any one of embodiments 1 to 3, wherein the affinity of the IgG class Fc-region comprising the first variant Fc-region polypeptide and the second variant Fc-region polypeptide to a human Fc-receptor is increased or reduced by 10% or more determined by surface plasmon resonance (SPR) compared to that of an IgG class Fc-region comprising the first parent IgG class Fc-region polypeptide of a) and the second parent IgG class Fc-region polypeptide of a).

5. The IgG class Fc-region according to any one of embodiments 1 to 4, wherein at least some of those amino acid residues in which the first parent IgG class Fc-region polypeptide differs from the second parent IgG class Fc-region polypeptide promote the formation of a heterodimeric IgG class Fc-region.

6. The IgG class Fc-region according to any one of embodiments 1 to 5, wherein
   i) the first parent IgG class Fc-region polypeptide is selected from the group comprising
      human IgG1 Fc-region polypeptide,
      human IgG2 Fc-region polypeptide,
      human IgG3 Fc-region polypeptide,
      human IgG4 Fc-region polypeptide, human IgG1 Fc-region polypeptide with the mutations L234A, L235A,
human IgG1 Fc-region polypeptide with the mutations Y349C, T366S, L368A, Y407V,
human IgG1 Fc-region polypeptide with the mutations S354C, T366S, L368A, Y407V,
human IgG1 Fc-region polypeptide with the mutations L234A, L235A, Y349C, T366S, L368A, Y407V,
human IgG1 Fc-region polypeptide with the mutations L234A, L235A, S354C, T366S, L368A, Y407V,
human IgG1 Fc-region polypeptide with the mutations P329G,
human IgG1 Fc-region polypeptide with the mutations L234A, L235A, P329G,
human IgG1 Fc-region polypeptide with the mutations P329G, Y349C, T366S, L368A, Y407V,
human IgG1 Fc-region polypeptide with the mutations P329G, S354C, T366S, L368A, Y407V,
human IgG1 Fc-region polypeptide with the mutations L234A, L235A, P329G, Y349C, T366S, L368A, Y407V,
human IgG1 Fc-region polypeptide with the mutations L234A, L235A, P329G, S354C, T366S, L368A, Y407V,
human IgG4 Fc-region polypeptide with the mutations S228P, L235E,
human IgG4 Fc-region polypeptide with the mutations S228P, L235E, P329G,
human IgG4 Fc-region polypeptide with the mutations Y349C, T366S, L368A, Y407V,
human IgG4 Fc-region polypeptide with the mutations S354C, T366S, L368A, Y407V,
human IgG4 Fc-region polypeptide with the mutations S228P, L235E, Y349C, T366S, L368A, Y407V,
human IgG4 Fc-region polypeptide with the mutations S228P, L235E, S354C, T366S, L368A, Y407V,
human IgG4 Fc-region polypeptide with the mutations P329G,
human IgG4 Fc-region polypeptide with the mutations P329G, Y349C, T366S, L368A, Y407V,
human IgG4 Fc-region polypeptide with the mutations P329G, S354C, T366S, L368A, Y407V,
human IgG4 Fc-region polypeptide with the mutations S228P, L235E, P329G, Y349C, T366S, L368A, Y407V,
human IgG4 Fc-region polypeptide with the mutations S228P, L235E, P329G, S354C, T366S, L368A, Y407V,
human IgG1, IgG2 or IgG4 with the mutation K392D, and
human IgG3 with the mutation N392D,
and
ii) the second parent IgG class Fc-region polypeptide is selected from the group comprising
human IgG1 Fc-region polypeptide,
human IgG2 Fc-region polypeptide,
human IgG3 Fc-region polypeptide,
human IgG4 Fc-region polypeptide,
human IgG1 Fc-region polypeptide with the mutations L234A, L235A,
human IgG1 Fc-region polypeptide with the mutations S354C, T366W,
human IgG1 Fc-region polypeptide with the mutations Y349C, T366W,
human IgG1 Fc-region polypeptide with the mutations L234A, L235A, S354C, T366W,
human IgG1 Fc-region polypeptide with the mutations L234A, L235A, Y349C, T366W,
human IgG1 Fc-region polypeptide with the mutations P329G,
human IgG1 Fc-region polypeptide with the mutations L234A, L235A, P329G,
human IgG1 Fc-region polypeptide with the mutations P329G, S354C, T366W,
human IgG1 Fc-region polypeptide with the mutations P329G, Y349C, T366W,
human IgG1 Fc-region polypeptide with the mutations L234A, L235A, P329G, S354C, T366W,
human IgG1 Fc-region polypeptide with the mutations L234A, L235A, P329G, Y349C, T366W,
human IgG4 Fc-region polypeptide with the mutations S228P, L235E,
human IgG4 Fc-region polypeptide with the mutations S228P, L235E, P329G,
human IgG4 Fc-region polypeptide with the mutations S354C, T366W,
human IgG4 Fc-region polypeptide with the mutations Y349C, T366W,
human IgG4 Fc-region polypeptide with the mutations S228P, L235E, S354C, T366W,
human IgG4 Fc-region polypeptide with the mutations S228P, L235E, Y349C, T366W,
human IgG4 Fc-region polypeptide with the mutations P329G,
human IgG4 Fc-region polypeptide with the mutations P329G, S354C, T366W,
human IgG4 Fc-region polypeptide with the mutations P329G, Y349C, T366W,
human IgG4 Fc-region polypeptide with the mutations S228P, L235E, P329G, S354C, T366W,
human IgG4 Fc-region polypeptide with the mutations S228P, L235E, P329G, Y349C, T366W,
human IgG1 with the mutations D399K, D356K, and/or E357K, and
human IgG2, IgG3 or IgG4 with the mutations D399K, E356K, and/or E357K.

7. The IgG class Fc-region according to any one of embodiments 1 to 6, wherein
i) the first parent IgG class Fc-region polypeptide is a human IgG1 Fc-region polypeptide and the second parent IgG class Fc-region polypeptide is a human IgG1 Fc-region polypeptide, or
ii) the first parent IgG class Fc-region polypeptide is a human IgG1 Fc-region polypeptide with the mutations L234A, L235A and the second parent IgG class Fc-region polypeptide is a human IgG1 Fc-region polypeptide with the mutations L234A, L235A, or
iii) the first parent IgG class Fc-region polypeptide is a human IgG1 Fc-region polypeptide with the mutations L234A, L235A, P329G and the second parent IgG class Fc-region polypeptide is a human IgG1 Fc-region polypeptide with the mutations L234A, L235A, P329G, or
iv) the first parent IgG class Fc-region polypeptide is a human IgG1 Fc-region polypeptide with the mutations L234A, L235A, S354C, T366W and the second parent IgG class Fc-region polypeptide is a human IgG1 Fc-region polypeptide with the mutations L234A, L235A, Y349C, T366S, L368A, Y407V, or
v) the first parent IgG class Fc-region polypeptide is a human IgG1 Fc-region polypeptide with the mutations L234A, L235A, P329G, S354C, T366W and the second parent IgG class Fc-region polypeptide is a human IgG1 Fc-region polypeptide with the mutations L234A, L235A, P329G, Y349C, T366S, L368A, Y407V, or
vi) the first parent IgG class Fc-region polypeptide is a human IgG4 Fc-region polypeptide and the second parent IgG class Fc-region polypeptide is a human IgG4 Fc-region polypeptide, or
vii) the first parent IgG class Fc-region polypeptide is a human IgG4 Fc-region polypeptide with the mutations S228P, L235E and the second parent IgG class Fc-region polypeptide is a human IgG4 Fc-region polypeptide with the mutations S228P, L235E, or
viii) the first parent IgG class Fc-region polypeptide is a human IgG4 Fc-region polypeptide with the mutations S228P, L235E, P329G and the second parent IgG class Fc-region polypeptide is a human IgG4 Fc-region polypeptide with the mutations S228P, L235E, P329G, or
ix) the first parent IgG class Fc-region polypeptide is a human IgG4 Fc-region polypeptide with the mutations S228P, L235E, S354C, T366W and the second parent IgG class Fc-region polypeptide is a human IgG4 Fc-region polypeptide with the mutations S228P, L235E, Y349C, T366S, L368A, Y407V, or
x) the first parent IgG class Fc-region polypeptide is a human IgG4 Fc-region polypeptide with the mutations S228P, L235E, P329G, S354C, T366W and the second parent IgG class Fc-region polypeptide is a human IgG4 Fc-region polypeptide with the mutations S228P, L235E, P329G, Y349C, T366S, L368A, Y407V.

8. The IgG class Fc-region according to any one of embodiments 1 to 7, wherein the first Fc-region polypeptide or the second Fc-region polypeptide or both Fc-region polypeptides comprise one of the following mutations or combination of mutations:
T307H, or
Q311H, or
E430 H, or
N434H, or
T307H and Q311H, or
T307H and E430H, or
T307H and N434A, or
T307H and N434H, or
T307Q and Q311H, or
T307Q and E430H, or
T307Q and N434H, or
T307H and Q311H and E430H and N434A, or
T307H and Q311H and E430H and N434H, or
T307H and Q311H and E430H and N434Y, or
T307Q and Q311H and E430H and N434A, or
T307Q and Q311H and E430H and N434H, or
T307Q and Q311H and E430H and N434Y, or
T307Q and V308P and N434Y and Y436H, or
T307H and M252Y and S254T and T256E, or
T307Q and M252Y and S254T and T256E, or
Q311H and M252Y and S254T and T256E, or
E430 H and M252Y and S254T and T256E, or
N434H and M252Y and S254T and T256E, or
T307H and Q311H and M252Y and S254T and T256E, or
T307H and E430H and M252Y and S254T and T256E, or
T307H and N434A and M252Y and S254T and T256E, or
T307H and N434H and M252Y and S254T and T256E, or
T307Q and Q311H and M252Y and S254T and T256E, or
T307Q and E430H and M252Y and S254T and T256E, or
T307Q and N434H and M252Y and S254T and T256E, or
T307H and Q311H and E430H and N434A and M252Y and S254T and T256E, or
T307H and Q311H and E430H and N434H and M252Y and S254T and T256E, or
T307H and Q311H and E430H and N434Y and M252Y and S254T and T256E, or
T307Q and Q311H and E430H and N434A and M252Y and S254T and T256E, or
T307Q and Q311H and E430H and N434H and M252Y and S254T and T256E, or
T307Q and Q311H and E430H and N434Y and M252Y and S254T and T256E, or
T307Q and V308P and N434Y and Y436H and M252Y and S254T and T256E.

9. The IgG class Fc-region according to any one of embodiments 1 to 8, wherein the first Fc-region polypeptide comprise independently of the second Fc-region polypeptide one of the following mutations or combination of mutations:
T307H, or
Q311H, or
E430 H, or
N434H, or
T307H and Q311H, or
T307H and E430H, or
T307H and N434A, or
T307H and N434H, or
T307Q and Q311H, or
T307Q and E430H, or
T307Q and N434H, or
M252Y and S254T and T256E, or
I253A and H310A and H435A, or
H310A and H433A and Y436A, or
T307H and Q311H and E430H and N434A, or
T307H and Q311H and E430H and N434H, or
T307H and Q311H and E430H and N434Y, or
T307Q and Q311H and E430H and N434A, or
T307Q and Q311H and E430H and N434H, or
T307Q and Q311H and E430H and N434Y, or
T307Q and V308P and N434Y and Y436H, or
T307H and M252Y and S254T and T256E, or
Q311H and M252Y and S254T and T256E, or
E430 H and M252Y and S254T and T256E, or
N434H and M252Y and S254T and T256E, or
T307H and Q311H and M252Y and S254T and T256E, or
T307H and E430H and M252Y and S254T and T256E, or
T307H and N434A and M252Y and S254T and T256E, or
T307H and N434H and M252Y and S254T and T256E, or
T307Q and Q311H and M252Y and S254T and T256E, or
T307Q and E430H and M252Y and S254T and T256E, or
T307Q and N434H and M252Y and S254T and T256E, or
T307H and Q311H and E430H and N434A and M252Y and S254T and T256E, or
T307H and Q311H and E430H and N434H and M252Y and S254T and T256E, or
T307H and Q311H and E430H and N434Y and M252Y and S254T and T256E, or
T307Q and V308P and N434Y and Y436H and M252Y and S254T and T256E, or
T307Q and V308P and N434Y and Y436H and M252Y and S254T and T256E,
and
the second Fc-region polypeptide comprise independently of the first Fc-region polypeptide one of the following mutations or combination of mutations
T307H, or
T307Q, or
Q311H, or
E430 H, or
N434H, or
T307H and Q311H, or T307H and E430H, or
T307H and N434A, or
T307H and N434H, or
T307Q and Q311H, or
T307Q and E430H, or
T307Q and N434H, or
T307H and Q311H and E430H and N434A, or
T307H and Q311H and E430H and N434H, or
T307H and Q311H and E430H and N434Y, or
T307Q and Q311H and E430H and N434A, or
T307Q and Q311H and E430H and N434H, or
T307Q and Q311H and E430H and N434Y, or
T307Q and V308P and N434Y and Y436H, or
T307H and M252Y and S254T and T256E, or
Q311H and M252Y and S254T and T256E, or
E430 H and M252Y and S254T and T256E, or
N434H and M252Y and S254T and T256E.

10. The IgG class Fc-region according to any one of embodiments 1 to 9, wherein the first Fc-region polypeptide comprises
one of the following combinations of mutations:
none, or
M252Y and S254T and T256E, or
I253A and H310A and H435A, or
H310A and H433A and Y436A,
and
one of the following mutations or combination of mutations:
none
T307H, or
T307Q, or
Q311H, or
E430 H, or
N434H, or
T307H and Q311H, or
T307H and E430H, or
T307H and N434A, or
T307H and N434H, or
T307Q and Q311H, or
T307Q and E430H, or
T307Q and N434H, or
T307Q and N434A, or
T307H and Q311H and E430H and N434A, or
T307H and Q311H and E430H and N434H, or
T307H and Q311H and E430H and N434Y, or
T307Q and Q311H and E430H and N434A, or
T307Q and Q311H and E430H and N434H, or
T307Q and Q311H and E430H and N434Y, or
T307Q and V308P and N434Y and Y436H,
and the second Fc-region polypeptide comprises
one of the following mutations or combination of mutations:
none, if the first Fc-region polypeptide comprises at least one mutation, or
T307H, or
T307Q, if the first Fc-region polypeptide does not comprises solely the T307Q mutation, or
Q311H, or
E430 H, or
N434H, or
T307H and Q311H, or
T307H and E430H, or
T307H and N434A, or
T307H and N434H, or
T307Q and Q311H, or
T307Q and E430H, or
T307Q and N434H, or
T307Q and N434A, or
M252Y and S254T and T256E, if the first Fc-region polypeptide does not comprises solely the combination M252Y and S254T and T256E of mutations, or
I253A and H310A and H435A, if the first Fc-region polypeptide does not comprises solely the combination I253A and H310A and H435A of mutations, or
H310A and H433A and Y436A, if the first Fc-region polypeptide does not comprises solely the combination H310A and H433A and Y436A of mutations, or
T307H and Q311H and E430H and N434A, or
T307H and Q311H and E430H and N434H, or
T307H and Q311H and E430H and N434Y, or
T307Q and Q311H and E430H and N434A, or
T307Q and Q311H and E430H and N434H, or
T307Q and Q311H and E430H and N434Y, or
T307Q and V308P and N434Y and Y436H.

11. The IgG class Fc-region according to any one of embodiments 1 to 10, wherein the first Fc-region polypeptide comprises the mutations I253A and H310A and H435A and the second Fc-region polypeptide comprises the mutations M252Y and S254T and T256E.

12. The IgG class Fc-region according to any one of embodiments 1 to 10, wherein the first Fc-region polypeptide comprises the mutations I253A and H310A and H435A and the second Fc-region polypeptide comprises the mutations M252Y and S254T and T256E and T307Q and N434Y.

13. The IgG class Fc-region according to any one of embodiments 1 to 10, wherein the first Fc-region polypeptide comprises the mutations I253A and H310A and H435A and the second Fc-region polypeptide comprises the mutations M252Y and S254T and T256E and T307Q and V308P and N434Y and Y436H.

14. The IgG class Fc-region according to any one of embodiments 1 to 10, wherein the first Fc-region polypeptide comprises the mutations T307H and Q311H and E430H and N434H and the second Fc-region polypeptide comprises the mutations M252Y and S254T and T256E.

15. The IgG class Fc-region according to any one of embodiments 1 to 10, wherein the first Fc-region polypeptide comprises the mutations T307H and N434H and the second Fc-region polypeptide comprises the mutations M252Y and S254T and T256E.

16. The IgG class Fc-region according to any one of embodiments 1 to 10, wherein the first Fc-region polypeptide comprises the mutations T307Q and N434A and the second Fc-region polypeptide comprises the mutations M252Y and S254T and T256E.

17. The IgG class Fc-region according to any one of embodiments 1 to 10, wherein the first Fc-region polypeptide comprises the mutations T250Q and M428L and the second Fc-region polypeptide comprises the mutations M252Y and S254T and T256E.

18. The IgG class Fc-region according to any one of embodiments 1 to 10, wherein the first Fc-region polypeptide comprises the mutations T307Q and N434H and the second Fc-region polypeptide comprises the mutations M252Y and S254T and T256E and T307Q and N434H.

19. The IgG class Fc-region according to any one of embodiments 1 to 10, wherein the first Fc-region polypeptide comprises the mutations T307H and Q311H and E430H and N434H and the second Fc-region polypeptide comprises the mutations T307H and Q311H and E430H and N434H.

20. The IgG class Fc-region according to any one of embodiments 1 to 10, wherein the first Fc-region polypeptide comprises the mutations T307H and N434H and the second Fc-region polypeptide comprises the mutations T307H and N434H.
21. The IgG class Fc-region according to any one of embodiments 1 to 10, wherein the first Fc-region polypeptide comprises the mutations T307H and N434H and M252Y and S254T and T256E and the second Fc-region polypeptide comprises the mutations T307H and N434H and M252Y and S254T and T256E.
22. The IgG class Fc-region according to any one of embodiments 1 to 10, wherein the first Fc-region polypeptide comprises the mutation N434H and the second Fc-region polypeptide comprises the mutation N434H.
23. The IgG class Fc-region according to any one of embodiments 1 to 10, wherein the first Fc-region polypeptide comprises the mutations T307Q and N434A.
24. The IgG class Fc-region according to any one of embodiments 1 to 10, wherein the first Fc-region polypeptide comprises the mutations T307H and N434H.
25. The IgG class Fc-region according to any one of embodiments 1 to 10, wherein the first Fc-region polypeptide comprises the mutations T307H and N434H and M252Y and S254T and T256E.
26. The IgG class Fc-region according to any one of embodiments 1 to 10, wherein the first Fc-region polypeptide comprises the mutation N434H.
27. An antibody comprising the IgG class Fc-region according to any one of embodiments 1 to 26.
28. The antibody according to embodiment 27, wherein the antibody is a monoclonal antibody.
29. The antibody according to any one of embodiments 27 to 28, wherein the antibody is a human, humanized, or chimeric antibody.
30. The antibody according to any one of embodiments 27 to 29, wherein the antibody is a bispecific antibody.
31. The antibody according to any one of embodiments 27 to 30, wherein the antibody is a bivalent antibody.
32. An Fc-region fusion polypeptide comprising the IgG class Fc-region according to any one of embodiments 1 to 26.
33. A pharmaceutical formulation comprising the antibody according to any one of embodiments 27 to 31 or the Fc-region fusion polypeptide according to embodiment 32.
34. The pharmaceutical formulation according to embodiment 33, wherein the pharmaceutical formulation is for use in the treatment of ocular vascular diseases.
35. The antibody according to any one of embodiments 27 to 31 or the Fc-region fusion polypeptide according to embodiment 32 for use as a medicament.
36. The use according to embodiment 35, wherein the use is for the treatment of ocular vascular diseases.
37. The use of the antibody according to any one of embodiments 27 to 31 or the Fc-region fusion polypeptide according to embodiment 32 in the manufacture of a medicament.
38. The use according to embodiment 37, wherein the use is for the manufacture of a medicament for the treatment of ocular vascular disease.
39. The antibody according to any one of embodiments 27 to 31 or the Fc-region fusion polypeptide according to embodiment 32 for use in the treatment of ocular vascular disease.
40. A method of treatment of patient suffering from ocular vascular diseases by administering the antibody according to any one of embodiments 27 to 31 or the Fc-region fusion polypeptide according to embodiment 32 to a patient in the need of such treatment.

IV. Examples

The following are examples of methods and formulations as reported herein. It is understood that various other embodiments may be practiced, given the general description provided above.

Although the foregoing invention has been described in some detail by way of illustration and example for purposes of clarity of understanding, the descriptions and examples should not be construed as limiting the scope as reported herein. The disclosures of all patent and scientific literature cited herein are expressly incorporated in their entirety by reference.

Methods

Electrospray Ionization Mass Spectrometry (ESI-MS)

Protein aliquots (50 µg) were deglycosylated by adding 0.5 µL N-Glycanase plus (Roche) and sodium phosphate buffer (0.1 M, pH 7.1) to obtain a final sample volume of 115 µL. The mixture was incubated at 37° C. for 18 h. Afterwards for reduction and denaturing 60 µL 0.5 M TCEP (Pierce) in 4 M guanidine*HCl (Pierce) and 50 µL 8 M guanidine*HCl were added. The mixture was incubated at 37° C. for 30 min. Samples were desalted by size exclusion chromatography (Sepharose G-25, isocratic, 40% acetonitrile with 2% formic acid). ESI mass spectra (+ve) were recorded on a Q-TOF instrument (maXis, Bruker) equipped with a nano ESI source (TriVersa NanoMate, Advion). MS parameter settings were as follows: Transfer: Funnel RF, 400 Vpp; ISCID Energy, 0 eV; Multipole RF, 400 Vpp; Quadrupole: Ion Energy, 4.0 eV; Low Mass, 600 m/z; Source: Dry Gas, 8 L/min; Dry Gas Temperature, 160° C.; Collision Cell: Collision Energy, 10 eV; Collision RF: 2000 Vpp; Ion Cooler: Ion Cooler RF, 300 Vpp; Transfer Time: 120 µs; Pre Puls Storage, 10 µs; scan range m/z 600 to 2000. For data evaluation in-house developed software (MassAnalyzer) was used.

FcRn Surface Plasmon Resonance (SPR) Analysis

The binding properties of wild-type antibody and the mutants to FcRn were analyzed by surface plasmon resonance (SPR) technology using a BIAcore T100 instrument (BIAcore AB, Uppsala, Sweden). This system is well established for the study of molecular interactions. It allows a continuous real-time monitoring of ligand/analyte bindings and, thus, the determination of kinetic parameters in various assay settings. SPR-technology is based on the measurement of the refractive index close to the surface of a gold coated biosensor chip. Changes in the refractive index indicate mass changes on the surface caused by the interaction of immobilized ligand with analyte injected in solution. If molecules bind to an immobilized ligand on the surface the mass increases, in case of dissociation the mass decreases. In the current assay, the FcRn receptor was immobilized onto a BIAcore CM5-biosensor chip (GE Healthcare Bioscience, Uppsala, Sweden) via amine coupling to a level of 400 Response units (RU). The assay was carried out at room temperature with PBS, 0.05% Tween-20™ pH 6.0 (GE Healthcare Bioscience) as running and dilution buffer. 200 nM of antibody samples were injected at a flow rate of 50 µL/min at room temperature. Association time was 180 seconds, dissociation phase took 360 seconds. Regeneration of the chip surface was reached by a short injection of HBS-P, pH 8.0. Evaluation of SPR-data was performed by comparison of the biological response signal height at 180 seconds after injection and at 300 seconds after injection. The corresponding parameters are the RU max level (180 seconds after injection) and late stability (300 seconds after end of injection).

Protein a Surface Plasmon Resonance (SPR) Analysis

The assay is based on surface plasmon resonance spectroscopy. Protein A is immobilized onto the surface of a SPR biosensor. By injecting the sample into the flow cells of the SPR spectrometer it forms a complex with the immobilized protein A resulting in an increasing mass on the sensor chip surface, and therefore to a higher response (as 1 RU is defined as 1 pg/mm$^2$). Afterwards the sensor chip is regenerated by dissolving the sample-protein A-complex. The gained responses are then evaluated for the signal high in response units (RU) and the dissociation behavior.

Around 3,500 response units (RU) of protein A (20 μg/mL) were coupled onto a CMS chip (GE Healthcare) at pH 4.0 by using the amine coupling kit of GE Healthcare.

The sample and system buffer was HBS-P+(0.01 M HEPES, 0.15 M NaCl, 0.005% Surfactant P20 Sterile-filtered, pH 7.4). Flow cell temperature was set to 25° C. and sample compartment temperature to 12° C. The system was primed with running buffer. Then, a 5 nM solutions of the sample constructs were injected for 120 seconds with a flow rate of 30 μL/min, followed by a 300 seconds dissociation phase. Then the sensor chip surface was regenerated by two 30 seconds long injections of Glycine-HCl pH 1.5 at a flow rate of 30 μL/min. Each sample was measured as a triplicate.

The term "with (the) mutation IHH-AAA" as used herein refers to the combination of the mutations I253A (Ile253Ala), H310A (His310Ala), and H435A (His435Ala) in a constant heavy chain region of IgG1 or IgG4 subclass (numbering according to EU Index of Kabat), the term "with (the) mutation HHY-AAA" as used herein refers the combination of the mutations H310A (His310Ala), H433A (His433Ala) and Y436A (Tyr436Ala) in a constant heavy chain region of IgG1 or IgG4 subclass (numbering according to EU Index of Kabat), the term "with (the) mutation P329G LALA" as used herein refers to the combination of the mutations L234A (Leu234Ala), L235A (Leu235Ala) and P329G (Pro329Gly) in a constant heavy chain region of IgG1 subclass (numbering according to EU Index of Kabat), and the term "with (the) mutation SPLE" as used herein refers to the combination of the mutations S228P (Ser228Pro) and L235E (Leu235Glu) a constant heavy chain region of IgG4 subclass (numbering according to EU Index of Kabat).

General

General information regarding the nucleotide sequences of human immunoglobulin light and heavy chains is given in: Kabat, E. A., et al., Sequences of Proteins of Immunological Interest, 5th ed., Public Health Service, National Institutes of Health, Bethesda, Md. (1991). Amino acid residues of antibody chains are numbered and referred to according to EU numbering (Edelman, G. M., et al., Proc. Natl. Acad. Sci. USA 63 (1969) 78-85; Kabat, E. A., et al., Sequences of Proteins of Immunological Interest, 5th ed., Public Health Service, National Institutes of Health, Bethesda, Md. (1991)).

Recombinant DNA Techniques

Standard methods were used to manipulate DNA as described in Sambrook, J. et al., Molecular Cloning: A laboratory manual; Cold Spring Harbor Laboratory Press, Cold Spring Harbor, N.Y. (1989). The molecular biological reagents were used according to the manufacturer's instructions.

Gene Synthesis

Desired gene segments were ordered according to given specifications at Geneart (Regensburg, Germany).

DNA Sequence Determination

DNA sequences were determined by double strand sequencing performed at MediGenomix GmbH (Martinsried, Germany) or SequiServe GmbH (Vaterstetten, Germany).

DNA and protein sequence analysis and sequence data management

The GCG's (Genetics Computer Group, Madison, Wis.) Software Package version 10.2 and Infomax's Vector NT1 Advance suite version 8.0 was used for sequence creation, mapping, analysis, annotation and illustration.

Expression Vectors

For the expression of the described antibodies expression plasmids for transient expression (e.g. in HEK293-F cells) based either on a cDNA organization with or without a CMV-Intron A promoter or on a genomic organization with a CMV promoter were used.

The transcription unit of the antibody gene was composed of the following elements:

unique restriction site(s) at the 5' end, the immediate early enhancer and promoter from the human cytomegalovirus, in the case of the cDNA organization the Intron A sequence, a 5'-untranslated region of a human immunoglobulin gene, a nucleic acid encoding an immunoglobulin heavy chain signal sequence, a nucleic acid encoding the human antibody chain (wild-type or with domain exchange) either as cDNA or in genomic organization with the immunoglobulin exon-intron organization, a 3' non-translated region with a polyadenylation signal sequence, and unique restriction site(s) at the 3' end.

Beside the antibody expression cassette the plasmids contained:

an origin of replication which allows replication of this plasmid in *E. coli,* a β-lactamase gene which confers ampicillin resistance in *E. coli,* and the dihydrofolate reductase gene from Mus musculus as a selectable marker in eukaryotic cells.

The nucleic acids encoding the antibody chains were generated by PCR and/or gene synthesis and assembled by known recombinant methods and techniques by connection of the according nucleic acid segments e.g. using unique restriction sites in the respective vectors. The subcloned nucleic acid sequences were verified by DNA sequencing. For transient transfections larger quantities of the plasmids were prepared by plasmid preparation from transformed *E. coli* cultures (Nucleobond AX, Macherey-Nagel).

Cell Culture Techniques

Standard cell culture techniques were used as described in Current Protocols in Cell Biology (2000), Bonifacino, J. S., Dasso, M., Harford, J. B., Lippincott-Schwartz, J. and Yamada, K. M. (eds.), John Wiley & Sons, Inc.

The bispecific antibodies were expressed by transient co-transfection of the respective expression plasmids in in HEK293-F cells growing in suspension as described below.

Example 1

Expression and Purification
Transient Transfections in HEK293-F System

The monospecific and bispecific antibodies were generated by transient transfection with the respective plasmids (e.g. encoding the heavy and modified heavy chain, as well as the corresponding light and modified light chain) using the HEK293-F system (Invitrogen) according to the manufacturer's instruction. Briefly, HEK293-F cells (Invitrogen) growing in suspension either in a shake flask or in a stirred fermenter in serum-free FreeStyle™ 293 expression medium (Invitrogen) were transfected with a mix of the respective expression plasmids and 293Fectin™ or fectin (Invitrogen). For 2 L shake flask (Corning) HEK293-F cells were seeded at a density of $1*10^6$ cells/mL in 600 mL and incubated at 120 rpm, 8% $CO_2$. The day after the cells were transfected at a cell density of approx. $1.5*10^6$ cells/mL with approx. 42 mL of a mixture of A) 20 mL Opti-MEM (Invitrogen) with 600 μg total plasmid DNA (1 μg/mL) encoding the heavy or modified heavy chain, respectively and the corresponding light chain in an equimolar ratio and B) 20 ml Opti-MEM with 1.2 mL 293 fectin or fectin (2 μL/mL). According to the glucose consumption glucose solution was added during the course of the fermentation. The supernatant containing the secreted antibody was harvested after 5-10 days and antibodies were either directly purified from the supernatant or the supernatant was frozen and stored.

Purification

Bispecific antibodies were purified from cell culture supernatants by affinity chromatography using MabSelectSure-Sepharose™ (for non-IHH-AAA mutants) (GE Healthcare, Sweden) or KappaSelect-Agarose (for IHH-AAA mutants) (GE Healthcare, Sweden), hydrophobic interaction chromatography using butyl-Sepharose (GE Healthcare, Sweden) and Superdex 200 size exclusion (GE Healthcare, Sweden) chromatography.

Briefly, sterile filtered cell culture supernatants were captured on a MabSelectSuRe resin equilibrated (non-IHH-AAA mutations and wild-type antibodies) with PBS buffer (10 mM $Na_2HPO_4$, 1 mM $KH_2PO_4$, 137 mM NaCl and 2.7 mM KCl, pH 7.4), washed with equilibration buffer and eluted with 25 mM sodium citrate at pH 3.0. The IHH-AAA mutants were captured on a KappaSelect resin equilibrated with 25 mM Tris, 50 mM NaCl, pH 7.2, washed with equilibration buffer and eluted with 25 mM sodium citrate pH 2.9. The eluted antibody fractions were pooled and neutralized with 2 M Tris, pH 9.0. The antibody pools were prepared for hydrophobic interaction chromatography by adding 1.6 M ammonium sulfate solution to a final concentration of 0.8 M ammonium sulfate and the pH adjusted to pH 5.0 using acetic acid. After equilibration of the butyl-Sepharose resin with 35 mM sodium acetate, 0.8 M ammonium sulfate, pH 5.0, the antibodies were applied to the resin, washed with equilibration buffer and eluted with a linear gradient to 35 mM sodium acetate pH 5.0. The (monospecific or bispecific) antibody containing fractions were pooled and further purified by size exclusion chromatography using a Superdex 200 26/60 GL (GE Healthcare, Sweden) column equilibrated with 20 mM histidine, 140 mM NaCl, pH 6.0. The (monospecific or bispecific) antibody containing fractions were pooled, concentrated to the required concentration using Vivaspin ultrafiltration devices (Sartorius Stedim Biotech S.A., France) and stored at −80° C.

Purity and antibody integrity were analyzed after each purification step by CE-SDS using microfluidic Labchip technology (Caliper Life Science, USA). Five μL of protein solution was prepared for CE-SDS analysis using the HT Protein Express Reagent Kit according manufacturer's instructions and analyzed on LabChip GXII system using a HT Protein Express Chip. Data were analyzed using LabChip GX Software.

The aggregate content of antibody samples was analyzed by high-performance SEC using a Superdex 200 analytical size-exclusion column (GE Healthcare, Sweden) in 2×PBS (20 mM $Na_2HPO_4$, 2 mM $KH_2PO_4$, 274 mM NaCl and 5.4 mM KCl, pH 7.4) running buffer at 25° C. 25 μg protein were injected on the column at a flow rate of 0.75 mL/min and eluted isocratic over 50 minutes.

Example 2

FcRn Chromatography
Coupling to Streptavidin Sepharose:

One gram streptavidin sepharose (GE Healthcare) was added to the biotinylated and dialyzed receptor and incubated for two hours with shaking. The receptor derivatized sepharose was filled in a 1 mL XK column (GE Healthcare).

Chromatography Using the FcRn Affinity Column:

Conditions:
column dimensions: 50 mm×5 mm
bed height: 5 cm
loading: 50 μg sample
equilibration buffer: 20 mM MES, with 150 mM NaCl, adjusted to pH 5.5
elution buffer: 20 mM Tris/HCl, with 150 mM NaCl, adjusted to pH 8.8
elution: 7.5 CV equilibration buffer, in 30 CV to 100% elution buffer, 10 CV elution buffer

---

The invention claimed is:

1. An IgG class Fc-region comprising a first variant Fc-region polypeptide and a second variant Fc-region polypeptide,
wherein:
a) the first variant Fc-region polypeptide is derived from a first parent IgG class Fc-region polypeptide and the second variant Fc-region polypeptide is derived from a second parent IgG class Fc-region polypeptide, whereby the first parent IgG class Fc-region polypeptide is identical to or different from the second parent IgG class Fc-region polypeptide, and
b) the first variant Fc-region polypeptide differs from the second variant Fc-region polypeptide in one or more amino acid residues other than those amino acid residues in which the first parent IgG class Fc-region polypeptide differs from the second parent IgG class Fc-region polypeptide, and
c) the IgG class Fc-region comprising the first variant Fc-region polypeptide and the second variant Fc-region polypeptide has an affinity to a human neonatal Fc-receptor that is different than that of an IgG class Fc-region comprising the first parent IgG class Fc-region polypeptide of a) and the second parent IgG class Fc-region polypeptide of a),
wherein either the first variant Fc-region polypeptide or the second variant Fc-region polypeptide or both variant Fc-region polypeptides comprise independently of each other T307H and N434A substitutions (Kabat EU index numbering system).

2. The IgG class Fc-region according to claim 1, wherein the amino acid residues in which the first parent IgG class Fc-region polypeptide differs from the second parent IgG class Fc-region polypeptide promote the formation of a heterodimeric IgG class Fc-region.

3. The IgG class Fc-region according to claim 1, wherein:
i) the first parent IgG class Fc-region polypeptide is selected from the group consisting of: a human IgG1 Fc-region polypeptide, a human IgG2 Fc-region polypeptide, a human IgG3 Fc-region polypeptide, a human IgG4 Fc-region polypeptide, a human IgG1 Fc-region polypeptide comprising the mutations L234A and L235A, a human IgG1 Fc-region polypeptide comprising the mutations Y349C, T366S, L368A, and Y407V, a human IgG1 Fc-region polypeptide comprising the mutations L234A, L235A, Y349C, T366S, L368A, and Y407V, a human IgG1 Fc-region polypeptide comprising the mutation P329G, a human IgG1 Fc-region polypeptide comprising the mutations L234A, L235A, and P329G, a human IgG1 Fc-region polypeptide comprising the mutations P329G, Y349C, T366S, L368A, and Y407V, a human IgG1 Fc-region polypeptide comprising the mutations L234A, L235A, P329G, Y349C, T366S, L368A, and Y407V, a human IgG4 Fc-region polypeptide comprising the mutations S228P and L235E, a human IgG4 Fc-region polypeptide comprising the mutations S228P, L235E, and P329G, a human IgG4 Fc-region polypeptide comprising the mutations Y349C, T366S, L368A, and Y407V, a human IgG4 Fc-region polypeptide comprising the mutations S228P, L235E, Y349C, T366S, L368A, and Y407V, a human IgG4 Fc-region polypeptide comprising the mutation P329G, a human IgG4 Fc-region polypeptide comprising the mutations P329G, Y349C, T366S, L368A, and Y407V, a human IgG4 Fc-region polypeptide comprising the mutations S228P, L235E, P329G, Y349C, T366S, L368A, and Y407V, a human IgG1, IgG2 or IgG4 comprising the mutation K392D, and a human IgG3 comprising the mutation N392D (Kabat EU index numbering system);
and ii) the second parent IgG class Fc-region polypeptide is selected from the group consisting of: a human IgG1 Fc-region polypeptide, a human IgG2 Fc-region polypeptide, a human IgG3 Fc-region polypeptide, a human IgG4 Fc-region polypeptide, a human IgG1 Fc-region polypeptide comprising the mutations L234A and L235A, a human IgG1 Fc-region polypeptide comprising the mutations S354C and T366W, a human IgG1 Fc-region polypeptide comprising the mutations L234A, L235A, S354C, and T366W, a human IgG1 Fc-region polypeptide comprising the mutation P329G, a human IgG1 Fc-region polypeptide comprising the mutations L234A, L235A, and P329G, a human IgG1 Fc-region polypeptide comprising the mutations P329G, S354C, and T366W, a human IgG1 Fc-region polypeptide comprising the mutations L234A, L235A, P329G, S354C, and T366W, a human IgG4 Fc-region polypeptide comprising the mutations S228P and L235E, a human IgG4 Fc-region polypeptide comprising the mutations S228P, L235E, and P329G, a human IgG4 Fc-region polypeptide comprising the mutations S354C and T366W, a human IgG4 Fc-region polypeptide comprising the mutations S228P, L235E, S354C, and T366W, a human IgG4 Fc-region polypeptide comprising the mutation P329G, a human IgG4 Fc-region polypeptide comprising the mutations P329G, S354C, and T366W, a human IgG4 Fc-region polypeptide comprising the mutations S228P, L235E, P329G, S354C, and T366W, a human IgG1 comprising one or more of the mutations D399K, D356K, and E357K, and a human IgG2, IgG3 or IgG4 comprising one or more of the mutations D399K, E356K, and E357K (Kabat EU index numbering system).

4. The IgG class Fc-region according to claim 1, wherein:
i) the first parent IgG class Fc-region polypeptide is a human IgG1 Fc-region polypeptide and the second parent IgG class Fc-region polypeptide is a human IgG1 Fc-region polypeptide; or
ii) the first parent IgG class Fc-region polypeptide is a human IgG1 Fc-region polypeptide comprising the mutations L234A and L235A, and the second parent IgG class Fc-region polypeptide is a human IgG1 Fc-region polypeptide comprising the mutations L234A and L235A (Kabat EU index numbering system); or iii) the first parent IgG class Fc-region polypeptide is a human IgG1 Fc-region polypeptide comprising the mutations L234A, L235A, and P329G, and the second parent IgG class Fc-region polypeptide is a human IgG1 Fc-region polypeptide comprising the mutations L234A, L235A, and P329G (Kabat EU index numbering system); or
iv) the first parent IgG class Fc-region polypeptide is a human IgG1 Fc-region polypeptide comprising the mutations L234A, L235A, S354C, and T366W, and the second parent IgG class Fc-region polypeptide is a human IgG1 Fc-region polypeptide comprising the mutations L234A, L235A, Y349C, T366S, L368A, and Y407V (Kabat EU index numbering system); or
v) the first parent IgG class Fc-region polypeptide is a human IgG1 Fc-region polypeptide comprising the mutations L234A, L235A, P329G, S354C, and T366W, and the second parent IgG class Fc-region polypeptide is a human IgG1 Fc-region polypeptide comprising the mutations L234A, L235A, P329G, Y349C, T366S, L368A, and Y407V (Kabat EU index numbering system); or
vi) the first parent IgG class Fc-region polypeptide is a human IgG4 Fc-region polypeptide and the second parent IgG class Fc-region polypeptide is a human IgG4 Fc-region polypeptide; or
vii) the first parent IgG class Fc-region polypeptide is a human IgG4 Fc-region polypeptide comprising the mutations S228P and L235E, and the second parent IgG class Fc-region polypeptide is a human IgG4 Fc-region polypeptide comprising the mutations S228P and L235E (Kabat EU index numbering system); or
viii) the first parent IgG class Fc-region polypeptide is a human IgG4 Fc-region polypeptide comprising the mutations S228P, L235E, and P329G, and the second parent IgG class Fc-region polypeptide is a human IgG4 Fc-region polypeptide comprising the mutations S228P, L235E, and P329G (Kabat EU index numbering system); or
ix) the first parent IgG class Fc-region polypeptide is a human IgG4 Fc-region polypeptide comprising the mutations S228P, L235E, S354C, and T366W, and the second parent IgG class Fc-region polypeptide is a human IgG4 Fc-region polypeptide comprising the mutations S228P, L235E, Y349C, T366S, L368A, and Y407V (Kabat EU index numbering system); or
x) the first parent IgG class Fc-region polypeptide is a human IgG4 Fc-region polypeptide comprising the mutations S228P, L235E, P329G, S354C, and T366W, and the second parent IgG class Fc-region polypeptide is a human IgG4 Fc-region polypeptide comprising the mutations S228P, L235E, P329G, Y349C, T366S, L368A, and Y407V (Kabat EU index numbering system); or
xi) the first parent IgG class Fc-region polypeptide is: (a) a human IgG1, IgG2, or IgG4 Fc-region polypeptide comprising the mutation K392D, or (b) a human IgG3 Fc-region polypeptide comprising the mutation N392D, and the second parent IgG class Fc-region polypeptide is: (c) a human IgG1 Fc-region polypeptide comprising one or more of the mutations D399K, D356K, and E357K or (d) a human IgG2, IgG3 or IgG4 Fc-region polypeptide comprising one or more of the mutations D399K, E356K, and E357K (Kabat EU index numbering system).

5. An antibody comprising the IgG class Fc-region according to claim 1.

6. The antibody according to claim 5, wherein the antibody is a monoclonal antibody.

7. The antibody according to claim 5, wherein the antibody is a human, humanized, or chimeric antibody.

8. The antibody according to claim 5, wherein the antibody is a bispecific antibody.

9. The antibody according to claim 5, wherein the antibody is a bivalent antibody.

10. A pharmaceutical formulation comprising the antibody according to claim 5.

11. A method for making an IgG class Fc-region, the method comprising:
   a) cultivating a mammalian cell comprising one or more nucleic acids encoding the first and second variant Fc-region polypeptides according to claim 1; and
   b) recovering the IgG class Fc-region from the cultivation medium.

12. The method of claim 11, wherein the mammalian cell is a CHO cell.

* * * * *

SEQUENCE LISTING

<160> NUMBER OF SEQ ID NOS: 30

<210> SEQ ID NO 1
<211> LENGTH: 107
<212> TYPE: PRT
<213> ORGANISM: Homo sapiens

<400> SEQUENCE: 1

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

```
Trp Asp Val Ser His Glu Asp Pro Glu Val Lys Phe Asn Trp Tyr Val
        35                  40                  45

Asp Gly Val Glu Val His Asn Ala Lys Thr Lys Pro Arg Glu Glu Gln
 50                  55                  60

Glu Ser Thr Tyr Arg Trp Ser Val Leu Thr Val Leu His Gln Asp Trp
 65                  70                  75                  80

Leu Asn Gly Lys Glu Tyr Lys Cys Lys Val Ser Asn Lys Ala Leu Pro
                 85                  90                  95

Ala Pro Ile Glu Lys Thr Ile Ser Lys Ala Lys
                100                 105

<210> SEQ ID NO 2
<211> LENGTH: 106
<212> TYPE: PRT
<213> ORGANISM: Homo sapiens

<400> SEQUENCE: 2

Gly Gln Pro Arg Glu Pro Gln Val Tyr Thr Leu Pro Pro Ser Arg Asp
 1               5                  10                  15

Glu Leu Thr Lys Asn Gln Val Ser Leu Thr Cys Leu Val Lys Gly Phe
                20                  25                  30

Tyr Pro Ser Asp Ile Ala Val Glu Trp Glu Ser Asn Gly Gln Pro Glu
            35                  40                  45

Asn Asn Tyr Lys Thr Thr Pro Pro Val Leu Asp Ser Asp Gly Ser Phe
 50                  55                  60

Phe Leu Tyr Ser Lys Leu Thr Val Asp Lys Ser Arg Trp Gln Gln Gly
 65                  70                  75                  80

Asn Val Phe Ser Cys Ser Val Met His Glu Ala Leu His Asn His Tyr
                 85                  90                  95

Thr Gln Lys Ser Leu Ser Leu Ser Pro Gly
                100                 105

<210> SEQ ID NO 3
<211> LENGTH: 227
<212> TYPE: PRT
<213> ORGANISM: Homo sapiens

<400> SEQUENCE: 3

Asp Lys Thr His Thr Cys Pro Pro Cys Pro Ala Pro Glu Leu Leu Gly
 1               5                  10                  15

Gly Pro Ser Val Phe Leu Phe Pro Pro Lys Pro Lys Asp Thr Leu Met
                20                  25                  30

Ile Ser Arg Thr Pro Glu Val Thr Cys Val Val Val Asp Val Ser His
            35                  40                  45

Glu Asp Pro Glu Val Lys Phe Asn Trp Tyr Val Asp Gly Val Glu Val
 50                  55                  60

His Asn Ala Lys Thr Lys Pro Arg Glu Glu Gln Tyr Asn Ser Thr Tyr
 65                  70                  75                  80

Arg Val Val Ser Val Leu Thr Val Leu His Gln Asp Trp Leu Asn Gly
                 85                  90                  95

Lys Glu Tyr Lys Cys Lys Val Ser Asn Lys Ala Leu Pro Ala Pro Ile
                100                 105                 110

Glu Lys Thr Ile Ser Lys Ala Lys Gly Gln Pro Arg Glu Pro Gln Val
            115                 120                 125

Tyr Thr Leu Pro Pro Ser Arg Asp Glu Leu Thr Lys Asn Gln Val Ser
        130                 135                 140
```

-continued

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225

<210> SEQ ID NO 4
<211> LENGTH: 223
<212> TYPE: PRT
<213> ORGANISM: Homo sapiens

<400> SEQUENCE: 4

Val Glu Cys Pro Pro Cys Pro Ala Pro Pro Val Ala Gly Pro Ser Val
1               5                   10                  15

Phe Leu Phe Pro Pro Lys Pro Lys Asp Thr Leu Met Ile Ser Arg Thr
            20                  25                  30

Pro Glu Val Thr Cys Val Val Asp Val Ser His Glu Asp Pro Glu
        35                  40                  45

Val Gln Phe Asn Trp Tyr Val Asp Gly Val Glu Val His Asn Ala Lys
    50                  55                  60

Thr Lys Pro Arg Glu Glu Gln Phe Asn Ser Thr Phe Arg Val Val Ser
65                  70                  75                  80

Val Leu Thr Val Val His Gln Asp Trp Leu Asn Gly Lys Glu Tyr Lys
                85                  90                  95

Cys Lys Val Ser Asn Lys Gly Leu Pro Ala Pro Ile Glu Lys Thr Ile
            100                 105                 110

Ser Lys Thr Lys Gly Gln Pro Arg Glu Pro Gln Val Tyr Thr Leu Pro
        115                 120                 125

Pro Ser Arg Glu Glu Met Thr Lys Asn Gln Val Ser Leu Thr Cys Leu
    130                 135                 140

Val Lys Gly Phe Tyr Pro Ser Asp Ile Ser Val Glu Trp Glu Ser Asn
145                 150                 155                 160

Gly Gln Pro Glu Asn Asn Tyr Lys Thr Thr Pro Pro Met Leu Asp Ser
                165                 170                 175

Asp Gly Ser Phe Phe Leu Tyr Ser Lys Leu Thr Val Asp Lys Ser Arg
            180                 185                 190

Trp Gln Gln Gly Asn Val Phe Ser Cys Ser Val Met His Glu Ala Leu
        195                 200                 205

His Asn His Tyr Thr Gln Lys Ser Leu Ser Leu Ser Pro Gly Lys
    210                 215                 220

<210> SEQ ID NO 5
<211> LENGTH: 227
<212> TYPE: PRT
<213> ORGANISM: Homo sapiens

<400> SEQUENCE: 5

Asp Thr Pro Pro Pro Cys Pro Arg Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Gln Phe Lys Trp Tyr Val Asp Gly Val Glu Val
 50                  55                  60

His Asn Ala Lys Thr Lys Pro Arg Glu Glu Gln Tyr Asn Ser Thr Phe
 65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Thr Lys Gly Gln Pro Arg Glu Pro Gln Val
        115                 120                 125

Tyr Thr Leu Pro Pro Ser Arg Glu Glu Met Thr Lys Asn Gln Val Ser
130                 135                 140

Leu Thr Cys Leu Val Lys Gly Phe Tyr Pro Ser Asp Ile Ala Val Glu
145                 150                 155                 160

Trp Glu Ser Ser Gly Gln Pro Glu Asn Asn Tyr Asn Thr Thr Pro Pro
                165                 170                 175

Met Leu Asp Ser Asp Gly Ser Phe Phe Leu Tyr Ser Lys Leu Thr Val
            180                 185                 190

Asp Lys Ser Arg Trp Gln Gln Gly Asn Ile Phe Ser Cys Ser Val Met
        195                 200                 205

His Glu Ala Leu His Asn Arg Phe Thr Gln Lys Ser Leu Ser Leu Ser
    210                 215                 220

Pro Gly Lys
225

<210> SEQ ID NO 6
<211> LENGTH: 229
<212> TYPE: PRT
<213> ORGANISM: Homo sapiens

<400> SEQUENCE: 6

Glu Ser Lys Tyr Gly Pro Pro Cys Pro Ser Cys Pro Ala Pro Glu Phe
1               5                   10                  15

Leu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
 50                  55                  60

Glu Val His Asn Ala Lys Thr Lys Pro Arg Glu Glu Gln Phe Asn Ser
 65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Ser Gln Glu Glu Met Thr Lys Asn Gln
130                 135                 140

Val Ser Leu Thr Cys Leu Val Lys Gly Phe Tyr Pro Ser Asp Ile Ala

```
                145                 150                 155                 160
Val Glu Trp Glu Ser Asn Gly Gln Pro Glu Asn Asn Tyr Lys Thr Thr
                    165                 170                 175

Pro Pro Val Leu Asp Ser Asp Gly Ser Phe Phe Leu Tyr Ser Arg Leu
                180                 185                 190

Thr Val Asp Lys Ser Arg Trp Gln Glu Gly Asn Val Phe Ser Cys Ser
                195                 200                 205

Val Met His Glu Ala Leu His Asn His Tyr Thr Gln Lys Ser Leu Ser
            210                 215                 220

Leu Ser Leu Gly Lys
225

<210> SEQ ID NO 7
<211> LENGTH: 227
<212> TYPE: PRT
<213> ORGANISM: Artificial Sequence
<220> FEATURE:
<223> OTHER INFORMATION: human IgG1 Fc-region derived Fc-region
      polypeptide with the mutations L234A, L235A

<400> SEQUENCE: 7

Asp Lys Thr His Thr Cys Pro Pro Cys Pro Ala Pro Glu Ala Ala Gly
1               5                   10                  15

Gly Pro Ser Val Phe Leu Phe Pro Pro Lys Pro Lys Asp Thr Leu Met
                20                  25                  30

Ile Ser Arg Thr Pro Glu Val Thr Cys Val Val Val Asp Val Ser His
            35                  40                  45

Glu Asp Pro Glu Val Lys Phe Asn Trp Tyr Val Asp Gly Val Glu Val
        50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Glu Leu Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225

<210> SEQ ID NO 8
<211> LENGTH: 227
<212> TYPE: PRT
<213> ORGANISM: Artificial Sequence
<220> FEATURE:
```

<223> OTHER INFORMATION: human IgG1 Fc-region derived Fc-region
polypeptide with Y349C, T366S, L368A and Y407V mutations

<400> SEQUENCE: 8

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Cys Thr Leu Pro Pro Ser Arg Asp Glu Leu Thr Lys Asn Gln Val Ser
    130                 135                 140

Leu Ser Cys Ala Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Val Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225

<210> SEQ ID NO 9
<211> LENGTH: 227
<212> TYPE: PRT
<213> ORGANISM: Artificial Sequence
<220> FEATURE:
<223> OTHER INFORMATION: human IgG1 Fc-region derived Fc-region
polypeptide with S354C, T366W mutations

<400> SEQUENCE: 9

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Cys Arg Asp Glu Leu Thr Lys Asn Gln Val Ser
    130                 135                 140

Leu Trp Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225

<210> SEQ ID NO 10
<211> LENGTH: 227
<212> TYPE: PRT
<213> ORGANISM: Artificial Sequence
<220> FEATURE:
<223> OTHER INFORMATION: human IgG1 Fc-region derived Fc-region
      polypeptide with L234A, L235A mutations and Y349C, T366S, L368A,
      Y407V mutations

<400> SEQUENCE: 10

Asp Lys Thr His Thr Cys Pro Pro Cys Pro Ala Pro Glu Ala Ala Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Cys Thr Leu Pro Pro Ser Arg Asp Glu Leu Thr Lys Asn Gln Val Ser
    130                 135                 140

Leu Ser Cys Ala Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Val Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser

Pro Gly Lys
225

<210> SEQ ID NO 11
<211> LENGTH: 227
<212> TYPE: PRT
<213> ORGANISM: Artificial Sequence
<220> FEATURE:
<223> OTHER INFORMATION: human IgG1 Fc-region derived Fc-region
     polypeptide with a L234A, L235A and S354C, T366W mutations

<400> SEQUENCE: 11

Asp Lys Thr His Thr Cys Pro Pro Cys Pro Ala Pro Glu Ala Ala Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Cys Arg Asp Glu Leu Thr Lys Asn Gln Val Ser
    130                 135                 140

Leu Trp Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225

<210> SEQ ID NO 12
<211> LENGTH: 227
<212> TYPE: PRT
<213> ORGANISM: Artificial Sequence
<220> FEATURE:
<223> OTHER INFORMATION: human IgG1 Fc-region derived Fc-region
     polypeptide with a P329G mutation

<400> SEQUENCE: 12

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His

```
            35                  40                  45
Glu Asp Pro Glu Val Lys Phe Asn Trp Tyr Val Asp Gly Val Glu Val
 50                  55                  60
His Asn Ala Lys Thr Lys Pro Arg Glu Glu Gln Tyr Asn Ser Thr Tyr
 65                  70                  75                  80
Arg Val Val Ser Val Leu Thr Val Leu His Gln Asp Trp Leu Asn Gly
                 85                  90                  95
Lys Glu Tyr Lys Cys Lys Val Ser Asn Lys Ala Leu Gly Ala Pro Ile
            100                 105                 110
Glu Lys Thr Ile Ser Lys Ala Lys Gly Gln Pro Arg Glu Pro Gln Val
            115                 120                 125
Tyr Thr Leu Pro Pro Ser Arg Asp Glu Leu Thr Lys Asn Gln Val Ser
130                 135                 140
Leu Thr Cys Leu Val Lys Gly Phe Tyr Pro Ser Asp Ile Ala Val Glu
145                 150                 155                 160
Trp Glu Ser Asn Gly Gln Pro Glu Asn Asn Tyr Lys Thr Thr Pro Pro
                165                 170                 175
Val Leu Asp Ser Asp Gly Ser Phe Phe Leu Tyr Ser Lys Leu Thr Val
            180                 185                 190
Asp Lys Ser Arg Trp Gln Gln Gly Asn Val Phe Ser Cys Ser Val Met
            195                 200                 205
His Glu Ala Leu His Asn His Tyr Thr Gln Lys Ser Leu Ser Leu Ser
            210                 215                 220
Pro Gly Lys
225

<210> SEQ ID NO 13
<211> LENGTH: 227
<212> TYPE: PRT
<213> ORGANISM: Artificial Sequence
<220> FEATURE:
<223> OTHER INFORMATION: human IgG1 Fc-region derived Fc-region
      polypeptide with L234A, L235A mutations and P329G mutation

<400> SEQUENCE: 13

Asp Lys Thr His Thr Cys Pro Pro Cys Pro Ala Pro Glu Ala Ala Gly
 1               5                  10                  15
Gly Pro Ser Val Phe Leu Phe Pro Pro Lys Pro Lys Asp Thr Leu Met
                 20                  25                  30
Ile Ser Arg Thr Pro Glu Val Thr Cys Val Val Val Asp Val Ser His
             35                  40                  45
Glu Asp Pro Glu Val Lys Phe Asn Trp Tyr Val Asp Gly Val Glu Val
 50                  55                  60
His Asn Ala Lys Thr Lys Pro Arg Glu Glu Gln Tyr Asn Ser Thr Tyr
 65                  70                  75                  80
Arg Val Val Ser Val Leu Thr Val Leu His Gln Asp Trp Leu Asn Gly
                 85                  90                  95
Lys Glu Tyr Lys Cys Lys Val Ser Asn Lys Ala Leu Gly Ala Pro Ile
            100                 105                 110
Glu Lys Thr Ile Ser Lys Ala Lys Gly Gln Pro Arg Glu Pro Gln Val
            115                 120                 125
Tyr Thr Leu Pro Pro Ser Arg Asp Glu Leu Thr Lys Asn Gln Val Ser
130                 135                 140
Leu Thr Cys Leu Val Lys Gly Phe Tyr Pro Ser Asp Ile Ala Val Glu
145                 150                 155                 160
```

Trp Glu Ser Asn Gly Gln Pro Glu Asn Asn Tyr Lys Thr Thr Pro Pro
            165                 170                 175

Val Leu Asp Ser Asp Gly Ser Phe Phe Leu Tyr Ser Lys Leu Thr Val
        180                 185                 190

Asp Lys Ser Arg Trp Gln Gln Gly Asn Val Phe Ser Cys Ser Val Met
    195                 200                 205

His Glu Ala Leu His Asn His Tyr Thr Gln Lys Ser Leu Ser Leu Ser
210                 215                 220

Pro Gly Lys
225

<210> SEQ ID NO 14
<211> LENGTH: 227
<212> TYPE: PRT
<213> ORGANISM: Artificial Sequence
<220> FEATURE:
<223> OTHER INFORMATION: human IgG1 Fc-region derived Fc-region
      polypeptide with a P239G mutation and Y349C, T366S, L368A, Y407V
      mutations

<400> SEQUENCE: 14

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Gly Ala Pro Ile
            100                 105                 110

Glu Lys Thr Ile Ser Lys Ala Lys Gly Gln Pro Arg Glu Pro Gln Val
        115                 120                 125

Cys Thr Leu Pro Pro Ser Arg Asp Glu Leu Thr Lys Asn Gln Val Ser
130                 135                 140

Leu Ser Cys Ala Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
            165                 170                 175

Val Leu Asp Ser Asp Gly Ser Phe Phe Leu Val Ser Lys Leu Thr Val
        180                 185                 190

Asp Lys Ser Arg Trp Gln Gln Gly Asn Val Phe Ser Cys Ser Val Met
    195                 200                 205

His Glu Ala Leu His Asn His Tyr Thr Gln Lys Ser Leu Ser Leu Ser
210                 215                 220

Pro Gly Lys
225

<210> SEQ ID NO 15
<211> LENGTH: 227
<212> TYPE: PRT
<213> ORGANISM: Artificial Sequence
<220> FEATURE:
<223> OTHER INFORMATION: human IgG1 Fc-region derived Fc-region polypeptide with a P329G mutation and S354C, T366W mutation

<400> SEQUENCE: 15

```
Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Gly Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Cys Arg Asp Glu Leu Thr Lys Asn Gln Val Ser
    130                 135                 140

Leu Trp Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225
```

<210> SEQ ID NO 16
<211> LENGTH: 227
<212> TYPE: PRT
<213> ORGANISM: Artificial Sequence
<220> FEATURE:
<223> OTHER INFORMATION: human IgG1 Fc-region derived Fc-region
      polypeptide with L234A, L235A, P329G and Y349C, T366S, L368A,
      Y407V mutations

<400> SEQUENCE: 16

```
Asp Lys Thr His Thr Cys Pro Pro Cys Pro Ala Pro Glu Ala Ala Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95
```

Lys Glu Tyr Lys Cys Lys Val Ser Asn Lys Ala Leu Gly Ala Pro Ile
            100                 105                 110

Glu Lys Thr Ile Ser Lys Ala Lys Gly Gln Pro Arg Glu Pro Gln Val
        115                 120                 125

Cys Thr Leu Pro Pro Ser Arg Asp Glu Leu Thr Lys Asn Gln Val Ser
130                 135                 140

Leu Ser Cys Ala Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Val Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225

<210> SEQ ID NO 17
<211> LENGTH: 227
<212> TYPE: PRT
<213> ORGANISM: Artificial Sequence
<220> FEATURE:
<223> OTHER INFORMATION: human IgG1 Fc-region derived Fc-region
      polypeptide with L234A, L235A, P329G mutations and S354C, T366W
      mutations

<400> SEQUENCE: 17

Asp Lys Thr His Thr Cys Pro Pro Cys Pro Ala Pro Glu Ala Ala Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Gly Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Cys Arg Asp Glu Leu Thr Lys Asn Gln Val Ser
130                 135                 140

Leu Trp Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser

Pro Gly Lys
225

<210> SEQ ID NO 18
<211> LENGTH: 229
<212> TYPE: PRT
<213> ORGANISM: Artificial Sequence
<220> FEATURE:
<223> OTHER INFORMATION: human IgG4 Fc-region derived Fc-region
      polypeptide with S228P and L235E mutations

<400> SEQUENCE: 18

Glu Ser Lys Tyr Gly Pro Pro Cys Pro Pro Cys Pro Ala Pro Glu Phe
1               5                   10                  15

Glu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Ser Gln Glu Glu Met Thr Lys Asn Gln
    130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
    210                 215                 220

Leu Ser Leu Gly Lys
225

<210> SEQ ID NO 19
<211> LENGTH: 229
<212> TYPE: PRT
<213> ORGANISM: Artificial Sequence
<220> FEATURE:
<223> OTHER INFORMATION: human IgG4 Fc-region derived Fc-region
      polypeptide with S228P, L235E mutations and P329G mutation

<400> SEQUENCE: 19

Glu Ser Lys Tyr Gly Pro Pro Cys Pro Pro Cys Pro Ala Pro Glu Phe
1               5                   10                  15

Glu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val

```
                35                  40                  45
Ser Gln Glu Asp Pro Glu Val Gln Phe Asn Trp Tyr Val Asp Gly Val
 50                  55                  60

Glu Val His Asn Ala Lys Thr Lys Pro Arg Glu Glu Gln Phe Asn Ser
 65                  70                  75                  80

Thr Tyr Arg Val Val Ser Val Leu Thr Val Leu His Gln Asp Trp Leu
                 85                  90                  95

Asn Gly Lys Glu Tyr Lys Cys Lys Val Ser Asn Lys Gly Leu Gly Ser
                100                 105                 110

Ser Ile Glu Lys Thr Ile Ser Lys Ala Lys Gly Gln Pro Arg Glu Pro
            115                 120                 125

Gln Val Tyr Thr Leu Pro Pro Ser Gln Glu Glu Met Thr Lys Asn Gln
        130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
    210                 215                 220

Leu Ser Leu Gly Lys
225

<210> SEQ ID NO 20
<211> LENGTH: 229
<212> TYPE: PRT
<213> ORGANISM: Artificial Sequence
<220> FEATURE:
<223> OTHER INFORMATION: human IgG4 Fc-region derived Fc-region
      polypeptide with S354C, T366W mutations

<400> SEQUENCE: 20

Glu Ser Lys Tyr Gly Pro Pro Cys Pro Ser Cys Pro Ala Pro Glu Phe
 1               5                  10                  15

Leu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
 50                  55                  60

Glu Val His Asn Ala Lys Thr Lys Pro Arg Glu Glu Gln Phe Asn Ser
 65                  70                  75                  80

Thr Tyr Arg Val Val Ser Val Leu Thr Val Leu His Gln Asp Trp Leu
                 85                  90                  95

Asn Gly Lys Glu Tyr Lys Cys Lys Val Ser Asn Lys Gly Leu Pro Ser
                100                 105                 110

Ser Ile Glu Lys Thr Ile Ser Lys Ala Lys Gly Gln Pro Arg Glu Pro
            115                 120                 125

Gln Val Tyr Thr Leu Pro Pro Cys Gln Glu Glu Met Thr Lys Asn Gln
        130                 135                 140

Val Ser Leu Trp Cys Leu Val Lys Gly Phe Tyr Pro Ser Asp Ile Ala
145                 150                 155                 160
```

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
    210                 215                 220

Leu Ser Leu Gly Lys
225

<210> SEQ ID NO 21
<211> LENGTH: 229
<212> TYPE: PRT
<213> ORGANISM: Artificial Sequence
<220> FEATURE:
<223> OTHER INFORMATION: human IgG4 Fc-region derived Fc-region
      polypeptide with Y349C, T366S, L368A, Y407V mutations

<400> SEQUENCE: 21

Glu Ser Lys Tyr Gly Pro Pro Cys Pro Ser Cys Pro Ala Pro Glu Phe
1               5                   10                  15

Leu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125

Gln Val Cys Thr Leu Pro Pro Ser Gln Glu Glu Met Thr Lys Asn Gln
    130                 135                 140

Val Ser Leu Ser Cys Ala Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Val Ser Arg Leu
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
    210                 215                 220

Leu Ser Leu Gly Lys
225

<210> SEQ ID NO 22
<211> LENGTH: 229
<212> TYPE: PRT
<213> ORGANISM: Artificial Sequence
<220> FEATURE:
<223> OTHER INFORMATION: human IgG4 Fc-region derived Fc-region
      polypeptide with a S228P, L235E and S354C, T366W mutations

<400> SEQUENCE: 22

```
Glu Ser Lys Tyr Gly Pro Pro Cys Pro Pro Cys Pro Ala Pro Glu Phe
1               5                   10                  15

Glu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Cys Gln Glu Glu Met Thr Lys Asn Gln
    130                 135                 140

Val Ser Leu Trp Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
    210                 215                 220

Leu Ser Leu Gly Lys
225
```

<210> SEQ ID NO 23
<211> LENGTH: 229
<212> TYPE: PRT
<213> ORGANISM: Artificial Sequence
<220> FEATURE:
<223> OTHER INFORMATION: human IgG4 Fc-region derived Fc-region polypeptide with a S228P, L235E and Y349C, T366S, L368A, Y407V mutations

<400> SEQUENCE: 23

```
Glu Ser Lys Tyr Gly Pro Pro Cys Pro Pro Cys Pro Ala Pro Glu Phe
1               5                   10                  15

Glu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
```

```
            100             105             110
Ser Ile Glu Lys Thr Ile Ser Lys Ala Lys Gly Gln Pro Arg Glu Pro
        115                 120                 125

Gln Val Cys Thr Leu Pro Pro Ser Gln Glu Glu Met Thr Lys Asn Gln
        130                 135                 140

Val Ser Leu Ser Cys Ala Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Val Ser Arg Leu
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
210                 215                 220

Leu Ser Leu Gly Lys
225

<210> SEQ ID NO 24
<211> LENGTH: 229
<212> TYPE: PRT
<213> ORGANISM: Artificial Sequence
<220> FEATURE:
<223> OTHER INFORMATION: human IgG4 Fc-region derived Fc-region
      polypeptide with a P329G mutation

<400> SEQUENCE: 24

Glu Ser Lys Tyr Gly Pro Pro Cys Pro Ser Cys Pro Ala Pro Glu Phe
1               5                   10                  15

Leu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Gly Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Ser Gln Glu Glu Met Thr Lys Asn Gln
        130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
210                 215                 220
```

Leu Ser Leu Gly Lys
225

<210> SEQ ID NO 25
<211> LENGTH: 229
<212> TYPE: PRT
<213> ORGANISM: Artificial Sequence
<220> FEATURE:
<223> OTHER INFORMATION: human IgG4 Fc-region derived Fc-region
      polypeptide with a P239G and Y349C, T366S, L368A, Y407V mutations

<400> SEQUENCE: 25

Glu Ser Lys Tyr Gly Pro Pro Cys Pro Ser Cys Pro Ala Pro Glu Phe
1               5                   10                  15

Leu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
50                  55                  60

Glu Val His Asn Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Gly Ser
            100                 105                 110

Ser Ile Glu Lys Thr Ile Ser Lys Ala Lys Gly Gln Pro Arg Glu Pro
        115                 120                 125

Gln Val Cys Thr Leu Pro Pro Ser Gln Glu Glu Met Thr Lys Asn Gln
130                 135                 140

Val Ser Leu Ser Cys Ala Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Val Ser Arg Leu
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
    210                 215                 220

Leu Ser Leu Gly Lys
225

<210> SEQ ID NO 26
<211> LENGTH: 229
<212> TYPE: PRT
<213> ORGANISM: Artificial Sequence
<220> FEATURE:
<223> OTHER INFORMATION: human IgG4 Fc-region derived Fc-region
      polypeptide with a P329G and S354C, T366W mutations

<400> SEQUENCE: 26

Glu Ser Lys Tyr Gly Pro Pro Cys Pro Ser Cys Pro Ala Pro Glu Phe
1               5                   10                  15

Leu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

```
Ser Gln Glu Asp Pro Glu Val Gln Phe Asn Trp Tyr Val Asp Gly Val
    50                  55                  60

Glu Val His Asn Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Gly Ser
                100                 105                 110

Ser Ile Glu Lys Thr Ile Ser Lys Ala Lys Gly Gln Pro Arg Glu Pro
                115                 120                 125

Gln Val Tyr Thr Leu Pro Pro Cys Gln Glu Glu Met Thr Lys Asn Gln
    130                 135                 140

Val Ser Leu Trp Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
                180                 185                 190

Thr Val Asp Lys Ser Arg Trp Gln Glu Gly Asn Val Phe Ser Cys Ser
                195                 200                 205

Val Met His Glu Ala Leu His Asn His Tyr Thr Gln Lys Ser Leu Ser
210                 215                 220

Leu Ser Leu Gly Lys
225

<210> SEQ ID NO 27
<211> LENGTH: 229
<212> TYPE: PRT
<213> ORGANISM: Artificial Sequence
<220> FEATURE:
<223> OTHER INFORMATION: human IgG4 Fc-region derived Fc-region
      polypeptide with a S228P, L235E, P329G and Y349C, T366S, L368A,
      Y407V mutations

<400> SEQUENCE: 27

Glu Ser Lys Tyr Gly Pro Pro Cys Pro Pro Cys Pro Ala Pro Glu Phe
1               5                   10                  15

Glu Gly Gly Pro Ser Val Phe Leu Phe Pro Pro Lys Pro Lys Asp Thr
                20                  25                  30

Leu Met Ile Ser Arg Thr Pro Glu Val Thr Cys Val Val Val Asp Val
            35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Gly Ser
                100                 105                 110

Ser Ile Glu Lys Thr Ile Ser Lys Ala Lys Gly Gln Pro Arg Glu Pro
                115                 120                 125

Gln Val Cys Thr Leu Pro Pro Ser Gln Glu Glu Met Thr Lys Asn Gln
    130                 135                 140

Val Ser Leu Ser Cys Ala Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
```

165                 170                 175

Pro Pro Val Leu Asp Ser Asp Gly Ser Phe Phe Leu Val Ser Arg Leu
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
    210                 215                 220

Leu Ser Leu Gly Lys
225

<210> SEQ ID NO 28
<211> LENGTH: 229
<212> TYPE: PRT
<213> ORGANISM: Artificial Sequence
<220> FEATURE:
<223> OTHER INFORMATION: human IgG4 Fc-region derived Fc-region
      polypeptide with a S228P, L235E, P329G and S354C, T366W mutations

<400> SEQUENCE: 28

Glu Ser Lys Tyr Gly Pro Pro Cys Pro Pro Cys Pro Ala Pro Glu Phe
1               5                   10                  15

Glu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Gly Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Cys Gln Glu Glu Met Thr Lys Asn Gln
    130                 135                 140

Val Ser Leu Trp Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
    210                 215                 220

Leu Ser Leu Gly Lys
225

<210> SEQ ID NO 29
<211> LENGTH: 105
<212> TYPE: PRT
<213> ORGANISM: homo sapiens

<400> SEQUENCE: 29

Gln Pro Lys Ala Ala Pro Ser Val Thr Leu Phe Pro Pro Ser Ser Glu

```
                1               5                   10                  15
Glu Leu Gln Ala Asn Lys Ala Thr Leu Val Cys Leu Ile Ser Asp Phe
                        20                  25                  30

Tyr Pro Gly Ala Val Thr Val Ala Trp Lys Ala Asp Ser Ser Pro Val
            35                  40                  45

Lys Ala Gly Val Glu Thr Thr Thr Pro Ser Lys Gln Ser Asn Asn Lys
        50                  55                  60

Tyr Ala Ala Ser Ser Tyr Leu Ser Leu Thr Pro Glu Gln Trp Lys Ser
65                      70                  75                  80

His Arg Ser Tyr Ser Cys Gln Val Thr His Glu Gly Ser Thr Val Glu
                    85                  90                  95

Lys Thr Val Ala Pro Thr Glu Cys Ser
                100                 105

<210> SEQ ID NO 30
<211> LENGTH: 107
<212> TYPE: PRT
<213> ORGANISM: Homo sapiens

<400> SEQUENCE: 30

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
                    20                  25                  30

Tyr Pro Arg Glu Ala Lys Val Gln Trp Lys Val Asp Asn Ala Leu Gln
            35                  40                  45

Ser Gly Asn Ser Gln Glu Ser Val Thr Glu Gln Asp Ser Lys Asp Ser
        50                  55                  60

Thr Tyr Ser Leu Ser Ser Thr Leu Thr Leu Ser Lys Ala Asp Tyr Glu
65                      70                  75                  80

Lys His Lys Val Tyr Ala Cys Glu Val Thr His Gln Gly Leu Ser Ser
                    85                  90                  95

Pro Val Thr Lys Ser Phe Asn Arg Gly Glu Cys
                100                 105
```